United States Patent
Brown et al.

(10) Patent No.: US 11,098,015 B2
(45) Date of Patent: *Aug. 24, 2021

(54) MALATE SALT OF N-(4-{[6,7-BIS(METHYLOXY)QUINOLIN-4-YL]OXY}PHENYL)-N'-(4-FLUOROPHENYL)CYCLOPROPANE-1,1-DICARBOXAMIDE, AND CRYSTALLINE FORMS THEREOF FOR THE TREATMENT OF CANCER

(71) Applicant: Exelixis, Inc., Alameda, CA (US)

(72) Inventors: Adrian St. Clair Brown, Ely (GB); Peter Lamb, Oakland, CA (US); William P. Gallagher, Princeton, NJ (US)

(73) Assignee: Exelixis, Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/171,752

(22) Filed: Feb. 9, 2021

(65) Prior Publication Data

US 2021/0163416 A1    Jun. 3, 2021

Related U.S. Application Data

(60) Continuation of application No. 17/149,365, filed on Jan. 14, 2021, which is a continuation of application No. 17/070,514, filed on Oct. 14, 2020, which is a continuation of application No. 16/796,250, filed on Feb. 20, 2020, now abandoned, which is a continuation of application No. 15/617,725, filed on Jun. 8, 2017, now abandoned, which is a division of application No. 14/340,871, filed on Jul. 25, 2014, now Pat. No. 9,809,549, which is a division of application No. 13/145,054, filed as application No. PCT/US2010/021194 on Jan. 15, 2010, now Pat. No. 8,877,776.

(60) Provisional application No. 61/145,421, filed on Jan. 16, 2009.

(51) Int. Cl.
C07D 215/22    (2006.01)
C07D 215/233   (2006.01)

(52) U.S. Cl.
CPC ....... *C07D 215/22* (2013.01); *C07D 215/233* (2013.01)

(58) Field of Classification Search
CPC .......................... C07D 215/22; C07D 215/233
See application file for complete search history.

(56) References Cited

U.S. PATENT DOCUMENTS

| | | |
|---|---|---|
| 4,808,715 A | 2/1989 | Boyle et al. |
| 4,829,069 A | 5/1989 | Takahashi et al. |
| 5,034,393 A | 7/1991 | Hackle et al. |
| 5,123,951 A | 6/1992 | See et al. |
| 5,238,951 A | 8/1993 | Sher et al. |
| 5,334,747 A | 8/1994 | Steffen et al. |
| 5,480,883 A | 1/1996 | Spada et al. |
| 5,650,415 A | 7/1997 | Tang et al. |
| 5,747,498 A | 5/1998 | Schnur et al. |
| 5,770,599 A | 6/1998 | Gibson |
| 5,962,407 A | 10/1999 | Kelly |
| 5,962,458 A | 10/1999 | Lohmann et al. |
| 6,071,921 A | 6/2000 | Lohmann et al. |
| 6,103,728 A | 8/2000 | Tang et al. |
| 6,126,917 A | 10/2000 | Mishani et al. |
| 6,143,764 A | 11/2000 | Kubo et al. |
| 6,184,225 B1 | 2/2001 | Thomas et al. |
| 6,204,267 B1 | 3/2001 | Tang et al. |
| 6,225,307 B1 | 5/2001 | Camden et al. |
| 6,235,746 B1 | 5/2001 | Davis et al. |
| 6,288,082 B1 | 9/2001 | Wissner et al. |
| 6,294,532 B1 | 9/2001 | Thomas et al. |
| 6,337,335 B1 | 1/2002 | Hutchings et al. |
| 6,344,459 B1 | 2/2002 | Bridget et al. |
| 6,358,962 B2 | 3/2002 | Uckun et al. |
| 6,362,336 B1 | 3/2002 | Lohmann et al. |
| 6,391,874 B1 | 5/2002 | Cockerill et al. |
| 6,403,580 B1 | 6/2002 | Himmelsbach et al. |
| 6,414,148 B1 | 7/2002 | Thomas et al. |
| 6,432,406 B1 | 8/2002 | Goldberg et al. |
| 6,448,261 B1 | 9/2002 | Bakthavatchalam et al. |
| 6,469,013 B2 | 10/2002 | Uckun et al. |
| 6,472,391 B2 | 10/2002 | Matsumo et al. |
| 6,476,031 B1 | 11/2002 | Chakravarty et al. |

(Continued)

FOREIGN PATENT DOCUMENTS

| | | |
|---|---|---|
| CN | 1543462 A | 11/2004 |
| CN | 1914191 A | 2/2007 |

(Continued)

OTHER PUBLICATIONS

US 6,344,555 B1, 02/2002, Bridget et al. (withdrawn)

(Continued)

*Primary Examiner* — Timothy R Rozof
(74) *Attorney, Agent, or Firm* — Honigman LLP; Heidi M. Berven

(57) ABSTRACT

Disclosed are malate salts of N-(4-{[6,7-bis(methyloxy)-quinolin-4-yl]oxy}phenyl)-N'-(4-fluorophenyl)cyclopropane-1,1-dicarboxamide, including a (L)-malate salt, a (D)-malate salt, a (DL) malate salt, and mixtures thereof; and crystalline and amorphous forms of the malate salts. Also disclosed are pharmaceutical compositions comprising at least one malate salts of N-(4-{[6,7-bis(methyloxy)quinolin-4-yl]oxy}phenyl)-N'-(4-fluorophenyl)-cyclopropane-1,1-dicarboxamide; and methods of treating cancer comprising administering at least one malate salt of N-(4-{[6,7-bis(methyloxy)quinolin-4-yl]oxy}phenyl)-N'-(4-fluorophenyl)cyclopropane-1, 1-dicarboxamide.

3 Claims, 27 Drawing Sheets

(56) References Cited

U.S. PATENT DOCUMENTS

| | | |
|---|---|---|
| 6,476,040 B1 | 11/2002 | Norris et al. |
| 6,495,556 B2 | 12/2002 | Uckun et al. |
| 6,514,971 B1 | 2/2003 | Thomas et al. |
| 6,521,618 B2 | 2/2003 | Boschelli et al. |
| 6,521,629 B2 | 2/2003 | Fox et al. |
| 6,525,046 B1 | 2/2003 | Cirillo et al. |
| 6,552,027 B2 | 4/2003 | Uckun et al. |
| 6,562,818 B1 | 5/2003 | Bridges |
| 6,593,333 B1 | 7/2003 | Cumming |
| 6,602,863 B1 | 8/2003 | Bridges et al. |
| 6,608,048 B2 | 8/2003 | Tsou et al. |
| 6,608,071 B2 | 8/2003 | Altmann et al. |
| 6,627,621 B2 | 9/2003 | Nagaoka et al. |
| 6,627,634 B2 | 9/2003 | Himmelsbach et al. |
| 6,630,489 B1 | 10/2003 | Crawley et al. |
| 6,642,242 B2 | 11/2003 | Collis et al. |
| 6,649,620 B2 | 11/2003 | Collis et al. |
| 6,653,305 B2 | 11/2003 | Himmelsbach et al. |
| 6,656,946 B2 | 12/2003 | Himmelsbach et al. |
| 6,664,390 B2 | 12/2003 | Barth et al. |
| 6,673,803 B2 | 1/2004 | Thomas et al. |
| 6,693,198 B2 | 2/2004 | Ajami et al. |
| 6,710,070 B2 | 3/2004 | Druzgala et al. |
| 6,716,835 B1 | 4/2004 | Picaud et al. |
| 6,723,726 B1 | 4/2004 | Cockerill et al. |
| 6,727,256 B1 | 4/2004 | Carter et al. |
| 6,734,303 B2 | 5/2004 | Ahman et al. |
| 6,740,651 B2 | 5/2004 | Himmelsbach et al. |
| 6,753,338 B2 | 6/2004 | Young |
| 6,759,410 B1 | 7/2004 | Adams et al. |
| 6,797,823 B1 | 9/2004 | Kubo et al. |
| 6,809,097 B1 | 10/2004 | Thomas et al. |
| 6,821,987 B2 | 11/2004 | Kubo et al. |
| 6,946,483 B2 | 9/2005 | Assens et al. |
| 7,125,905 B2 | 10/2006 | Tang et al. |
| 7,135,466 B2 | 11/2006 | Sakai et al. |
| 7,253,286 B2 | 8/2007 | Funahashi et al. |
| 7,319,107 B2 | 1/2008 | Eisinger et al. |
| 7,425,564 B2 | 9/2008 | Fujiwara et al. |
| 7,579,473 B2 | 8/2009 | Bannen et al. |
| 7,598,258 B2 | 10/2009 | Kubo et al. |
| 7,977,345 B2 | 7/2011 | Bannen et al. |
| 7,999,006 B2 | 8/2011 | Lamb |
| 8,067,436 B2 | 11/2011 | Bannen et al. |
| 8,178,532 B2 | 5/2012 | Bannen et al. |
| 8,314,232 B2 | 11/2012 | Deschamps et al. |
| 8,476,298 B2 | 7/2013 | Bannen et al. |
| 8,497,284 B2 | 7/2013 | Bannen et al. |
| 8,877,776 B2 * | 11/2014 | Brown ............... A61P 5/14 514/312 |
| 9,174,947 B2 | 11/2015 | Bannen et al. |
| 9,724,342 B2 | 8/2017 | Wilson et al. |
| 9,809,549 B2 | 11/2017 | Brown et al. |
| 9,861,624 B2 | 1/2018 | Aftab et al. |
| 10,034,873 B2 | 7/2018 | Wilson et al. |
| 10,039,757 B2 | 9/2018 | Wilson et al. |
| 10,159,666 B2 | 12/2018 | Aftab et al. |
| 10,166,225 B2 | 1/2019 | Aftab et al. |
| 10,736,886 B2 | 8/2020 | Aftab et al. |
| 2002/0032208 A1 | 3/2002 | Lohmann et al. |
| 2002/0049197 A1 | 4/2002 | Himmelsback et al. |
| 2002/0137757 A1 | 9/2002 | Uckun et al. |
| 2002/0161010 A1 | 10/2002 | Chakravarty et al. |
| 2002/0161226 A1 | 10/2002 | Uckun et al. |
| 2002/0165243 A1 | 11/2002 | Uckun et al. |
| 2002/0169165 A1 | 11/2002 | Kath et al. |
| 2002/0169180 A1 | 11/2002 | Himmelsbach et al. |
| 2002/0173509 A1 | 11/2002 | Himmelsbach et al. |
| 2002/0173646 A1 | 11/2002 | Thomas et al. |
| 2002/0177600 A1 | 11/2002 | Griffin et al. |
| 2002/0177601 A1 | 11/2002 | Himmelsbach et al. |
| 2003/0013728 A1 | 1/2003 | Uckun et al. |
| 2003/0018029 A1 | 1/2003 | Barker et al. |
| 2003/0045525 A1 | 3/2003 | Collis et al. |
| 2003/0045537 A1 | 3/2003 | Lee et al. |
| 2003/0065180 A1 | 4/2003 | Tsou et al. |
| 2003/0066060 A1 | 4/2003 | Ford |
| 2003/0069230 A1 | 4/2003 | Becker et al. |
| 2003/0069248 A1 | 4/2003 | Chakravarty et al. |
| 2003/0082831 A1 | 5/2003 | Fodor et al. |
| 2003/0087907 A1 | 5/2003 | Kubo et al. |
| 2003/0100753 A1 | 5/2003 | Boulton et al. |
| 2003/0149056 A1 | 8/2003 | Wissner et al. |
| 2003/0149062 A1 | 8/2003 | Jung et al. |
| 2003/0153568 A1 | 8/2003 | Kusack et al. |
| 2003/0171386 A1 | 9/2003 | Connell et al. |
| 2003/0175736 A1 | 9/2003 | Chinnaiyan et al. |
| 2003/0176451 A1 | 9/2003 | Carter et al. |
| 2004/0147603 A1 | 7/2004 | Giron et al. |
| 2004/0204386 A1 | 10/2004 | Rama et al. |
| 2004/0242603 A1 | 12/2004 | Jujiwara et al. |
| 2005/0049264 A1 | 3/2005 | Miwa et al. |
| 2005/0209247 A1 | 9/2005 | Cai et al. |
| 2005/0288290 A1 | 12/2005 | Borzilleri et al. |
| 2006/0111375 A1 | 5/2006 | Shumizu et al. |
| 2006/0199843 A1 | 9/2006 | Zeldis |
| 2007/0005492 A1 | 1/2007 | Kim |
| 2007/0054928 A1 | 3/2007 | Bannen et al. |
| 2007/0078159 A1 | 4/2007 | Matsushima et al. |
| 2007/0225307 A1 | 9/2007 | Bannen et al. |
| 2007/0244116 A1 | 10/2007 | Bannen et al. |
| 2008/0004273 A1 | 1/2008 | Raeppel et al. |
| 2008/0161305 A1 | 7/2008 | Forsyth et al. |
| 2008/0207617 A1 | 8/2008 | Miwa et al. |
| 2008/0298657 A1 | 12/2008 | Shiraishi et al. |
| 2008/0312221 A1 | 12/2008 | Fujiwara et al. |
| 2008/0318924 A1 | 12/2008 | Matsushima et al. |
| 2009/0105299 A1 | 4/2009 | Bannen et al. |
| 2009/0170896 A1 | 7/2009 | Bannen et al. |
| 2009/0274693 A1 | 11/2009 | Gilmer et al. |
| 2011/0059081 A1 | 3/2011 | Bacus |
| 2011/0077233 A1 | 3/2011 | Bannen et al. |
| 2011/0229469 A1 | 9/2011 | Johns |
| 2012/0022065 A1 | 1/2012 | Banen et al. |
| 2012/0035212 A1 | 2/2012 | Brown et al. |
| 2012/0070368 A1 | 3/2012 | Bannen et al. |
| 2012/0184523 A1 | 7/2012 | Bannen et al. |
| 2012/0252840 A1 | 10/2012 | Aftab et al. |
| 2012/0270872 A1 | 10/2012 | Cannon et al. |
| 2012/0282179 A1 | 11/2012 | Aftab et al. |
| 2013/0030172 A1 | 1/2013 | Wilson et al. |
| 2013/0142790 A1 | 6/2013 | Gilmer et al. |
| 2013/0143881 A1 | 6/2013 | Cannon et al. |
| 2013/0150363 A1 | 6/2013 | Gilmer et al. |
| 2013/0197230 A1 | 8/2013 | Wilson et al. |
| 2013/0252940 A1 | 9/2013 | Bannen et al. |
| 2014/0121239 A1 | 5/2014 | Aftab |
| 2014/0155396 A1 | 6/2014 | Bannen et al. |
| 2015/0238477 A1 | 8/2015 | Aftab |
| 2015/0376133 A1 | 12/2015 | Bannen et al. |
| 2016/0000772 A1 | 1/2016 | Aftab et al. |
| 2016/0082019 A1 | 3/2016 | Sweeney et al. |
| 2016/0185725 A1 | 6/2016 | Bannen et al. |

FOREIGN PATENT DOCUMENTS

| | | |
|---|---|---|
| CN | 101454311 A | 6/2009 |
| EP | 1044969 | 10/2000 |
| EP | 1117653 | 7/2001 |
| EP | 1153920 | 11/2001 |
| EP | 0860433 | 7/2002 |
| EP | 1243582 | 9/2002 |
| EP | 0875506 | 2/2003 |
| EP | 0880508 | 4/2003 |
| EP | 1304110 | 4/2003 |
| EP | 0990647 | 7/2003 |
| EP | 0912570 | 9/2003 |
| EP | 0973746 | 9/2003 |
| EP | 0977737 | 9/2003 |
| EP | 1340748 | 9/2003 |
| EP | 1411046 | 4/2004 |
| EP | 1447405 | 8/2004 |
| EP | 1143950 | 3/2005 |
| EP | 1301440 | 3/2005 |

(56) References Cited

FOREIGN PATENT DOCUMENTS

| | | |
|---|---|---|
| EP | 2062886 | 5/2009 |
| EP | 2062886 A1 | 5/2009 |
| WO | 1995015758 | 6/1995 |
| WO | 1995019774 | 7/1995 |
| WO | 1996009294 | 3/1996 |
| WO | 1996015118 | 5/1996 |
| WO | 1996040142 | 12/1996 |
| WO | 1997003069 | 1/1997 |
| WO | 1997017329 | 5/1997 |
| WO | 1997030035 | 8/1997 |
| WO | 1997032856 | 9/1997 |
| WO | 1998013350 | 4/1998 |
| WO | 1998013354 | 4/1998 |
| WO | 1999010349 | 3/1999 |
| WO | 2000018761 | 4/2000 |
| WO | 2000020402 | 4/2000 |
| WO | 2000021955 | 4/2000 |
| WO | 2000043366 | 7/2000 |
| WO | 2000047212 | 8/2000 |
| WO | 2000055141 | 9/2000 |
| WO | 2000056338 | 9/2000 |
| WO | 2000056720 | 9/2000 |
| WO | 2000068199 | 11/2000 |
| WO | 2000068201 | 11/2000 |
| WO | 2001021596 | 3/2001 |
| WO | 2001021597 | 3/2001 |
| WO | 2001047890 | 7/2001 |
| WO | 2001055116 | 8/2001 |
| WO | 2001068186 | 9/2001 |
| WO | 2001094341 | 12/2001 |
| WO | 2002000188 | 1/2002 |
| WO | 2002000649 | 1/2002 |
| WO | 2002009684 | 2/2002 |
| WO | 2002016352 | 2/2002 |
| WO | 2002018351 | 3/2002 |
| WO | 2002030924 | 4/2002 |
| WO | 2002030926 | 4/2002 |
| WO | 2002032872 | 4/2002 |
| WO | 2002034744 | 5/2002 |
| WO | 2002036570 | 5/2002 |
| WO | 2002044166 | 6/2002 |
| WO | 2002085895 | 10/2002 |
| WO | 2002088110 | 11/2002 |
| WO | 2002092571 | 11/2002 |
| WO | 2002092577 | 11/2002 |
| WO | 2002092578 | 11/2002 |
| WO | 2002092579 | 11/2002 |
| WO | 2002096884 | 12/2002 |
| WO | 2003000188 | 1/2003 |
| WO | 2003000660 | 1/2003 |
| WO | 2003016305 A1 | 2/2003 |
| WO | 2003033472 | 4/2003 |
| WO | 2003037252 | 5/2003 |
| WO | 2003040109 | 5/2003 |
| WO | 2003045395 | 6/2003 |
| WO | 2003047584 | 6/2003 |
| WO | 2003048159 | 6/2003 |
| WO | 2003050108 | 6/2003 |
| WO | 2003053960 | 7/2003 |
| WO | 2003055491 | 7/2003 |
| WO | 2003055492 | 7/2003 |
| WO | 2003055866 | 7/2003 |
| WO | 2003064413 | 7/2003 |
| WO | 2003064421 | 8/2003 |
| WO | 2003064431 | 8/2003 |
| WO | 2003066060 | 8/2003 |
| WO | 2003082831 | 10/2003 |
| WO | 2003089439 | 10/2003 |
| WO | 2003093238 | 11/2003 |
| WO | 2004006846 | 1/2004 |
| WO | 2004018473 | 4/2004 |
| WO | 2004035572 | 4/2004 |
| WO | 2004039782 | 5/2004 |
| WO | 2004041829 | 5/2004 |
| WO | 2004054585 | 7/2004 |
| WO | 2004055003 | 7/2004 |
| WO | 2004058267 | 7/2004 |
| WO | 2004060373 | 7/2004 |
| WO | 2005003140 | 1/2005 |
| WO | 2005005389 | 1/2005 |
| WO | 2005030140 | 4/2005 |
| WO | 2005073224 | 8/2005 |
| WO | 2005075454 | 8/2005 |
| WO | 2005075454 A1 | 8/2005 |
| WO | 2005089353 | 9/2005 |
| WO | 2006014325 | 2/2006 |
| WO | 2007102074 | 9/2007 |
| WO | 2007103308 | 9/2007 |
| WO | 2007109799 | 9/2007 |
| WO | 2008070616 A2 | 6/2008 |
| WO | 2008076415 | 6/2008 |
| WO | 2009085972 A1 | 7/2009 |
| WO | 2010039248 | 4/2010 |
| WO | 2010083414 | 7/2010 |

OTHER PUBLICATIONS

Akutsu, et al., "An X-ray Diffraction System with Controlled Relative Humidity and Temperature", The Rigaku Journal, vol. 14, No. 1, pp. 1-4, 1997.
Aulton, Ed., "Pharmaceuticals: The Science of Dosage Form Design," Churchill Livingstone, 2d Ed., 2002.
Bavin, et. al, "Polymorphism in Process Development." Chemistry & Industry, 527-529, Aug. 21, 1989.
Berge et al., "Pharmaceutical salts," J Pharm. Sci., 66 (1): 1-19 (Jan. 1977).
Boschelli et al., "Synthesis and Src kinase inhibitory activity of a series of 4-phenylamino-3-quinolinecarbonitriles," J Med. Chem., 44 (5): 822-833 (Mar. 1, 2001).
Brittain, Ed., "Polymorphism in Pharmaceutical Solids." Marcel Dekker, Inc., 1999. pp. 183-226.
Byrn, et al., "Pharmaceutical Solids: A Strategic Approach to Regulatory Considerations." Pharmaceutical Research, 12: 945-954, 1995.
Datapharm Communications Ltd., "Almogran SmPC." Available at www.medicines.org.uk/emc/medicine/21973/spc/ (last visited Dec. 12, 2013).
Datapharm Communications Ltd., "Sanomigran SmPC." Available at http://www.medicines.org.uk/emc/medicine/14045/SPC (last visited Dec. 12, 2013).
Datapharm Communications Ltd., "Sutent SmPC." Available at http://www.medicines.org.uk/emc/medicine/18531 (last visited Dec. 12, 2013).
European Medicines Agency, "Committee for orphan medicinal products Dec. 2008 plenary meeting monthly report", Doc. Ref. EMEA/666785/2008 Corr. 2, Dec. 22, 2008.
Gadamasetti, et al., "Process Chemistry in the Pharmaceutical Industry, vol. 2—Challenges in an Ever Changing Climate." CRC Press, 2008, pp. 49-63.
Gennaro, Ed., "Remington: The Science and Practice of Pharmacy," Lippincott Williams & Wilkins, 20th Ed., 1996.
Hancock, et al., "Molecular Mobility of Amorphous Pharmaceutical Solids Below their Glass Transition Temperatures", Pharmaceutical Research, vol. 12, No. 6, pp. 799-806, 1995.
Inaba, et al., "Expression and significance of c-met protein in papillary thyroid carcinoma." Tokai J. Exp. Clin. Med., 27(2): 43-49, 2002.
International Conference on Harmonisation of Technical Requirements for Registration of Pharmaceuticals for Human Use, "Specifications: Test Procedures and Acceptance Criteria for New Drug Substances and New Drug Products: Chemical Substances." ICH Harmonised Tripartite Guideline Q6A. Oct. 6, 1999.
International Search Report for PCT/US2010/021194, dated Mar. 24, 2010.
IUPAC, "Dissolution", Compendium of Chemical Terminology, 2nd ed (the "Gold Book"), online version available at: http://goldbook.iupac.org. Excerpt from version 2.3.3, last updated Feb. 24, 2014.

(56) References Cited

OTHER PUBLICATIONS

IUPAC, "Solubility", Compendium of Chemical Terminology, 2nd ed (the "Gold Book"), online version available at: http://goldbook.iupac.org. Excerpt from version 2.3.3, last updated Feb. 24, 2014.
Kubo et al., "Synthesis and structure-activity relationship for new series of 4- phenoxyquinoline derivatives as specific inhibitors of platelet-derived growth factor receptor tyrosine kinase," Bioorg. Med. Chem., 11 (23), 5117-5133 (Nov. 17, 2003).
Kumar, et al., "An overview of automated systems relevant in pharmaceutical salt screening." Drug Discovery Today, 12: 1046-1053, 2007.
Kumar, et al., "Preparation and Characterization of Salt Forms of Enalapril." Pharmaceutical Development and Technology, 13:345-357, 2008.
L. Liu et al: "Synergistic Effects of Foretinib with HER-Targeted Agents in MET and HER1- or HER2-Coactivated Tumor Cells", Molecular Cancer Therapeutics,vol. 10, No. 3, Mar. 1, 2011(Mar. 1, 2011), 518-530.
Laird et al., "Small molecule tyrosine kinase inhibitors: clinical development of anticancer agents," Expert Opin. Investig. Drugs, 12 (1): 51-64 (Jan. 2003).
Liu, L., et al. "Synergistic Effects of Foretinib with HER-Targeted Agents in MET and HER1- or HER2-Coactivated Tumor Cells", Molecular Cancer Therapeutics, vol. 10, No. 3, Mar. 1, 2011
Meulenaar, Jelte, et al., "Slow Dissolution Behavior of Amorphous Capecitabine", International Journal of Pharmaceutics, No. 441, pp. 213-217, Dec. 5, 2012.
Morris, et al., "An integrated approached to the selection of optimal salt form for a new drug candidate." International Journal of Pharmaceutics, 105:209-217, 1994.
National Pharmacopeia Commission, "Pharmacopeia of the People's Republic of China 2000 Edition Part II", pp. 1-4, Jan. 31, 2000.
Ogita et al., "Synthesis and structure-activity relationship of diarylamide urea derivatives as selective inhibitors of the proliferation of human coronary artery smooth muscle cells," Bioorg. Med. Chem., 10 (6): 1865-1871 (Jun. 2002).
Paulekuhn, et. al., "Trends in Active Pharmaceutical Ingredient Salt Selection based on Analysis of the Orange Book Database." J. Med. Chem., No. 50, pp. 6665-6672, 2007.
Tong, "Salt Screening and Selection: New Challenges and Considerations in the Modern Pharmaceutical R&D Paradigm." Integrated Drug Product Development Process, University of Utah, Jul. 17-19, 2006.
Towler, et al., "An Investigation into the Influence of Counterion on the Properties of Some Amorphous Organic Salts", Molecular Pharmaceutics, vol. 5, No. 6, pp. 946-955, Aug. 16, 2008.
Notice of Opposition to EP 2387563 and grounds of opposition by Opponent 1, dated Dec. 5, 2013.
Notice of Opposition to EP 2387563 and grounds of opposition by Opponent 2, dated Dec. 5, 2013.
Notice of Opposition to EP 2387563 and grounds of opposition by Opponent 3, dated Dec. 6, 2013.
Written submission by Opponent 3 in Opposition Proceedings regarding EP 2387563, dated Feb. 25, 2014.
Written submission by Patentee in Opposition Proceedings regarding EP 2387563, dated Sep. 22, 2014.
Written submission by Opponent 3 in Opposition Proceedings regarding EP 2387563, dated Oct. 14, 2015.
Written submission by Patentee in Opposition Proceedings regarding EP 2387563, dated Oct. 14, 2015.
Written submission by Patentee in Opposition Proceedings regarding EP 2387563, dated Dec. 8, 2015.
Written Decision of Written submission by Patentee in Opposition Proceedings regarding EP 2387563, dated Dec. 8, 2015.position Division in Opposition Proceedings regarding EP 2387563, dated Jul. 1, 2016.
Grounds of Appeal by Opponent 1 in Opposition Proceedings regarding EP 2387563, dated May 17, 2016.
Grounds of Appeal by OpGrounds of Appeal by Opponent 2 in Opposition Proceedings regarding EP 2387563, dated May 17, 2016.
Grounds of Appeal by Opponent 3 in Opposition Proceedings regarding EP 2387563, dated May 17, 2016.
Written Submission by Patentee in Opposition Proceedings regarding EP 2387563, dated Oct. 4, 2016.
Written Submission by Opponent 2 in Opposition Proceedings regarding EP 2387563, dated Oct. 25, 2016.
Guideline for Drug Stability Testing, Appendixes XIX C and XIX D, Pharmacopoeia of People's Republic of China (2000), vol. 2, Chemical Industry Press, Jan. 2000.
Written Submission by Opponent 2 in Opposition Proceedings regarding EP 2387563, dated Mar. 6, 2017.
Written Submission by Opponent 2 in Opposition Proceedings regarding EP 2387563, dated Mar. 17, 2017.
Written Submission by Opponent 3 in Opposition Proceedings regarding EP 2387563, dated Apr. 20, 2018.
Written submission by Patentee in Opposition Proceedings regarding EP 2387563, dated Sep. 25, 2018.
EPO Communication regarding Scheduling of Oral Proceedings regarding EP 2387563, dated Nov. 21, 2019.
EPO Summons to Oral Proceedings regarding EP 2387563, dated Nov. 26, 2019.
Preliminary Opinion regarding EP 2387563, dated Aug. 7, 2020.
Written submission by Patentee in Opposition Proceedings regarding EP 2387563, dated Oct. 20, 2020.
EPO Communication regarding Rescheduling of Oral Proceedings regarding EP 2387563, dated Nov. 6, 2020.
Wang, Yulong, et al., Research progress of the relationship between HGF/Met and invasion of thyroid cancer, Chinese Oncology, vol. 15, No. 3, 2005, pp. 299-301.
Yang, L.V. and Du Guanhua, Polymorphic Drugs, People's Medical Publishing House, published on Oct. 31, 2009.
Ping, Qineng et al., Modern Pharmacetutics, China Medical Science and Technology Press, the first printing of the first edition on Oct. 1998, pp. 25-32, published on Oct. 31, 1998.
Caira, M. R., "Crystalline Polymorphism of Organic Compounds," Topics in Current Chemistry, vol. 198, pp. 163-208, 1998.
Electronic supplementary information (ESI) available with CrystEngConun, 2005, 7(55),342-345.
Stahl, P. Heinrich and Camille G. Wermuth, Handbook of Pharmaceutical Salts Properties, Selection and Use, Publisher: Wiley-VCH. (Chapter-11, Selected Procedures for the Preparation of Pharmaceutically Acceptable Salts, p. 250-263). 2003.
Guillory, J. Keith, Drugs and Pharmaceutical Sciences, vol. 95, Polymorphism in pharmaceutical solids, Chapter-5, "Generation of Polymorphs, Hydrates, Solvates and Amorphous Solids", pp. 183-186, 1999, Edited by Rarity G. Brittain.
Rodriguez-Spong, et al., "General principles of pharmaceutical solid polymorphism: a supramolecular perspective", Advance Drug Delivery Reviews, vol. 56, pp. 241-274, 2004.
Swanepoel, Eta, Wilna Liebenberg, Melgardt M. de Villiers; European Journal of Pharmaceutics and Biophartnacentics, 2003, 55. 345-349.
Bastin, Richard J., et al., "Salt Selection and Optimisation Procedures for Pharmaceutical New Chemical Entities", Organic Process Research & Development, 2000, vol. 4, pp. 427-435.
Wikipedia, citation for Malic acid, (https://en.wikipedia.org/wiki/Malic_acid), printed Jun. 21, 2021, 5 pages.
Notice of Pre-Grant Opposition to PI 1006812-0 filed by Zodiac Produtos Farmaceuticos S/A, dated May 12, 2019.
Vippagunta, et al., "Crystalline solids", Advanced Drug Delivery Reviews, vol. 48, pp. 3-26, 2001.
Bighley, Lyle D., et al., Salt Forms of Drugs and Absorption, in 13 Encyclopedia of Pharmaceutical Technology 453 (James Swarbrick & James C. Boylan eds., 1995).
Shekunov, B. Yu, et al., Crystallization process in pharmaceutical technology and drug delivery design, Journal of Crystal Growth 211 (2000) 122-36.
Yu, L. et al., "Physical Characterization of Polymorphic Drugs: An Integrated Characterization Strategy" PSTT 1 (3):118-127 (1998).

(56) References Cited

OTHER PUBLICATIONS

Rodriquez, Hornedo and D. Murphy, "Significance of Controlling Crystallization Mechanisms and Kinetics in Pharmaceutical Systems," Journal of Pharmaceutical Sciences, 88, 651-660 (1999).
Gu, C.H., et al., "Polymorph Screening: Influence of Solvents on the Rate of Solvent—Mediated Polymorphic Transformation" Journal of Pharmaceutical Sciences, 90, 1878-1890 (2001).
Haleblian and W. McCrone, "Pharmaceutical Applications of Polymorphism," J. Pharmaceutical Sciences, 58, 911-929 (1969).
Haleblian, J.K., "Characterization of Habits and Crystalline Modification of Solids and Their Pharmaceutical Applications," J. Pharmaceutical Sciences, 64, 1269-1288.
Threlfall, T.L., "Analysis of Organic Polymorphs. A Review," Analyst, 120, 2435-2460 (1995).
McCrone, Walter C., Polymorphism, Physics and Chemistry of the Organic Solid State 727, Fox, et al., eds., (1965).
Guillory, Keith, "Generation of Polymorphs, Hydrates, Solvates, and Amorphous Solids," Polymorphism in Pharmaceutical Sciences (H. Brittain ed. 1999).
Desiraju, Gautam R., "Crystal Gazing: Structure Prediction and Polymorphism," 278 Science 404 (Oct. 17, 1997).
FDA, Guideline for Submitting Supporting Documentation in Drug Applications for the Manufacture of Drug Substances, Center for Drug Evaluation and Research (Feb. 1987).
MSN Laboratories, Defendants' initial invalidity contentions for U.S. Pat. No. 8,877,776 dated Jun. 25, 2020.
Exhibit A to MSN Laboratories, Defendants' initial invalidity contentions dated Jun. 25, 2020 for U.S. Pat. No. 8,877,776.
English Translation of Invalidation Request for CN 201610140984. 2, Jiangsu Hansoh, dated Mar. 29, 2021.
English Translation of Invalidation Request for CN 201610140984. 2, Jiangsu Aosaikang, dated Mar. 12, 2021.
Notice of Opposition for 3402/KOLNP/2011, Antony David, dated Feb. 9, 2021.
Notice of Opposition for 3402/KOLNP/2011, Dhaval Dayabhai Diyora, dated Feb. 9, 2021.
Notice of Opposition for 3402/KOLNP/2011, Natco Pharma Ltd., dated Feb. 9, 2021.
MSN Laboratories Responses and Objections to Plaintiffs Fourth Set of Interrogatories (Nos. 22-29) dated Jun. 21, 2021.
Exhibit A to MSN Laboratories Response to Interrogatory No. 22 dated Jun. 21, 2021 for U.S. Pat. No. 9,809,549.
Remington: The Science and Practice of Pharmacy (Alfonso R. Gennaro et al. eds., 20th ed. 2000), 700-704.

* cited by examiner

Moisture Sorption of Compound (I), Form N-1

MALATE SALT OF N-(4-{[6,7-BIS(METHYLOXY) QUINOLIN-4-YL]OXY}PHENYL)-N'-(4-FLUOROPHENYL)CYCLOPROPANE-1,1-DICARBOXAMIDE, AND CRYSTALLINE FORMS THEREOF FOR THE TREATMENT OF CANCER

CROSS-REFERENCE TO RELATED APPLICATIONS

This application is a continuation application of U.S. Ser. No. 17/149,365, filed Jan. 14, 2021, which is a continuation application of U.S. Ser. No. 17/070,514, filed Oct. 14, 2020, which is a continuation application of U.S. Ser. No. 16/796,250, filed Feb. 20, 2020, which is a continuation application of U.S. Ser. No. 15/617,725, filed Jun. 8, 2017, which is a division of U.S. Ser. No. 14/340,871, filed Jul. 25, 2014, which is a division of U.S. Ser. No. 13/145,054, filed Oct. 20, 2011, which claims priority under 35 U.S.C. § 371 to Patent Cooperation Treaty application PCT/US2010/021194, filed Jan. 15, 2010, which claims the benefit of U.S. provisional application No. 61/145,421, filed Jan. 16, 2009, the entire contents of which are incorporated herein by reference.

TECHNICAL FIELD

This disclosure relates to malate salts of N-(4-{[6,7-bis(methyloxy)-quinolin-4-yl]oxy}phenyl)-N'-(4-fluorophenyl)cyclopropane-1,1-dicarboxamide and to crystalline and amorphous forms of the malate salts of N-(4-{[6,7-bis(methyloxy)-quinolin-4-yl]oxy}phenyl)-N'-(4-fluorophenyl)cyclopropane-1,1-dicarboxamide. The malate salts of N-(4-{[6,7-bis(methyloxy)-quinolin-4-yl]oxy}phenyl)-N'-(4-fluorophenyl)cyclopropane-1,1-dicarboxamide include one of (1) the (L)-malate salt, (2) the (D)-malate salt, (3) the (D,L)-malate salt, and (4) mixtures thereof. The disclosure also relates to pharmaceutical compositions comprising at least one malate salt of N-(4-{[6,7-bis(methyloxy)quinolin-4-yl]oxy}phenyl)-N'-(4-fluorophenyl)-cyclopropane-1,1-dicarboxamide.

The disclosure also relates to pharmaceutical compositions comprising a crystalline or an amorphous form of at least one malate salt of N-(4-{[6,7-bis(methyloxy)quinolin-4-yl]oxy}phenyl)-N'-(4-fluorophenyl)-cyclopropane-1,1-dicarboxamide.

The disclosure also relates to methods of treating cancer comprising administering at least one malate salt of N-(4-{[6,7-bis(methyloxy)quinolin-4-yl]oxy}phenyl)-N'-(4-fluorophenyl)cyclopropane-1,1-dicarboxamide.

The disclosure further relates to methods of treating cancer comprising administering a crystalline or an amorphous form of at least one malate salt of N-(4-{[6,7-bis(methyloxy)quinolin-4-yl]oxy}phenyl)-N'-(4-fluorophenyl)cyclopropane-1,1-dicarboxamide.

BACKGROUND

Traditionally, dramatic improvements in the treatment of cancer are associated with identification of therapeutic agents acting through novel mechanisms. One mechanism that can be exploited in cancer treatment is the modulation of protein kinase activity because signal transduction through protein kinase activation is responsible for many of the characteristics of tumor cells. Protein kinase signal transduction is of particular relevance in, for example, thyroid, gastric, head and neck, lung, breast, prostate, and colorectal cancers, as well as in the growth and proliferation of brain tumor cells.

Protein kinases can be categorized as receptor type or non-receptor type. Receptor-type tyrosine kinases are comprised of a large number of transmembrane receptors with diverse biological activity. For a detailed discussion of the receptor-type tyrosine kinases, see Plowman et al., DN&P 7(6): 334-339, 1994. Since protein kinases and their ligands play critical roles in various cellular activities, deregulation of protein kinase enzymatic activity can lead to altered cellular properties, such as uncontrolled cell growth associated with cancer. In addition to oncological indications, altered kinase signaling is implicated in numerous other pathological diseases, including, for example, immunological disorders, cardiovascular diseases, inflammatory diseases, and degenerative diseases. Therefore, protein kinases are attractive targets for small molecule drug discovery. Particularly attractive targets for small-molecule modulation with respect to antiangiogenic and antiproliferative activity include receptor type tyrosine kinases Ret, c-Met, and VEGFR2.

The kinase c-Met is the prototypic member of a subfamily of heterodimeric receptor tyrosine kinases (RTKs) which include Met, Ron and Sea. The endogenous ligand for c-Met is the hepatocyte growth factor (HGF), a potent inducer of angiogenesis. Binding of HGF to c-Met induces activation of the receptor via autophosphorylation resulting in an increase of receptor dependent signaling, which promotes cell growth and invasion. Anti-HGF antibodies or HGF antagonists have been shown to inhibit tumor metastasis in vivo (See: Maulik et al Cytokine & Growth Factor Reviews 2002 13, 41-59). c-Met, VEGFR2 and/or Ret overexpression has been demonstrated on a wide variety of tumor types including breast, colon, renal, lung, squamous cell myeloid leukemia, hemangiomas, melanomas, astrocytic tumor (which includes glioblastoma, giant cell glioblastoma, gliosarcoma, and glioblastoma with oligodendroglial components). The Ret protein is a transmembrane receptor with tyrosine kinase activity. Ret is mutated in most familial forms of medullary thyroid cancer. These mutations activate the kinase function of Ret and convert it into an oncogene product.

Inhibition of EGF, VEGF and ephrin signal transduction will prevent cell proliferation and angiogenesis, two key cellular processes needed for tumor growth and survival (Matter A. Drug Disc. Technol. 20016, 1005-1024). Kinase KDR (refers to kinase insert domain receptor tyrosine kinase) and flt-4 (fms-like tyrosine kinase-4) are both vascular endothelial growth factor (VEGF) receptors. Inhibition of EGF, VEGF and ephrin signal transduction will prevent cell proliferation and angiogenesis, two key cellular processes needed for tumor growth and survival (Matter A. Drug Disc. Technol. 2001 6, 1005-1024). EGF and VEGF receptors are desirable targets for small molecule inhibition.

Accordingly, small-molecule compounds that specifically inhibit, regulate and/or modulate the signal transduction of kinases, particularly including Ret, c-Met and VEGFR2 described above, are particularly desirable as a means to treat or prevent disease states associated with abnormal cell proliferation and angiogenesis. One such small-molecule is N-(4-{[6,7-bis(methyloxy)quinolin-4-yl]oxy}phenyl)-N'-(4-fluorophenyl)cyclopropane-1,1-dicarboxamide, which has the chemical structure:

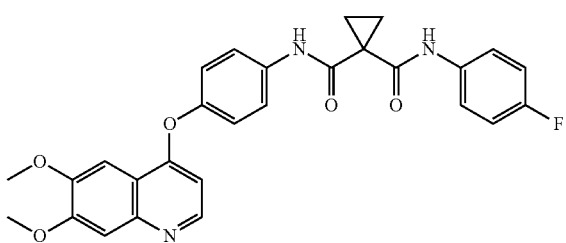 [SMILES: COc1cc2nccc(Oc3ccc(NC(=O)C4(C(=O)Nc5ccc(F)cc5)CC4)cc3)c2cc1OC]

WO 2005/030140 describes the synthesis of N-(4-{[6,7-bis(methyloxy)quinolin-4-yl]oxy}phenyl)-N'-(4-fluorophenyl)cyclopropane-1,1-dicarboxamide (Example 12, 37, 38, and 48) and also discloses the therapeutic activity of this molecule to inhibit, regulate and/or modulate the signal transduction of kinases, (Assays, Table 4, entry 289). Example 48 is on paragraph [0353] in WO 2005/030140.

Besides therapeutic efficacy, the drug developer endeavors to provide a suitable form of the therapeutic agent that has properties relating to processing, manufacturing, storage stability, and/or usefulness as a drug. Accordingly, the discovery of a form that possesses some or all of these desired properties is vital to drug development.

Applicants have found a salt form of the drug N-(4-{[6,7-bis(methyloxy)quinolin-4-yl]oxy}phenyl)-N'-(4-fluorophenyl)cyclopropane-1,1-dicarboxamide that has suitable properties for use in a pharmaceutical composition for the treatment of a proliferative disease such as cancer. The novel salt form of the invention exists in crystalline and amorphous forms

SUMMARY

This disclosure relates to malate salts of N-(4-{[6,7-bis(methyloxy)quinolin-4-yl]oxy}phenyl)-N'-(4-fluorophenyl)cyclopropane-1,1-dicarboxamide as described herein, pharmaceutical compositions thereof as described herein, and uses thereof as described herein.

Another aspect relates to crystalline and amorphous forms of the malate salts of N-(4-{[6,7-bis(methyloxy)quinolin-4-yl]oxy}phenyl)-N'-(4-fluorophenyl)cyclopropane-1,1-dicarboxamide as described herein, pharmaceutical compositions thereof as described herein, and uses thereof as described herein.

DETAILED DESCRIPTION

Figure 1:
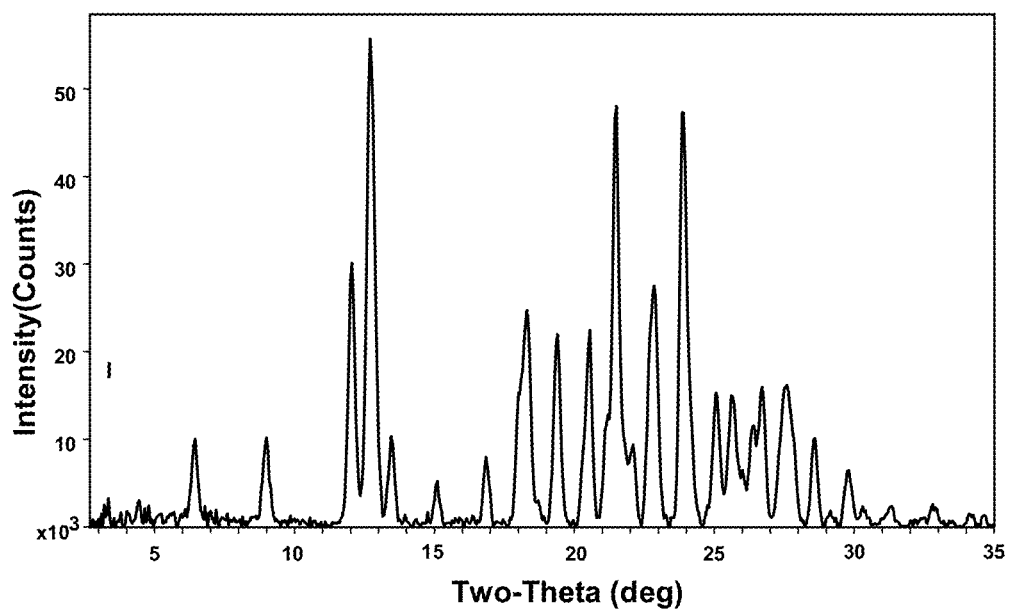
FIG. 1 shows the experimental XRPD pattern for crystalline Compound (I), Form N-1 at 25° C.

This disclosure relates to improvements of the physiochemical properties of N-(4-{[6,7-bis(methyloxy)quinolin-4-yl]oxy}phenyl)-N'-(4-fluorophenyl)cyclopropane-1,1-dicarboxamide, whereby this compound may be suitable for drug development. Disclosed herein are malate salts of N-(4-{[6,7-bis(methyloxy)quinolin-4-yl]oxy}phenyl)-N'-(4-fluorophenyl)cyclopropane-1,1-dicarboxamide. New solid state forms of those salts are also disclosed. The malate salts as well as their crystalline and amorphous forms disclosed herein each represent separate aspects of the disclosure. Although the malate salts and their solid state forms are described herein, the invention also relates to novel compositions containing the disclosed salts and solid state forms. Therapeutic uses of the salts and solid state forms described as well as therapeutic compositions containing them represent separate aspects of the disclosure. The techniques used to characterize the salts and their solid state forms are described in the examples below. These techniques, alone or in combination, may be used to characterize the salts and their solid state forms disclosed herein. The salts and their solid state forms may be also characterized by reference to the disclosed figures.

N-(4-{[6,7-bis(methyloxy)quinolin-4-yl]oxy}phenyl)-N'-(4-fluorophenyl)-cyclopropane-1,1-dicarboxamide was found to have an enzyme Ret IC$_{50}$ value of about 5.2 nM (nanomolar) and an enzyme c-Met IC$_{50}$ value of about 1.3 nM (nanomolar). The assay that was used to measure this c-Met activity is described in paragraph [0458] in WO2005-030140.

RET biochemical activity was assessed using a Luciferase-Coupled Chemiluminescent Kinase assay (LCCA) format as described in WO2005-030140. Kinase activity was measured as the percent ATP remaining following the kinase reaction. Remaining ATP was detected by luciferase-luciferin-coupled chemiluminescence. Specifically, the reaction was initiated by mixing test compounds, 2 µM ATP, 1 µM poly-EY and 15 nM RET (baculovirus expressed human RET kinase domain M700-D1042 with a $(His)_6$ tag on the N-terminus) in a 20 uL assay buffer (20 mM Tris-HCL pH 7.5, 10 mM $MgCl_2$, 0.01% Triton X-100, 1 mM DTT, 3 mM $MnCl_2$). The mixture was incubated at ambient temperature for 2 hours after which 20 uL luciferase-luciferin mix was added and the chemiluminescent signal read using a Wallac Victor$^2$ reader. The luciferase-luciferin mix consists of 50 mM HEPES, pH 7.8, 8.5 ug/mL oxalic acid (pH 7.8), 5 mM DTT, 0.4% Triton X-100, 0.25 mg/mL coenzyme A, 63 µM AMP, 28 µg/mL luciferin and 40,000 units of light/mL luciferase.

Malate Salts of N-(4-{[6,7-bis(methyloxy)quinolin-4-yl]oxy}phenyl)-N-(4-fluorophenyl)cyclopropane-1,1-dicarboxamide This disclosure relates to malate salts of N-(4-{[6,7-bis(methyloxy)quinolin-4-yl]oxy}phenyl)-N'-(4-fluorophenyl)cyclopropane-1,1-dicarboxamide. These malate salts are a combination of N-(4-{[6,7-bis(methyloxy)quinolin-4-yl]oxy}phenyl)-N'-(4-fluorophenyl)cyclopropane-1,1-dicarboxamide with malic acid which forms a 1:1 malate salt of N-(4-{[6,7-bis(methyloxy)quinolin-4-yl]oxy}phenyl)-N'-(4-fluorophenyl)cyclopropane-1,1-dicarboxamide.

Malic acid has the following structure:

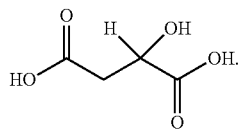

Due to its chiral carbon, two enantiomers of malic acid exist, (L)-malic acid and (D)-malic acid.

(L)-malic acid has the following structure:

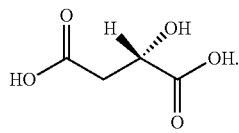

There are various names or designations for the (L)-malic acid that are known in the art. These include butanedioic acid, hydroxy-, (2S)-(9CI); butanedioic acid, hydroxy-, (S)-; malic acid, L-(8CI); malic acid, 1-(3CI); (−)-(S)-malic acid; (−)-Hydroxysuccinic acid; (−)-(L)-malic acid; (−)-malic acid; (2S)-2-hydroxybutanedioic acid; (2S)-2-hydroxysuccinic acid; (S)-malic acid; apple acid; L-(−)-malic acid; (L)-malic acid; NSC 9232; S-(−)-malic acid; and S-2-hydroxybutanedioic acid.

(D) malic acid has the following structure:

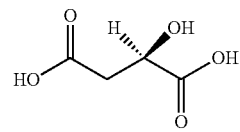

There are various names or designations for the (D)-malic acid that are known in the art. These include butanedioic acid, 2-hydroxy-, (2R)-, butanedioic acid, hydroxy-, (2R)-(9CI); butanedioic acid, hydroxy-, (R)-; (+)-malic acid; (2R)-2-hydroxybutanedioic acid; (2R)-malic acid; (R)-(+)-malic acid; (R)-malic acid; D-(+)-2-hydroxysuccinic acid; D-(+)-malic acid; and D-malic acid.

As discussed above, the chemical structure of N-(4-{[6,7-bis(methyloxy)quinolin-4-yl]oxy}phenyl)-N'-(4-fluorophenyl)cyclopropane-1,1-dicarboxamide is

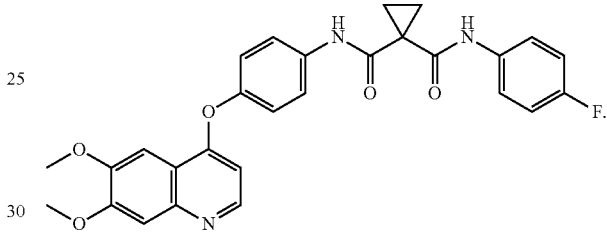

There are no chiral carbons in its chemical structure. There are various names for N-(4-{[6,7-bis(methyloxy)quinolin-4-yl]oxy}phenyl)-N'-(4-fluorophenyl)cyclopropane-1,1-dicarboxamide which are publicly known, and some of these various names or designations include 1,1-cyclopropanedicarboxamide, N'-[4-[(6,7-dimethoxy-4-quinolinyl)oxy]phenyl]-N-(4-fluorophenyl)- and 1,1-cyclopropanedicarboxamide, N-[4-[(6,7-dimethoxy-4-quinolinyl)oxy]phenyl]-N'-(4-fluorophenyl)-(9CI).

N-(4-{[6,7-bis(methyloxy)quinolin-4-yl]oxy}phenyl)-N'-(4-fluorophenyl)cyclopropane-1,1-dicarboxamide can be prepared according to any of several different methodologies, either on a gram scale (<1 kg) or a kilogram scale (>1 kg). A gram-scale method is set forth in WO 2005-030140, which describes the synthesis of N-(4-{[6,7-bis(methyloxy)quinolin-4-yl]oxy}phenyl)-N'-(4-fluorophenyl)cyclopropane-1,1-dicarboxamide (Examples 25, 37, 38, and 48), which is hereby incorporated by reference. Alternatively, N-(4-{[6,7-bis(methyloxy)quinolin-4-yl]oxy}phenyl)-N'-(4-fluorophenyl)cyclopropane-1,1-dicarboxamide, including the active compound(s), can be prepared on a kilogram scale using the procedure set forth in Example 1 below.

This disclosure relate to malate salts of N-(4-{[6,7-bis(methyloxy)quinolin-4-yl]oxy}phenyl)-N'-(4-fluorophenyl)cyclopropane-1,1-dicarboxamide:
  the (L)-malate salt of N-(4-{[6,7-bis(methyloxy)quinolin-4-yl]oxy}phenyl)-N'-(4-fluorophenyl)cyclopropane-1,1-dicarboxamide, (Compound (I));
  the (D)-malate salt of N-(4-{[6,7-bis(methyloxy)quinolin-4-yl]oxy}phenyl)-N'-(4-fluorophenyl)cyclopropane-1,1-dicarboxamide, (Compound (II)); and
  the (DL)-malate salt of N-(4-{[6,7-bis(methyloxy)quinolin-4-yl]oxy}phenyl)-N'-(4-fluorophenyl)cyclopropane-1,1-dicarboxamide (Compound (III)).

Each has improved properties over N-(4-{[6,7-bis(methyloxy)quinolin-4-yl]oxy}phenyl)-N'-(4-fluorophenyl)cyclopropane-1,1-dicarboxamide and its other salts. The names used herein to characterize a specific form, e.g. "N-2" etc., are not to be limited so as to exclude any other substance possessing similar or identical physical and chemical characteristics, but rather such names are used as mere identifiers that are to be interpreted in accordance with the characterization information presented herein.

The malate salts of N-(4-{[6,7-bis(methyloxy)quinolin-4-yl]oxy}phenyl)-N'-(4-fluorophenyl)cyclopropane-1,1-dicarboxamide, and particularly Compound (I), have a preferred combination of pharmaceutical properties for development. Under the conditions of 25° C./60% relative humidity (RH) and 40° C./60% RH, Compound (I) showed no change in assay, purity, moisture and dissolution. The DSC/TGA showed the Compound (I) to be stable up to 185° C. No solvent losses were observed. The uptake of water by the (L)-malate salt was reversible with a slight hysteresis. The amount of water taken up was calculated at about 0.60 wt % at 90% RH. The (L)-malate salt was synthesized with good yield and purity >90% and had sufficient solubility for use in a pharmaceutical composition. The amount of water associated with this salt was calculated at about 0.5 wt % by Karl Fischer analysis and correlates with TGA and GVS analysis. The (D)-malate salt of N-(4-{[6,7-bis(methyloxy)quinolin-4-yl]oxy}phenyl)-N'-(4-fluorophenyl)cyclopropane-1,1-dicarboxamide) will have the same properties as the (L)-malate salt of N-(4-{[6,7-bis(methyloxy)quinolin-4-yl]oxy}phenyl)-N'-(4-fluorophenyl)cyclopropane-1,1-dicarboxamide).

The Compound (I) salt itself, and separately its crystalline and amorphous forms, exhibit beneficial properties over the free base and the other salts of the N-(4-{[6,7-bis(methyloxy)quinolin-4-yl]oxy}-phenyl)-N'-(4-fluorophenyl)cyclopropane-1,1-dicarboxamide. For example, the hydrochloride salt of N-(4-{[6,7-bis(methyloxy)quinolin-4-yl]oxy}phenyl)-N'-(4-fluorophenyl)cyclopropane-1,1-dicarboxamide exhibits undesirable moisture sensitivity, changing phase upon exposure to high humidity (75% humidity) and high temperature (40° C.). The maleate salt had low solubility. The tartrate salt had low crystallinity and low solubility. The phosphate salt exhibited an 8% weight gain due to absorption of $H_2O$—the highest among the salts tested.

The water solubility of the various salts was determined using 10 mg solids per mL water. The salts were prepared in a salt screen by reacting an acetone solution of the freebase with stock tetrahydrofuran (THF) solutions of a range of acids in about a 1:1 molar ratio. Table 1 below summarizes the water solubility and other data relating to the free base and each salt.

TABLE 1

| | Solubility (mg/ml) | |
|---|---|---|
| Free base | <<0.001 | very low solubility |
| Propionate | <<0.001 | no salt formation; mixture of free base and acid |
| Acetate | <<0.001 | no salt formation; mixture of free base and acid |
| Succinate | 0.010 | no salt formation; mixture of free base and acid |
| Benzoate | 0.005 | no salt formation; mixture of free base and acid |
| L-Lactate | 0.015 | Amorphous, salt |
| Pyroglutamate | 0.44 | Amorphous, salt |
| Glycolate | 0.016 | Amorphous, salt |
| L-Ascorbate | 0.053 | low crystallinity |
| Sulfate | 0.004 | Crystalline salt, low solubility |
| Tosylate | 0.007 | Crystalline salt, low solubility |
| Malonate | 0.003 | Crystalline salt, low solubility |
| 2,5 dihydroxybenzoate | <<0.001 | Crystalline Salt, low solubility |
| Fumarate | 0.008 | Crystalline Salt, low solubility |
| Citrate | 0.002 | Crystalline Salt, low solubility |
| Mesylate | 0.175 | Crystalline Salt; possible sulfonic acid formation when made with alcohol |
| Esylate | 0.194 | Crystalline Salt; possible sulfonic acid formation when made with alcohol |
| Benzenesulfonate | 0.039 | Crystalline Salt; possible sulfonic acid formation when made with alcohol |
| Chloride | 0.070 | Crystalline but Hygroscopic; possible hydrate formation. Change in XRPD pattern upon exposure to humidity. |
| Maleate | 0.005 | Crystalline salt, possible hydrate formation; low solubility; different XRPD pattern observed upon scale up (possible polymorphism issue) |
| Phosphate | 0.026 | Crystalline but Hygroscopic. |
| L-Tartrate | 0.014 | Low degree of crystallinity; Hygroscopic. |
| (L)-Malate | 0.059 | Crystalline; non-Hygroscopic with no indication of hydrate formation. Suitable solubility, and chemical/physical stability. |

Another aspect of this disclosure relates to crystalline forms of Compound (I), which include the N-1 and/or the N-2 crystalline form of Compound (I) as described herein. Each of form of Compound (I) is a separate aspect of the disclosure. Similarly, another aspect of this disclosure relates to crystalline forms of Compound (II), which include the N-1 and/or the N-2 crystalline form of Compound (II) as described herein. Each of which is also a separate aspect of the disclosure. As is known in the art, the crystalline (D) malate salt will form the same crystalline form and have the same properties as crystalline Compound (I). See WO 2008/083319, which discusses the properties of crystalline enantiomers. Mixtures of the crystalline forms of Compounds (I) and (II) are another aspect of the disclosure.

The crystalline N-1 forms of Compounds (I) and (II) as described here may be characterized by at least one of the following:
(i) a solid state $^{13}C$ NMR spectrum with peaks at 18.1, 42.9, 44.5, 70.4, 123.2, 156.2, 170.8, 175.7, and 182.1 ppm, ±0.2 ppm;
(ii) a solid state $^{13}C$ NMR spectrum substantially in accordance with the pattern shown in FIG. 2;
(iii) an x-ray powder diffraction pattern (CuKα λ=1.5418 Å) comprising four or more peaks selected from: 6.4, 9.0, 12.0, 12.8, 13.5, 16.9, 19.4, 21.5, 22.8, 25.1, and 27.6 °2θ±0.2 °2θ, wherein measurement of the crystalline form is at an ambient room temperature;
(iv) an x-ray powder diffraction (XRPD) spectrum substantially in accordance with the pattern shown in FIG. 1;
(v) a solid state $^{15}N$ NMR spectrum with peaks at 118.6, 119.6, 120.7, 134.8, 167.1, 176.0, and 180 ppm, ±0.2 ppm; and/or
(vi) a solid state $^{15}N$ NMR spectrum substantially in accordance with the pattern shown in FIG. 3.

Other solid state properties which may be used to characterize the crystalline N-1 forms of Compounds (I) and (II) are shown in the figures and discussed in the examples below. For crystalline Compound (I), the solid state phase and the degree of crystallinity remained unchanged after exposure to 75% RH at 40° C. for 1 week.

The crystalline N-2 forms of Compounds (I) and (II) as described here may be characterized by at least one of the following:
(i) a solid state $^{13}$C NMR spectrum with peaks at 23.0, 25.9, 38.0, 54.4, 56.11, 41.7, 69.7, 102.0, 122.5, 177.3, 179.3, 180.0, and 180.3, ±0.2 ppm;
(ii) a solid state $^{13}$C NMR spectrum substantially in accordance with the pattern shown in FIG. 9;
(ii) an x-ray powder diffraction pattern (CuKα λ=1.5418 Å) comprising four or more peaks selected from: 6.4, 9.1, 12.0, 12.8, 13.7, 17.1, 20.9, 21.9, 22.6, and 23.7 °2θ±0.2 °2θ, wherein measurement of the crystalline form is at an ambient room temperature;
(iv) an x-ray powder diffraction (XRPD) spectrum substantially in accordance with the pattern shown in FIG. 8;
(v) a solid state $^{15}$N NMR spectrum with peaks at 118.5, 120.8, 135.1, 167.3, and 180.1 ppm; and/or
(vi) a solid state $^{15}$N NMR spectrum substantially in accordance with the pattern shown in FIG. 10.

Other solid state properties which may be used to characterize the crystalline N-2 forms of Compounds (I) and (II) are shown in the figures and discussed in the examples below.

In another embodiment, the disclosure relates to a crystalline form of Compound (I), as described herein in any of the aspects and/or embodiments, is substantially pure N-1 form.

In another embodiment, the disclosure relates to a crystalline form of Compound (I), as described herein in any of the aspects and/or embodiments, is substantially pure N-2 form.

The disclosure also relates to amorphous forms of Compounds (I) and (II). The preparation and solid state properties and characteristics of the amorphous form of Compound (I) are described in the examples below. The amorphous forms of Compounds (I) and (II) represent another aspect of the disclosure.

One further aspect of the disclosure relates to mixtures of Compound (I) and Compound (II). The mixtures may have from greater than zero weight % to less than 100 weight % Compound (I) and from less than 100 weight % to greater zero weight % Compound (II), based on the total weight of Compound (I) and Compound (II). In other embodiments, the mixture comprises from about 1 to about 99 weight % Compound (I) and from about 99 to about 1 weight % Compound (II), based on the total weight of Compound (I) and Compound (II) in said mixture. In a further embodiment, the mixture comprises from about 90 weight % to less than 100 weight % Compound (I) and from greater than zero weight % to about 10 weight % Compound (II), based on the total weight of Compound (I) and Compound (II). Accordingly, the mixture may have 1-10% by weight of Compound (I); 11-20% by weight of Compound (I); 21-30% by weight of Compound (I); 31-40% by weight of Compound (I); 41-50% by weight of Compound (I); 51-60% by weight of Compound (I); 61-70% by weight of Compound (I); 71-80% by weight of Compound (I); 81-90% by weight of Compound (I); or 91-99% by weight of Compound (I) with the remaining weight percentage of malate salt being that of Compound (II).

Another aspect of this disclosure relates to crystalline forms of (DL)-malate salt of N-(4-{[6,7-bis(methyloxy)quinolin-4-yl]oxy}phenyl)-N'-(4-fluorophenyl)cyclopropane-1,1-dicarboxamide, Compound (III). The (DL)-malate salt is prepared from racemic malic acid. The crystalline N-1 form of Compound (III) as described here may be characterized by at least one of the following:
(i) a solid state $^{13}$C NMR spectrum with four or more peaks selected from 20.8, 26.2, 44.8, 55.7, 70.7, 100.4, 101.0, 114.7, 115.2, 116.0, 119.7, 120.4, 121.6, 124.4, 136.9, 138.9, 141.1, 145.7, 150.3, 156.5, 157.6, 159.6, 165.2, 167.4, 171.2, 176.3, 182.1 ppm, ±0.2 ppm;
(ii) a solid state $^{13}$C NMR spectrum substantially in accordance with the pattern shown in FIG. 16;
(iii) a powder x-ray diffraction pattern (CuKα λ=1.5418 Å) comprising four or more 2θ values selected from: 12.8, 13.5, 16.9, 19.4, 21.5, 22.8, 25.1, and 27.6, ±0.2 °2θ, wherein measurement of the crystalline form is at temperature of room temperature;
(iv) an x-ray powder diffraction (XRPD) spectrum substantially in accordance with the pattern shown in FIG. 15;
(v) a solid state $^{15}$N NMR spectrum with peaks at 119.6, 134.7, and 175.5 ppm, ±0.2 ppm; and/or
(vi) a solid state $^{15}$N NMR spectrum substantially in accordance with the pattern shown in FIG. 17.

Other solid state properties which may be used to characterize the crystalline N-1 form of Compound (III) are shown in the figures and discussed in the examples below. In one embodiment, the N-1 Form of Compound (III) is characterized by unit cell parameters approximately equal to the following:

Cell dimensions: a=14.60 Å
b=5.20 Å
c=39.09 Å
α=90.0°
β=90.4°
γ=90.0°
Space group: P2$_1$/n
Molecules of Compound (I)/unit cell: 4
Volume=2969 Å$^3$
Density (calculated)=1.422 g/cm$^3$ The unit cell parameters of Form N-1 of Compound (III) were measured at a temperature of approximately 25° C., e.g., ambient or room temperature.

Each of the N-1 and N-2 crystalline forms of Compounds (T) and (IT) and the crystalline form N-1 of Compound (III) have unique characteristics that can distinguish them one from another. These characteristics can be understood by comparing the physical properties of the solid state forms which are presented in the Examples below. For example, Table 2 lists characteristic XRPD peak positions (°2θ±0.2 °2θ) for crystalline Compound (III), Form N-1 and Forms N-1 and N-2 of crystalline Compound (I). Amorphous forms do not display reflection peaks in their XRPD patterns.

TABLE 2

Characteristic diffraction peak positions (degrees 2θ ± 0.2) @ RT, based on pattern collected with a diffractometer (CuKα) with a spinning capillary.

| Compound (I) Form N-1 | Compound (I) Form N-2 | Compound (III) Form N-1 |
|---|---|---|
| 6.4 | 6.4 | 6.4 |
| 9.0 | 9.1 | 9.1 |
| 12.0 | 12.0 | 12.1 |
| 12.8 | 12.8 | 12.8 |
| 13.5 | 13.7 | 13.6 |
| 16.9 | 17.1 | 17.1 |
| 19.4* | 20.9* | 19.3 |
| 21.5* | 21.9* | 21.4 |
| 22.8* | 22.6 | 22.8 |

TABLE 2-continued

Characteristic diffraction peak positions (degrees 2θ ± 0.2) @ RT, based on pattern collected with a diffractometer (CuKα) with a spinning capillary.

| Compound (I) Form N-1 | Compound (I) Form N-2 | Compound (III) Form N-1 |
|---|---|---|
| 25.1* | 23.7 | 25.1 |
| 27.6* | — | 27.6 |

*unique reflections between Compound (I), Form N-1 and Compound (I), Form N-2.

The unique reflections between Forms N-1 and N-2 of crystalline Compound (II) are designated by an asterisk (*). As discussed above, Compound (II) is an enantiomer of Compound (I) and thus, Compound (II), Form N-1 will have the same characteristic reflection pattern and unique peaks as those listed in Table 2 for Compound (I), Form N-1. Likewise, Compound (II), Form N-2 will have the same characteristic reflection pattern and unique peaks as those listed in Table 2 for Compound (I), Form N-2. Compounds (I) and (II) are distinct from one another based on their absolute stereochemistry, i.e., the (L)-malate salt versus the (D)-malate salt, respectively. Crystalline Compound (III), Form N-1, is distinct as the (D,L)-malate salt.

The characteristic peaks from the solid state NMR may also serve to distinguish the crystalline and amorphous forms disclosed herein. For example, Table 3 lists characteristic solid state $^{13}C$ NMR peaks for crystalline Compound (III), Form N-1; crystalline Compound (I). Forms N-1 and N-2, and the amorphous form of Compound (I).

TABLE 3

Solid State Carbon-13 NMR Resonances (ppm, ±0.2 ppm)

| (I) Form N-1 | (I), Form N-2 | (III), Form N-1 | (I), Amorphous |
|---|---|---|---|
| 18.1 | 23.0 | 20.8 | 27.2 |
| 42.9 | 25.9 | 26.2 | 33.8 |
| 44.5 | 38.0 | 44.8 | 142.9 |
| 54.4 | 54.4 | 70.7 | — |
| 56.1 | 56.1 | 114.7 | — |
| 70.4 | 41.7 | 141.1 | — |
| 123.2 | 69.7 | 145.7 | — |
| 156.2 | 102.0 | 176.3 | — |
| 170.8 | 122.5 | 182.1 | — |
| 175.7 | 177.3 | — | — |
| 182.1 | 179.3 | — | — |
| — | 180.0 | — | — |
| — | 180.3 | — | — |

The solid state $^{19}F$ and $^{15}N$ NMR spectra, discussed below, provide data for similar comparison and characterization. As discussed above, being an enantiomer of Compound (I), crystalline Forms N-1 and N-2 and the amorphous form of Compound (II) will have the same solid state NMR resonances, and unique peaks between them, as those listed in Table 3 for Forms N-1 and N-2 of crystalline Compound (I).

Pharmaceutical Compositions and Methods of Treatment

Another aspect of this disclosure relates to a pharmaceutical composition comprising at least one of Compound (I), Compound (II), Compound (III), or combinations thereof, and a pharmaceutically acceptable excipient. The amount of Compound (I), Compound (II), Compound (III), or the combinations thereof in the pharmaceutical composition can be a therapeutically effective amount. Compound (I), Compound (II), or Compound (III) may individually be present in the pharmaceutical composition as one of the solid state forms discussed above or combinations thereof. The crystalline forms are preferred solid state forms. Accordingly another aspect of this disclosure relates to a solid or dispersion pharmaceutical composition comprising at least one of a therapeutically effective amount of a crystalline form of Compound (I), Compound (II), Compound (III), or combinations thereof, and a pharmaceutically acceptable excipient.

Another aspect of this disclosure relates to a method of treating cancer comprising administering to a subject in need thereof at least one of Compound (I), Compound (II), Compound (III) or combinations thereof. The amount of Compound (I), Compound (II), or combinations thereof administered can be a therapeutically effective amount. Compound (I), Compound (II), or Compound (III) may be individually administered as one of the solid state forms discussed above or combinations thereof. The crystalline forms are preferred solid state forms, with crystalline Compound (I), Form N-1 or N-2 being preferred. Accordingly another aspect of this disclosure relates to a method of treating cancer comprising administering to a subject in need thereof a therapeutically effective amount of at least one of Compound (I), Compound (II), Compound (III), or combinations thereof, wherein Compound (I), Compound (II), or Compound (III) is present in a crystalline form. In another aspect of this disclosure, the method of treatment may be practiced by administering a pharmaceutical composition of at least one of Compound (I), Compound (II), Compound (III) or combinations thereof such as discussed above.

Another aspect of this disclosure relates to a method of treating cancer, as discussed above, where the cancer treated is stomach cancer, esophageal carcinoma, kidney cancer, liver cancer, ovarian carcinoma, cervical carcinoma, large bowel cancer, small bowel cancer, brain cancer (including astrocytic tumor, which includes glioblastoma, giant cell glioblastoma, gliosarcoma, and glioblastoma with oligodendroglial components), lung cancer (including non-small cell lung cancer), bone cancer, prostate carcinoma, pancreatic carcinoma, skin cancer, bone cancer, lymphoma, solid tumors, Hodgkin's disease, non-Hodgkin's lymphoma or thyroid cancer thyroid cancer (including medullary thyroid cancer).

Tyrosine kinase inhibitors have also been used to treat non-small cell lung cancer (NSCLC). Gefitinib and erlotinib are angiogenesis inhibitors that target receptors of an epidermal growth factor called tyrosine kinase. Erlotinib and Gefitinib are currently being used for treating NSCLC. Another aspect of this disclosure relates to a method of treating non-small cell lung cancer (NSCLC) in a subject, the method comprising administering to the subject in need of the treatment a therapeutically effective amount of N-(4-{[6,7-bis(methyloxy)quinolin-4-yl]oxy}-phenyl)-N'-(4-fluorophenyl)cyclopropane-1,1-dicarboxamide, or a pharmaceutically acceptable salt thereof, optionally in combination with Erlotinib or Gefitinib. In another embodiment, the combination is with Erlotinib.

Another aspect of this disclosure relates to a method of treating non-small cell lung cancer (NSCLC) in a subject, the method comprising administering to the subject in need of the treatment a therapeutically effective amount of Erlotinib or Gefitinib in combination with at least one of Compound (I), Compound (II), Compound (III) or combinations thereof. Compound (I), Compound (II), or Compound (III) may be individually administered as one of the solid state forms discussed above or combinations thereof. The crystalline forms are preferred solid state forms. Accordingly another aspect of this disclosure relates to a method of treating a method of treating non-small cell lung cancer (NSCLC) in a subject, the method comprising administering to the subject in need of the treatment a therapeutically effective amount of Erlotinib or Gefitinib in combination with at least one of Compound (I), Compound (II), Compound (III), or combinations thereof, wherein Compound (I), Compound (II), or Compound (III) is present in a crystalline form. In another aspect of this disclosure, this method of treatment may be practiced by administering a pharmaceutical composition of at least one of Compound (I), Compound (II), Compound (III) or combinations thereof such as discussed above. In another embodiment, the combination administered in this method is Erlotinib with at least one of Compound (I), Compound (II), Compound (III), or combinations thereof.

Another aspect of this disclosure relates to a method of treating an astrocytic tumor (which includes glioblastoma, giant cell glioblastoma, gliosarcoma, and glioblastoma with oligodendroglial components in a subject) in a subject, the method comprising administering to the subject in need of the treatment a therapeutically effective amount of N-(4-{[6,7-bis(methyloxy)quinolin-4-yl]oxy}phenyl)-N'-(4-fluorophenyl)cyclopropane-1,1-dicarboxamide.

Another aspect of this disclosure relates to a method of treating an astrocytic tumor (which includes glioblastoma, giant cell glioblastoma, gliosarcoma, and glioblastoma with oligodendroglial components in a subject) in a subject, the method comprising administering to the subject in need of the treatment a therapeutically effective amount of at least one of Compound (I), Compound (II), Compound (III) or combinations thereof. Compound (I), Compound (II), or Compound (III) may be individually administered as one of the solid state forms discussed above or combinations thereof. The crystalline forms are preferred solid state forms. Accordingly another aspect of this disclosure relates to a method of treating an astrocytic tumor comprising administering to a subject in need thereof a therapeutically effective amount of at least one of Compound (I), Compound (II), Compound (III), or combinations thereof, wherein Compound (I), Compound (II), or Compound (III) is present in a crystalline form. In another aspect of this disclosure, this method of treatment may be practiced by administering a pharmaceutical composition of at least one of Compound (I), Compound (II), Compound (III) or combinations thereof such as discussed above.

Another aspect of this disclosure relates to a method of treating thyroid cancer (including medullary thyroid cancer) in a subject, the method comprising administering to the subject in need of the treatment N-(4-{[6,7-bis(methyloxy)quinolin-4-yl]oxy}phenyl)-N'-(4-fluorophenyl)cyclopropane-1,1-dicarboxamide, or a pharmaceutically acceptable salt thereof. The amount administered can be a therapeutically effective amount.

Another aspect of this disclosure relates to a method of treating thyroid cancer (including medullary thyroid cancer) in a subject, the method comprising administering to the subject in need of the treatment at least one of Compound (I), Compound (II), Compound (III) or combinations thereof. Compound (I), Compound (II), or Compound (III) may be individually administered as one of the solid state forms discussed above or combinations thereof. The crystalline forms are preferred solid state forms. Accordingly another aspect of this disclosure relates to a method of treating thyroid cancer comprising administering to a subject in need thereof a therapeutically effective amount of at least one of Compound (I), Compound (II), Compound (III), or combinations thereof, wherein Compound (I), Compound (II), or Compound (III) is present in a crystalline form. In another aspect of this disclosure, this method of treatment may be practiced by administering a pharmaceutical composition of at least one of Compound (I), Compound (II), Compound (III) or combinations thereof such as discussed above.

Another aspect of this disclosure relates to a method of treating diseases or disorders associated with uncontrolled, abnormal, and/or unwanted cellular activities. This method administers, to a subject in need thereof, at least one of Compound (I), Compound (II), Compound (III) or combinations thereof. The amount of Compound (I), Compound (II), or combinations thereof administered can be a therapeutically effective amount. Compound (I), Compound (II), or Compound (III) may be individually administered as one of the solid state forms discussed above or combinations thereof. The crystalline forms are preferred solid state forms.

Accordingly another aspect of this disclosure relates to a method of treating diseases or disorders associated with uncontrolled, abnormal, and/or unwanted cellular activities comprising administering to a subject in need thereof a therapeutically effective amount of at least one of Compound (I), Compound (II), Compound (III), or combinations thereof, wherein Compound (I), Compound (II), or Compound (III) is present in a crystalline form. In another aspect of this disclosure, this method of treatment may be practiced by administering a pharmaceutical composition of at least one of Compound (I), Compound (U), Compound (III) or combinations thereof such as discussed above. Another aspect of this disclosure relates to a method of treating diseases or disorders associated with uncontrolled, abnormal, and/or unwanted cellular activities. This method administers, to a subject in need thereof, a crystalline form of Compound (I), Compound (II), or any combination of Compound (I) and (II). The amount of Compound (I), Compound (II), or any combination of Compound (I) and (II) administered can be a therapeutically effective amount.

Another aspect of this disclosure relates to a use of the N-(4-{[6,7-bis(methyloxy)quinolin-4-yl]oxy}phenyl)-N'-(4-fluorophenyl) cyclopropane-1,1-dicarboxamide, malate salt according to any of the above embodiments for the manufacture of a medicament for the treatment of a disease or disorder discussed above. When dissolved, a crystalline or amorphous form according to this disclosure loses its solid state structure, and is therefore referred to as a solution of, for example, Compound (I). At least one crystalline form disclosed herein may be used to prepare at least one liquid formulation in which at least one crystalline form according to the disclosure is dissolved and/or suspended.

A pharmaceutical composition such as discussed above may be any pharmaceutical form which contains active Compound (I), Compound (II) and/or Compound (III), including the solid state forms thereof (hereinafter referred to as active compound(s). The pharmaceutical composition may be, for example, a tablet, capsule, liquid suspension, injectable, topical, or transdermal. The pharmaceutical compositions generally contain about 1% to about 99% by weight of the active compound(s), or a crystalline form of the active compound(s), and 99% to 1% by weight of a suitable pharmaceutical excipient. In one example, the composition will be between about 5% and about 75% by weight of active compound, with the rest being suitable pharmaceutical excipients or other adjuvants, as discussed below.

A "therapeutically effective amount of the active compounds, or a crystalline or amorphous form of the active compound(s), according to this disclosure to inhibit, regulate and/or modulate the signal transduction of kinases (discussed here concerning the pharmaceutical compositions)

refers to an amount sufficient to treat a patient suffering from any of a variety of cancers associated with abnormal cell proliferation and angiogenesis. A therapeutically effective amount according to this disclosure is an amount therapeutically useful for the treatment or prevention of the disease states and disorders discussed herein. Compounds (I), (II), and/or (III) (including their solid state forms), possess therapeutic activity to inhibit, regulate and/or modulate the signal transduction of kinases such as described in WO2005-030140. N-(4-{[6,7-bis(methyloxy)quinolin-4-yl]oxy}phenyl)-N'-(4-fluorophenyl)-cyclopropane-1,1-dicarboxamide.

The actual amount required for treatment of any particular patient will depend upon a variety of factors including the disease state being treated and its severity; the specific pharmaceutical composition employed; the age, body weight, general health, sex and diet of the patient; the mode of administration; the time of administration; the route of administration; and the rate of excretion of the active compound(s), or a crystalline form of the active compound(s), according to this disclosure; the duration of the treatment; any drugs used in combination or coincidental with the specific compound employed; and other such factors well known in the medical arts. These factors are discussed in Goodman and Gilman's "The Pharmacological Basis of Therapeutics", Tenth Edition, A. Gilman, J. Hardman and L. Limbird, eds., McGraw-Hill Press, 155-173, 2001, which is incorporated herein by reference. The active compound(s), or a crystalline form of active compound(s), according to this disclosure and pharmaceutical compositions comprising them, may be used in combination with anticancer or other agents that are generally administered to a patient being treated for cancer. They may also be co-formulated with one or more of such agents in a single pharmaceutical composition.

Depending on the type of pharmaceutical composition, the pharmaceutically acceptable carrier may be chosen from any one or a combination of carriers known in the art. The choice of the pharmaceutically acceptable carrier depends partly upon the desired method of administration to be used. For a pharmaceutical composition of this disclosure, that is, one of the active compound(s), or a crystalline form of the active compound(s), of this disclosure, a carrier should be chosen so as to substantially maintain the particular form of the active compound(s), whether it would be crystalline or not. In other words, the carrier should not substantially alter the form the active compound(s) are. Nor should the carrier be otherwise incompatible with the form of the active compound(s), such as by producing any undesirable biological effect or otherwise interacting in a deleterious manner with any other component(s) of the pharmaceutical composition.

The pharmaceutical compositions of this disclosure may be prepared by methods know in the pharmaceutical formulation art, for example, see Remington's Pharmaceutical Sciences, 18th Ed., (Mack Publishing Company, Easton, Pa., 1990). In a solid dosage forms Compound (I) is admixed with at least one pharmaceutically acceptable excipient such as sodium citrate or dicalcium phosphate or (a) fillers or extenders, as for example, starches, lactose, sucrose, glucose, mannitol, and silicic acid, (b) binders, as for example, cellulose derivatives, starch, alginates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Pharmaceutically acceptable adjuvants known in the pharmaceutical formulation art may also be used in the pharmaceutical compositions of this disclosure. These include, but are not limited to, preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. If desired, a pharmaceutical composition of this disclosure may also contain minor amounts of auxiliary substances such as wetting or emulsifying agents, pH buffering agents, and antioxidants, such as, for example, citric acid, sorbitan monolaurate, triethanolamine oleate, and butylated hydroxytoluene.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the active compound(s), or a crystalline form of the active compound(s), with, for example, suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Because the active compound(s), or a crystalline form of the active compound(s), is maintained during their preparation, solid dosage forms are preferred for the pharmaceutical composition of this disclosure. Solid dosage forms for oral administration, which includes capsules, tablets, pills, powders, and granules, are particularly preferred. In such solid dosage forms, the active compound(s) mixed with at least one inert, pharmaceutically acceptable excipient (also known as a pharmaceutically acceptable carrier). Administration of the active compound(s), or a crystalline form of the active compound(s), in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages. One preferable route of administration is oral administration, using a convenient dosage regimen that can be adjusted according to the degree of severity of the disease-state to be treated.

General Preparation Methods of Crystalline Forms

Crystalline forms may be prepared by a variety of methods including, but not limited to, for example, crystallization or recrystallization from a suitable solvent mixture; sublimation; growth from a melt; solid state transformation from another phase; crystallization from a supercritical fluid; and jet spraying. Techniques for crystallization or recrystallization of crystalline forms of a solvent mixture include, but are not limited to, for example, evaporation of the solvent; decreasing the temperature of the solvent mixture; crystal seeding of a supersaturated solvent mixture of the compound and/or salt thereof; crystal seeding a supersaturated solvent mixture of the compound and/or a salt from thereof; freeze drying the solvent mixture; and adding antisolvents (countersolvents) to the solvent mixture. High throughput crystallization techniques may be employed to prepare crystalline forms including polymorphs.

Crystals of drugs, including polymorphs, methods of preparation, and characterization of drug crystals are discussed in *Solid-State Chemistry of Drugs*, S. R. Byrn, R. R. Pfeiffer, and J. G. Stowell, $2^{nd}$ Edition, SSCI, West Lafayette, Ind. (1999).

In a crystallization technique in which solvent is employed, the solvent(s) are typically chosen based on one or more factors including, but not limited to, for example, solubility of the compound; crystallization technique utilized; and vapor pressure of the solvent. Combinations of solvents may be employed. For example, the compound may be solubilized in a first solvent to afford a solution to which antisolvent is then added to decrease the solubility of the Compound (I) in the solution and precipitate the formation of crystals. An antisolvent is a solvent in which a compound has low solubility.

In one method that can be used in preparing crystals, Compound (I), Compound (II) and/or Compound (III) can be suspended and/or stirred in a suitable solvent to afford a slurry, which may be heated to promote dissolution. The term "slurry", as used herein, means a saturated solution of the compound, wherein such solution may contain an additional amount of compound to afford a heterogeneous mixture of compound and solvent at a given temperature.

Seed crystals may be added to any crystallization mixture to promote crystallization. Seeding may be employed to control growth of a particular polymorph and/or to control the particle size distribution of the crystalline product. Accordingly, calculation of the amount of seeds needed depends on the size of the seed available and the desired size of an average product particle as described, for example, in Programmed Cooling Batch Crystallizers," J. W. Mullin and J. Nyvlt, Chemical Engineering Science, 1971, 26, 3690377. In general, seeds of small size are needed to effectively control the growth of crystals in the batch. Seeds of small size may be generated by sieving, milling, or micronizing large crystals, or by microcrystallizing a solution. In the milling or micronizing of crystals, care should be taken to avoid changing crystallinity from the desired crystalline form (i.e., changing to an amorphous or other polymorphic form).

A cooled crystallization mixture may be filtered under vacuum and the isolated solid product washed with a suitable solvent, such as, for example, cold recrystallization solvent. After being washed, the product may be dried under a nitrogen purge to afford the desired crystalline form. The product may be analyzed by a suitable spectroscopic or analytical technique including, but not limited to, for example, differential scanning calorimetry (DSC); x-ray powder diffraction (XRPD); and thermogravimetric analysis (TGA) to assure the crystalline form of the compound has been formed. The resulting crystalline form may be produced in an amount greater than about 70 wt. % isolated yield, based on the weight of the compound originally employed in the crystallization procedure, and preferably greater than about 90 wt. % isolated yield. Optionally, the product may be delumped by being comilled or passed through mesh screen.

The features and advantages of this disclosure may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of this disclosure that are, for brevity reasons, described in the context of a single embodiment, may also be combined so as to form sub-combinations thereof. The disclosure is further illustrated by the following examples, which are not to be construed as limiting the disclosure in scope or spirit to the specific procedures described in them.

The definitions set forth herein take precedence over definitions set forth in any patent, patent application, and/or patent application publication incorporated herein by reference. All measurements are subject to experimental error and are within the spirit of the invention.

As used herein, "amorphous" refers to a solid form of a molecule and/or ion that is not crystalline. An amorphous solid does not display a definitive X-ray diffraction pattern with sharp maxima.

As used herein, the term "substantially pure" means the crystalline form of Compound (I) referred to contains at least about 90 wt. % based on the weight of such crystalline form. The term "at least about 90 wt. %," while not intending to limit the applicability of the doctrine of equivalents to the scope of the claims, includes, but is not limited to, for example, about 90, about 91, about 92, about 93, about 94, about 95, about 96, about 97, about 98, about 99 and about 100% wt. %, based on the weight of the crystalline form referred to. The remainder of the crystalline form of Compound (I) may comprise other Form(s) of Compound (I) and/or reaction impurities and/or processing impurities that arise, for example, when the crystalline form is prepared. The presence of reaction impurities and/or processing impurities may be determined by analytical techniques known in the art, such as, for example, chromatography, nuclear magnetic resonance spectroscopy, mass spectroscopy, and/or infrared spectroscopy.

PREPARATIVE EXAMPLES

Example 1: Preparation of N-(4-{[6,7-bis(methyloxy)quinolin-4-yl]oxy}phenyl)-N'-(4-fluorophenyl)cyclopropane-1,1-dicarboxamide and the (L)-malate salt thereof (Compound (I))

The synthetic route used for the preparation of N-(4-{[6,7-bis(methyloxy)quinolin-4-yl]oxy}phenyl)-N'-(4-fluorophenyl)cyclopropane-1,1-dicarboxamide and the (L)-malate salt thereof is depicted in Scheme 1:

SCHEME 1

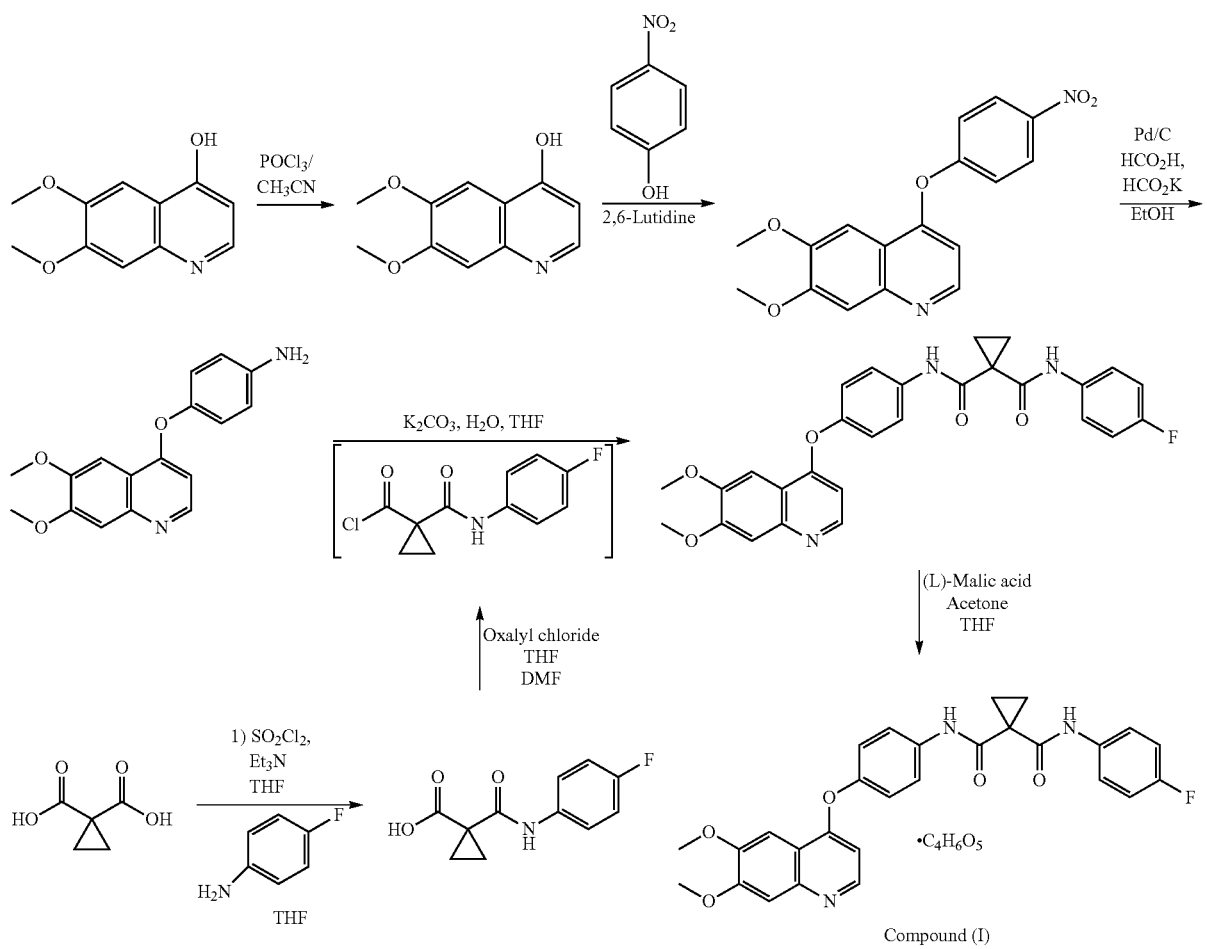

The process shown in Scheme 1 is described in more detail below.

1.1 Preparation of 4-Chloro-6,7-dimethoxy-quinoline

A reactor was charged sequentially with 6,7-dimethoxy-quinoline-4-ol (1 L, 10.0 kg) and acetonitrile (64.0 L). The resulting mixture was heated to approximately 65° C. and phosphorus oxychloride (POCl$_3$, 50.0 kg) was added. After the addition of POCl$_3$, the temperature of the reaction mixture was raised to approximately 80° C. The reaction was deemed complete (approximately 9.0 hours) when <2% of the starting material remained (in process high-performance liquid chromatography [HPLC] analysis). The reaction mixture was cooled to approximately 10° C. and then quenched into a chilled solution of dichloromethane (DCM, 238.0 kg), 30% NH$_4$OH (135.0 kg), and ice (440.0 kg). The resulting mixture was warmed to approximately 14° C., and phases were separated. The organic phase was washed with water (40.0 kg) and concentrated by vacuum distillation with the removal of solvent (approximately 190.0 kg). Methyl-t-butyl ether (MTBE, 50.0 kg) was added to the batch, and the mixture was cooled to approximately 10° C., during which time the product crystallized out. The solids were recovered by centrifugation, washed with n-heptane (20.0 kg), and dried at approximately 40° C. to afford the title compound (8.0 kg).

1.2 Preparation of 6,7-Dimethyl-4-(4-nitro-phenoxy)-quinoline

A reactor was sequentially charged with 4-chloro-6,7-dimethoxy-quinoline (8.0 kg), 4 nitrophenol (7.0 kg), 4 dimethylaminopyridine (0.9 kg), and 2,6 lutidine (40.0 kg). The reactor contents were heated to approximately 147° C. When the reaction was complete (<5% starting material remaining as determined by in process HPLC analysis, approximately 20 hours), the reactor contents were allowed to cool to approximately 25° C. Methanol (26.0 kg) was added, followed by potassium carbonate (3.0 kg) dissolved in water (50.0 kg). The reactor contents were stirred for approximately 2 hours. The resulting solid precipitate was filtered, washed with water (67.0 kg), and dried at 25° C. for approximately 12 hours to afford the title compound (4.0 kg).

1.3 Preparation of 4-(6,7-Dimethoxy-quinoline-4-yloxy)-phenylamine

A solution containing potassium formate (5.0 kg), formic acid (3.0 kg), and water (16.0 kg) was added to a mixture of 6,7-dimethoxy-4-(4-nitro-phenoxy)-quinoline (4.0 kg), 10% palladium on carbon (50% water wet, 0.4 kg) in tetrahydrofuran (40.0 kg) that had been heated to approximately 60° C. The addition was carried out such that the temperature of the reaction mixture remained approximately 60° C. When the reaction was deemed complete as determined using in-process HPLC analysis (<2% starting material remaining, typically 15 hours), the reactor contents were filtered. The filtrate was concentrated by vacuum distillation at approximately 35° C. to half of its original volume, which resulted in the precipitation of the product. The product was recovered by filtration, washed with water (12.0 kg), and dried under vacuum at approximately 50° C. to afford the title compound (3.0 kg; 97% AUC).

1.4 Preparation of 1-(4-Fluoro-phenylcarbamoyl)-cyclopropanecarboxylic acid

Triethylamine (8.0 kg) was added to a cooled (approximately 4° C.) solution of commercially available cyclopropane-1,1-dicarboxylic acid (2 1, 10.0 kg) in THF (63.0 kg) at a rate such that the batch temperature did not exceed 10° C. The solution was stirred for approximately 30 minutes, and then thionyl chloride (9.0 kg) was added, keeping the batch temperature below 10° C. When the addition was complete, a solution of 4-fluoroaniline (9.0 kg) in THF (25.0 kg) was added at a rate such that the batch temperature did not exceed 10° C. The mixture was stirred for approximately 4 hours and then diluted with isopropyl acetate (87.0 kg). This solution was washed sequentially with aqueous sodium hydroxide (2.0 kg dissolved in 50.0 L of water), water (40.0 L), and aqueous sodium chloride (10.0 kg dissolved in 40.0 L of water). The organic solution was concentrated by vacuum distillation followed by the addition of heptane, which resulted in the precipitation of solid. The solid was recovered by centrifugation and then dried at approximately 35° C. under vacuum to afford the title compound. (10.0 kg).

1.5 Preparation of 1-(4-Fluoro-phenylcarbamoyl)-cyclopropanecarbonyl chloride Oxalyl chloride (1.0 kg) was added to a solution of 1-(4-fluoro-phenylcarbamoyl)-cyclopropanecarboxylic acid (2.0 kg) in a mixture of THF (11 kg) and N, N-dimethylformamide (DMF; 0.02 kg) at a rate such that the batch temperature did not exceed 30° C. This solution was used in the next step without further processing.

1.6 Preparation of N-(4-{[6,7-bis(methyloxy)quinolin-4-yl]oxy}phenyl)-N'-(4-fluorophenyl)cyclopropane-1,1-dicarboxamide The solution from the previous step containing 1-(4-fluoro-phenylcarbamoyl)-cyclopropanecarbonyl chloride was added to a mixture of 4-(6,7-dimethoxy-quinoline-4-yloxy)-phenylamine (3.0 kg) and potassium carbonate (4.0 kg) in THF (27.0 kg) and water (13.0 kg) at a rate such that the batch temperature did not exceed 30° C. When the reaction was complete (in typically 10 minutes), water (74.0 kg) was added. The mixture was stirred at 15-30° C. for approximately 10 hours, which resulted in the precipitation of the product. The product was recovered by filtration, washed with a premade solution of THF (11.0 kg) and water (24.0 kg), and dried at approximately 65° C. under vacuum for approximately 12 hours to afford the title compound (free base, 5.0 kg). $^1$H NMR (400 MHz, d$_6$-DMSO): δ 10.2 (s, 1H), 10.05 (s, 1H), 8.4 (s, 1H), 7.8 (m, 2H), 7.65 (m, 2H), 7.5 (s, 1H), 7.35 (s, 1H), 7.25 (m, 2H), 7.15 (m, 2H), 6.4 (s, 1H), 4.0 (d, 6H), 1.5 (s, 4H). LCMS: M+H=502.

1.7 Preparation of N-(4-{[6,7-bis(methyloxy)quinolin-4-yl]oxy}phenyl)-N'-(4-fluorophenyl)cyclopropane-1,1-dicarboxamide, (L) malate salt (Compound (I))

A solution of (L)-malic acid (2.0 kg) in water (2.0 kg) was added to a solution of Cyclopropane-1,1-dicarboxylic acid [4-(6,7-dimethoxy-quinoline-4-yloxy)-phenyl]-amide (4-fluoro-phenyl)-amide free base (15, 5.0 kg) in ethanol, maintaining a batch temperature of approximately 25° C. Carbon (0.5 kg) and thiol silica (0.1 kg) were then added, and the resulting mixture was heated to approximately 78° C., at which point water (6.0 kg) was added. The reaction mixture was then filtered, followed by the addition of isopropanol (38.0 kg), and was allowed to cool to approximately 25° C. The product was recovered by filtration and washed with isopropanol (20.0 kg) and dried at approximately 65° C. to afford Compound (I) (5.0 kg).

Example 2: Preparation of Crystalline Compound (I), Form N-1

A solution was prepared by adding tetrahydrofuran (12 mL/g-bulk-LR (limiting reagent); 1.20 L) and N-(4-{[6,7-bis(methyloxy)-quinolin-4-yl]oxy}phenyl)-N'-(4-fluorophenyl)cyclopropane-1,1-dicarboxamide, (100 g; 1.00 equiv; 100.00 g) and (L)-malic acid (1.2 equiv (molar); 32.08 g) to a 1 L reactor. Water (0.5317 mL/g-bulk-LR; 53.17 mL) was added and the solution was heated to 60° C. and maintained at that temperature for one hour until the solids were fully dissolved. The solution was passed through a Polish Filter.

At 60° C., acetonitrile (12 mL/g-bulk-LR; 1.20 L) was added over a period of 8 hours. The solution was held at 60° C. for 10 hours. The solution was then cooled to 20° C. and held for 1 hour. The solids were filtered and washed with acetonitrile (12 mL/g-bulk-LR; 1.20 L). The solids were dried at 60° C. (25 mm Hg) for 6 hours to afford Compound (I), Form N-1 (108 g; 0.85 equiv; 108.00 g; 85.22% yield) as a white crystalline solid.

Example 3: Alternate Preparation of Crystalline Compound (I), Form N-1

A solution was prepared with 190 mL tetrahydrofuran (110 mL), methyl isobutyl ketone, and 29 mL water. Next, 20 mL of this solution were transferred into an amber bottle, and then saturated by adding N-(4-{[6,7-bis(methyloxy)-quinolin-4-yl]oxy}phenyl)-N'-(4-fluorophenyl)cyclopropane-1,1-dicarboxamide, (L)-malate until a thick slurry formed, and aging for at least 2 h with stirring at room temperature. The solids were removed by filtration through a Buchner funnel, rendering a clear saturated solution.

Separately, a powder blend was made with known amounts of two batches of Compound (I): (1) 300 mg of batch 1, which contained approximately 41% Compound (I), Form N-1 and 59% Compound (I), Form N-2 by Raman spectroscopy analysis, and (2) 200 mg of batch 2, which had a XPRD pattern similar to Compound (I), Form N-2.

The Compound (I), Form N-1 and Compound (I), Form N-2 powder blend was added into the saturated solution, and the slurry was aged under magnetic stirring at room temperature for 25 days. The slurry was then sampled and filtered through a Buchner funnel to obtain 162 mg of wet cake. The wet cake was dried in a vacuum oven at 45° C. to afford 128 mg of crystalline Compound (I) in the N-1 form.

Example 4: Preparation of Crystalline Compound (I), Form N-2

4.1 Preparation of Crystalline Compound (I), Form N-2 Seed Crystals

A solution was prepared by combining 20 ml of acetone and 300 mg of freebase N-(4-{[6,7-bis(methyloxy)quinolin-4-yl]oxy}phenyl)-N'-(4-fluorophenyl)cyclopropane-1,1-dicarboxamide in a 25 ml screw capped vial. Next, 0.758 ml of a 0.79M (L)-malic acid stock solution was added to the vial with magnetic stirring. The solution was then left stirring for 24 hr at ambient temperature. The sample was then suction filtered with 0.45 μm PTFE filter cartridge and dried in vacuo at ambient temperature overnight.

4.2 Preparation of Crystalline Compound (I), Form N-2

To a reactor were added N-(4-{[6,7-bis(methyloxy)-quinolin-4-yl]oxy}phenyl)-N'-(4-fluorophenyl)cyclopropane-1,1-dicarboxamide (48 g; 1.00 equiv; 48.00 g) and tetrahydrofuran (16.5 mL/g-bulk-LR; 792.00 mL). The water content was adjusted to 1 wt % water. The solution was heated to 60° C. Once dissolved, the solution was passed through a polish filter to provide the first solution.

In a separate reactor, (L)-malic acid (1.2 equiv (molar); 15.40 g) was dissolved into methyl isobutyl ketone (10 mL/g-bulk-LR; 480.00 mL) and tetrahydrofuran (1 mL/g-bulk-LR; 48.00 mL). Next, 50 mL of the (L)-malic acid solution was added to the first solution at 50° C. Seed crystals were added (1% 480 mg) and the malic acid solution was added at 50° C. dropwise via an addition funnel (1.3 ml/min (3 h)). The slurry was held at 50° C. for 18 h and then was cooled to 25° C. over 30 min. The solids were filtered, and washed with 20% tetrahydrofuran/methyl isobutyl ketone (10V, 480 ml.). The solids were dried under vacuum at 60° C. for 5 h to afford Compound (I) (55.7 g; 0.92 equiv; 55.70 g; 91.56% yield) as an off-white crystalline solid.

Example 5: Preparation of Crystalline Compound (III), Form N-1

A one ml aliquot (DL)-malic acid salt of N-(4-{[6,7-bis(methyloxy)-quinolin-4-yl]oxy}phenyl)-N'-(4-fluorophenyl)cyclopropane-1,1-dicarboxamide, slurried in tetrahydrofuran (THF), was heated to 60° C. on a hot-plate in a half-dram vial. Next, tetrahydrofuran was added drop-wise until an almost clear solution was obtained. The vial was capped, removed from the hot plate and equilibrated at ambient temperature without agitation. Crystallization was apparent after several hours and the solution was allowed to stand overnight to allow completion. Several droplets of the resulting slurry were placed on a glass slide for microscopic analysis. The crystalline material consisted of many elongated plates ranging up to 60 microns in the longest dimension.

Alternate Preparation of Crystalline Compound (III), Form N-1

To a reactor were added N-(4-{[6,7-bis(methyloxy)-quinolin-4-yl]oxy}phenyl)-N'-(4-fluorophenyl)cyclopropane-1,1-dicarboxamide (15 g; 1.00 equiv; 15.00 g) and tetrahydrofuran (16.5 mL/g-bulk-LR; 792.00 mL). The water content was adjusted to 1 wt % water. The solution was heated to 60° C. Once dissolved, the solution was passed through a polish filter to provide the first solution.

In a separate reactor, (DL)-malic acid (1.2 equiv (molar); 4.53 g) was dissolved into methyl isobutyl ketone (8 mL/g-bulk-LR; 120.00 mL) and tetrahydrofuran (1 mL/g-bulk-LR; 15.00 mL). Next, 20 mL of the solution was added to the first solution at 50° C. The malic acid solution was added at 50° C. dropwise via an addition funnel (1.3 ml/min (3 h)). The slurry was held at 50° C. for 18 h and then was cooled to 25° C. over 30 min. The solids were filtered, and washed with 20% THF/MIBK (0V, 150 mL). The solids were dried under vacuum at 60° C. for 5 h to afford Compound (III) (15.52 g; 86.68% yield) as an off-white solid.

Example 6: Preparation of Amorphous Compound (I)

A solution was prepared with 5 g of N-(4-{[6,7-bis(methyloxy)quinolin-4-yl]oxy}phenyl)-N'-(4-fluorophenyl)cyclopropane-1,1-dicarboxamide, (L)-malate and 250 mL of a 1:1 (v:v) mixture of methanol and dichloromethane. The hazy solution was filtered through a 0.45 micron filter to yield a clear, yellowish solution. The solution was pumped through the spray dryer nozzle at a rate of 12.9 cc/min, and was atomized by nitrogen gas fed at a rate of 10.911 min. The temperature at the inlet of the cyclone was set to 65° C. to dry the wet droplets. Dry amorphous powder (1.5 g) was collected (yield=30%).

CHARACTERIZATION EXAMPLES

I. NMR Spectra in Dimethyl Sulfoxide Solution

I.1 Compound (I), Form N-1

$^1$H NMR (400 MHz, d$_6$-DMSO): δ 1.48 (s, 1H), 2.42-2.48 (m, 1H), 2.60-2.65 (m. 1H), 3.93-3.96 (m, 6H), 4.25-4.30 (dd, 1H, J=5, 8 Hz), 6.44 (d, 1H, J=5 Hz, 1H), 7.12-7.19 (m, 2H), 7.22-7.26 (m, 2H), 7.40 (s, 1H), 7.51 (s, 1H), 7.63-7.68 (m, 2H), 7.76-7.80 (m, 2H), 8.46-8.49 (m, 1H), 10.08 (s, 1H), 10.21 (s, 1H).

$^{13}$C NMR (d$_6$-DMSO): 15.36, 31.55, 55.64, 55.67, 66.91, 99.03, 102.95, 107.66, 114.89, 115.07, 115.11, 121.17, 122.11, 122.32, 122.39, 135.15, 136.41, 146.25, 148.7, 149.28, 149.38, 152.54, 157.03, 159.42, 160.02, 168.07, 171.83, 174.68.

I.2 Compound (I), Form N-2

$^1$H NMR (400 MHz, d$_6$-DMSO): δ 1.48 (s, 1H), 2.42-2.48 (m, 1H), 2.60-2.65 (m, 1H), 3.93-3.96 (m, 6H), 4.25-4.30 (dd, 1H, J=5, 8 Hz), 6.44 (d, J=5 Hz, 1H), 7.12-7.19 (m, 2H), 7.22-7.26 (m, 2H), 7.40 (s, 1H), 7.51 (s, 1H), 7.63-7.68 (m, 2H), 7.76-7.80 (m, 2H), 8.46-8.49 (m, 1H), 10.08 (s, 1H), 10.21 (s, 1H).

$^{13}$C NMR (d$_6$-DMSO): 15.36, 31.55, 55.64, 55.67, 66.91, 99.03, 102.95, 107.66, 114.89, 115.07, 115.11, 121.17, 122.11, 122.32, 122.39, 135.15, 136.41, 146.25, 148.7, 149.28, 149.38, 152.54, 157.03, 159.42, 160.02, 168.07, 171.83, 174.68.

I.3 Compound (III), Form N-1

$^1$H NMR (400 MHz, d$_6$-DMSO): δ 1.48 (s, 1H), 2.42-2.48 (m, 1H), 2.60-2.65 (m, 1H), 3.93-3.96 (m, 6H), 4.25-4.30 (dd, 1H, J=5, 8 Hz), 6.44 (d, J=5 Hz, 1H), 7.12-7.19 (m, 2H), 7.22-7.26 (m, 2H), 7.40 (s, 1H), 7.51 (s, 1H), 7.63-7.68 (m, 2H), 7.76-7.80 (m, 2 II), 8.46-8.49 (m, 1H), 10.08 (s, 1H), 10.21 (s, 1H).

$^{13}$C NMR (d$_6$-DMSO): 15.36, 31.55, 55.64, 55.67, 66.91, 99.03, 102.95, 107.66, 114.89, 115.07, 115.11, 121.17, 122.11, 122.32, 122.39, 135.15, 136.41, 146.25, 148.7, 149.28, 149.38, 152.54, 157.03, 159.42, 160.02, 168.07, 171.83, 174.68.

Characterization of Solid State Forms of N-(4-{[6,7-bis (methyloxy)quinolin-4-yl]oxy}phenyl)-N'-(4-fluorophenyl) cyclopropane-1,1-dicarboxamide, malate II. Powder X-Ray Diffraction (XRPD) Studies X-Ray Powder Diffraction (XRPD) patterns were collected on a Bruker AXS C2 GADDS diffractometer equipped with an automated XYZ stage, laser video microscope for auto-sample positioning and a HiStar 2-dimensional area detector. The radiation source used was copper (Cu Kα=1.5406 Å), wherein the voltage was set at 40 kV and the current was set at 40 mA, X-ray optics consists of a single Göbel multilayer mirror coupled with a pinhole collimator of 0.3 mm. The beam divergence, i.e. the effective size of the X-ray beam on the sample, was approximately 4 mm. A θ-θ continuous scan mode was employed with a sample-detector distance of 20 cm which gives an effective 2θ range of 3.2°-29.8°. Samples run under ambient conditions (from about 18° C. to about 25° C.) were prepared as flat plate specimens using powder as received without grinding. Approximately 1-2 mg of the sample was lightly pressed on a glass slide to obtain a flat surface. Typically the sample would be exposed to the X-ray beam for 120 seconds. Beam divergence (i.e., effective size of X-ray spot, gives a value of approximately 4 mm. Alternatively, the powder samples were placed in sealed glass capillaries of 1 mm or less in diameter; the capillary was rotated during data collection at a sample-detector distance of 15 cm. Data were collected for 3≤2θ≤35° with a sample exposure time of at least 2000 seconds. The resulting two-dimensional diffraction arcs were integrated to create a traditional 1-dimensional XRPD pattern with a step size of 0.02 °2θ in the range of 3 to 35 °2θ±0.2 °2θ. The software used for data collection was GADDS for WNT 4.1.16 and the data were analyzed and presented using Diffrac Plus EVA v 9.0.0.2 or v 13.0.0.2.

II.1 Compound (I), Form N-1

FIG. 1 shows the experimental XRPD pattern of crystalline Compound (I), Form N-1 acquired at room temperature (about 25° C.). A list of the peaks are shown in Table 2, above. The 2θ values at 19.4, 21.5, 22.8, 25.1, and 27.6 (±0.2 °2θ) are useful for characterizing crystalline Compound (I), Form N-1. The entire list of peaks, or a subset thereof, may be sufficient to characterize crystalline Compound (I), Form N-1.

II.2 Compound (I), Form N-2

Figure 8:
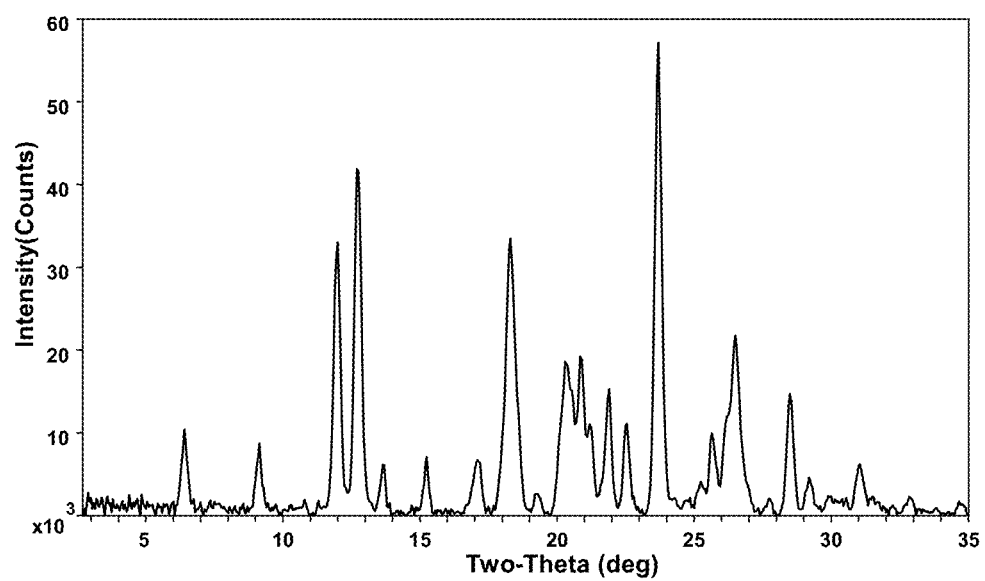
FIG. 8 shows the experimental XRPD pattern for crystalline Compound (I), Form N-2 at 25° C.

FIG. 8 shows the experimental XRPD pattern of crystalline Compound (I), Form N-2 acquired at room temperature (about 25° C.). A list of the peaks are shown in Table 2, above. The 2θ values at 20.9 and 21.9 (±0.2 °2θ) are useful for characterizing crystalline Compound (I), Form N-2. The entire list of peaks, or a subset thereof, may be sufficient to characterize crystalline Compound (I), Form N-2.

II.3 Compound (III), Form N-1

Figure 15:
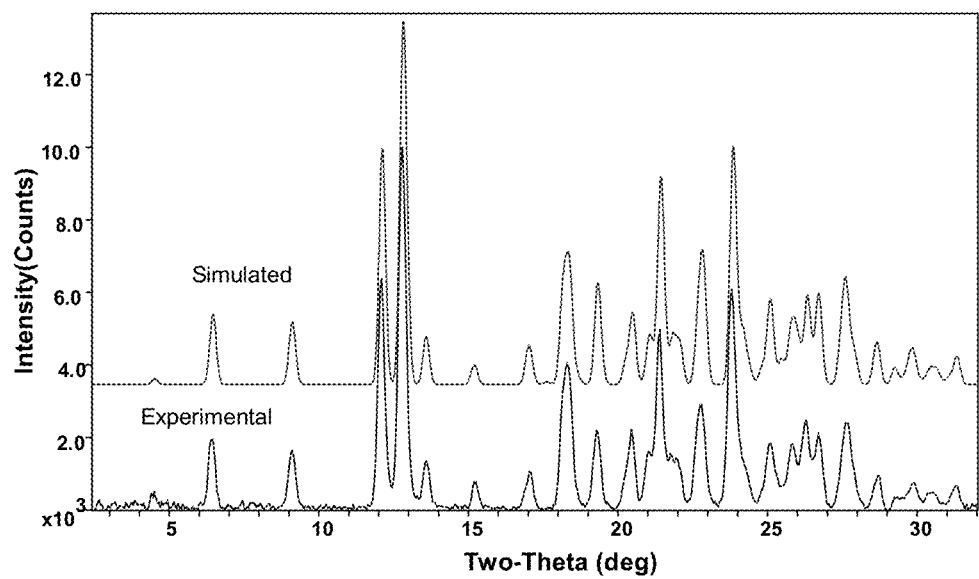
FIG. 15 shows the experimental and simulated XRPD patterns for crystalline Compound (III), Form N-1 at room temperature.

FIG. 15 shows the experimental and the simulated XRPD pattern of crystalline Compound (III), Form N-1, acquired at 25° C. using a spinning capillary sample. A list of the peaks are shown in Table 2, above. The entire list of peaks, or a subset thereof, may be sufficient to characterize crystalline Compound (III), Form N-2.

II.4 Amorphous Compound (I)

Figure 22:
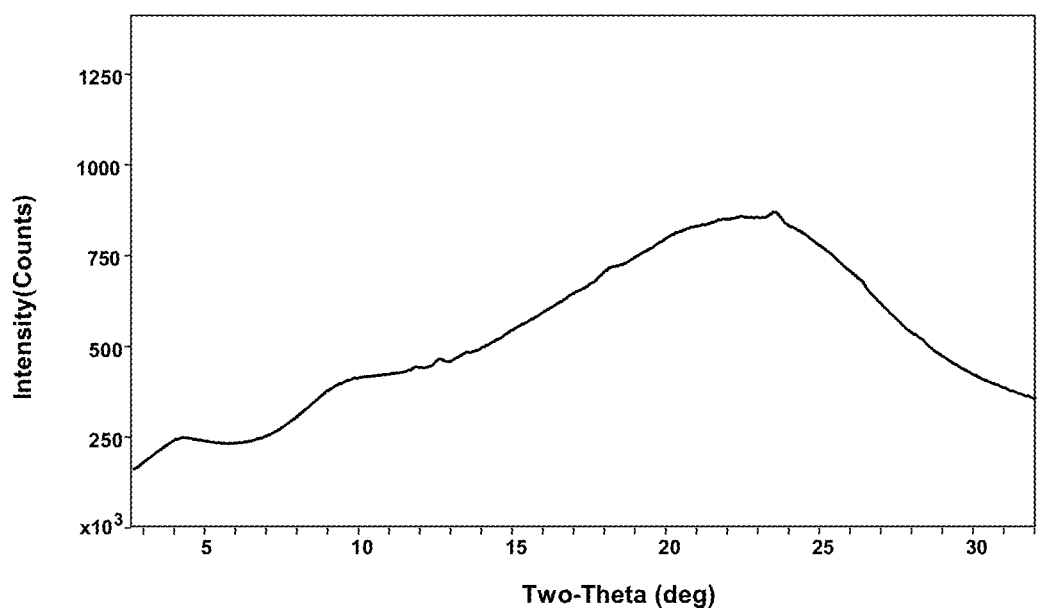
FIG. 22 shows the XRPD pattern of amorphous Compound (I) at room temperature.

FIG. 22 shows the experimental XRPD pattern of amorphous Compound (I) acquired at room temperature (about 25° C.). The spectra is characterized a broad peak and the absence of sharp peaks, which is consistent with an amorphous material.

III. Single Crystal X-Ray Study for Compound (III), Form N-1

Data were collected on a Bruker-Nonius CAD4 serial diffractometer. Unit cell parameters were obtained through least-squares analysis of the experimental diffractometer settings of 25 high-angle reflections. Intensities were measured using Cu Kα radiation (λ=1.5418 Å) at a constant temperature with the θ-2θ variable scan technique and were corrected only for Lorentz-polarization factors. Background counts were collected at the extremes of the scan for half of the time of the scan. Alternately, single crystal data were collected on a Bruker-Nonius Kappa CCD 2000 system using Cu Kα radiation (λ=1.5418 Å). Indexing and processing of the measured intensity data were carried out with the HKL2000 software package (Otwinowski, Z. & Minor, W. (1997) in *Macromolecular Crystallography*, eds. Carter, W. C. Jr & Sweet, R. M. (Academic, NY), Vol. 276, pp. 307-326) in the Collect program suite (Collect Data collection and processing user interface: Collect: Data collection software, R. Hooft, Nonius B. V., 1998). Alternately, single crystal data were collected on a Bruker-AXS APEX2 CCD system using Cu Kα radiation (λ=1.5418 Å). Indexing and processing of the measured intensity data were carried out with the APEX2 software package/program suite (APEX2 Data collection and processing user interface: APEX2 User Manual, v1.27). When indicated, crystals were cooled in the cold stream of an Oxford cryo system (Oxford Cryosystems Cryostream cooler J. Cosier and A. M. Glazer, J. Appl. Cryst., 1986, 19, 105) during data collection.

The structures were solved by direct methods and refined on the basis of observed reflections using either the SDP software package (SDP, Structure Determination Package, Enraf-Nonius, Bohemia N.Y. 11716. Scattering factors, including f' and f", in the SDP software were taken from the "International Tables for Crystallography", Kynoch Press, Birmingham, England, 1974; Vol IV, Tables 2.2A and 2.3.1) with minor local modifications or the crystallographic packages MAXUS (maXus solution and refinement software suite: S. Mackay, C. J. Gilmore, C. Edwards, M. Tremayne, N. Stewart, K. Shankland. maXus: a computer program for the solution and refinement of crystal structures from diffraction data) or SHELXTL (APEX2 Data collection and processing user interface: APEX2 User Manual, v1.27).

The derived atomic parameters (coordinates and temperature factors) were refined through full matrix least-squares. The function minimized in the refinements was $\Sigma_w(|F_o|-|F_c|)^2$. R is defined as $\Sigma||F_o|-|F_c||/\Sigma|F_o|$ while $R_w = [\Sigma_w(|F_o|-|F_c|)^2/\Sigma_w|F_o|^2]^{1/2}$ where w is an appropriate weighting function based on errors in the observed intensities. Difference maps were examined at all stages of refinement. Hydrogens were introduced in idealized positions with isotropic temperature factors, but no hydrogen parameters were varied.

"Hybrid" simulated powder X-ray patterns were generated as described in the literature (Yin. S.; Scaringe, R. P.; DiMarco, J.; Galella, M. and Gougoutas, J. Z., *American Pharmaceutical Review*, 2003, 6, 2, 80). The room temperature cell parameters were obtained by performing a cell refinement using the CellRefine.xls program. Input to the program includes the 2-theta position of ca. 10 reflections, obtained from the experimental room temperature powder pattern; the corresponding Miller indices, hkl, were assigned based on the single-crystal data collected at low temperature. A new (hybrid) XRPD was calculated (by either of the software programs, Alex or LatticeView) by inserting the molecular structure determined at low temperature into the room temperature cell obtained in the first step of the procedure. The molecules are inserted in a manner that retains the size and shape of the molecule and the position of the molecules with respect to the cell origin, but, allows intermolecular distances to expand with the cell.

A single crystal, measuring 40×30×10 microns, was selected from the slurry of crystals described in Example 5 for single crystal diffraction analysis. The selected crystal was affixed to a thin glass fiber with a small amount of a light grease, and mounted at room temperature on a Bruker ApexII single crystal diffractometer equipped with a rotating copper anode.

Crystalline Compound (III), From N-1 is characterized by unit cell parameters approximately equal to those reported in Table 4. The unit cell parameters were measured at a temperature of about 25° C.

TABLE 4 a = 14.60 Å
b = 5.20 Å
c = 39.09 Å
α = 90.0°
β = 90.4°
γ = 90.0°
Space group: P2$_1$/n
Molecules of Compound (I)/unit cell: 4
Volume = 2969 Å$^3$ Structure solution and refinement were routine in the monoclinic space group, P2$_1$/n, with four formula units in the unit cell. The structure contains cations of N-(4-{[6,7-bis(methyloxy)-quinolin-4-yl]oxy}phenyl)-N'-(4-fluoro-phenyl)cyclopropane-1,1-dicarboxamide, protonated at the quinoline nitrogen atom, and singly ionized malic acid anions, in a 1:1 ratio. Further, the crystal contained a 1:1 ratio of (L)-malic acid ions to (D)-malic acid ions. Table 5 fractional atomic coordinates for Compound (III), Form N-1 calculated at a temperature of about 25° C.

Based on the single crystal X-ray data, crystalline Compound (III), Form N-1 may be characterized by a simulated powder x-ray diffraction (XRPD) pattern substantially in accordance with the simulated pattern shown in FIG. 15 and/or by an observed XRPD pattern substantially in accordance with the experimental pattern shown in FIG. 15.

TABLE 5

Fractional Atomic Coordinates for Compound (III), Form N-1
Calculated at a Temperature of about 25° C.

| Atom | X | Y | Z |
|---|---|---|---|
| O1 | 0.30601 | −0.52166 | 0.22875 |
| O2 | 0.29518 | 0.12504 | 0.09391 |
| O3 | 0.19041 | −0.53232 | 0.18147 |
| F5 | −0.07307 | 2.12170 | −0.08811 |
| O6 | 0.18186 | 1.20500 | −0.03241 |
| O7 | 0.57137 | 0.22739 | 0.23473 |
| O8 | 0.58700 | −0.17911 | 0.24998 |
| O9 | 0.41742 | 0.76377 | −0.04319 |
| N10 | 0.28649 | 0.82210 | −0.01420 |
| O11 | 0.87391 | 0.22086 | 0.31241 |
| N12 | 0.46887 | 0.17029 | 0.17613 |
| C13 | 0.29647 | 0.64886 | 0.01247 |
| C14 | 0.31416 | 1.08187 | −0.06304 |
| C15 | 0.33900 | −0.02207 | 0.14761 |
| N16 | 0.20651 | 1.40640 | −0.08267 |
| C17 | 0.40079 | −0.01723 | 0.17602 |
| C18 | 0.29743 | 0.29956 | 0.06604 |
| C19 | 0.00418 | 1.80556 | −0.05680 |

TABLE 5-continued

Fractional Atomic Coordinates for Compound (III), Form N-1
Calculated at a Temperature of about 25° C.

| Atom | X | Y | Z |
|---|---|---|---|
| C20 | 0.11925 | 1.73626 | −0.11097 |
| C21 | 0.22556 | 1.24019 | −0.05791 |
| C22 | 0.39150 | −0.17467 | 0.20389 |
| C23 | 0.22558 | 0.63870 | 0.03619 |
| O24 | 0.62714 | 0.39565 | 0.29760 |
| C25 | 0.34591 | 0.87438 | −0.03961 |
| C26 | 0.36467 | −0.51389 | 0.25773 |
| C27 | 0.26562 | −0.20277 | 0.14859 |
| C28 | 0.35380 | 0.15272 | 0.12054 |
| C29 | 0.07365 | 1.60604 | −0.05443 |
| C30 | 0.04897 | 1.92890 | −0.11212 |
| C31 | 0.73841 | 0.04517 | 0.28641 |
| C32 | 0.32089 | −0.35160 | 0.20385 |
| C33 | 0.36641 | 0.29052 | 0.04302 |
| C34 | 0.42458 | 0.32272 | 0.12143 |
| C35 | 0.11723 | −0.54030 | 0.15742 |
| C36 | 0.12933 | 1.59042 | −0.08228 |
| C37 | −0.00344 | 1.93494 | −0.08547 |
| C38 | 0.36439 | 0.47245 | 0.01586 |
| C39 | 0.59040 | 0.05797 | 0.25625 |
| C40 | 0.25712 | −0.35516 | 0.17574 |
| C41 | 0.63543 | 0.13842 | 0.29041 |
| C42 | 0.22703 | 0.46640 | 0.06306 |
| C43 | 0.34559 | 1.01717 | −0.10021 |
| C44 | 0.39312 | 1.20834 | −0.08137 |
| C45 | 0.48224 | 0.32340 | 0.15059 |
| O46 | 0.77400 | 0.04784 | 0.34652 |
| C47 | 0.79349 | 0.09920 | 0.31966 |
| H10 | 0.22646 | 0.91057 | −0.01479 |
| H16 | 0.24790 | 1.42164 | −0.10317 |
| H19 | −0.04176 | 1.82973 | −0.03893 |
| H20 | 0.16347 | 1.73025 | −0.13083 |
| H22 | 0.43179 | −0.17902 | 0.22447 |
| H23 | 0.17093 | 0.73524 | 0.03244 |
| H27 | 0.21953 | −0.24212 | 0.12962 |
| H29 | 0.07954 | 1.50390 | −0.03492 |
| H30 | 0.04671 | 2.05817 | −0.13354 |
| H33 | 0.41851 | 0.16255 | 0.04395 |
| H34 | 0.43433 | 0.41859 | 0.10106 |
| H38 | 0.41440 | 0.45648 | −0.00227 |
| H41 | 0.61062 | 0.02238 | 0.31086 |
| H42 | 0.17752 | 0.45794 | 0.07911 |
| H45 | 0.53033 | 0.44239 | 0.15049 |
| H31a | 0.76754 | 0.12071 | 0.26693 |
| H31b | 0.74726 | −0.15247 | 0.28137 |
| H43a | 0.30237 | 1.06909 | −0.12187 |
| H43b | 0.36868 | 0.85693 | −0.10836 |
| H44a | 0.45563 | 1.18725 | −0.07495 |
| H44b | 0.38932 | 1.39942 | −0.08846 |
| H26a | 0.35958 | −0.37184 | 0.27147 |
| H26b | 0.42813 | −0.55605 | 0.25348 |
| H26c | 0.34954 | −0.66814 | 0.27571 |
| H35a | 0.08189 | −0.39941 | 0.15398 |
| H35b | 0.06671 | −0.68838 | 0.16269 |
| H35c | 0.13276 | −0.61095 | 0.13323 |
| H11 | 0.88836 | 0.21926 | 0.28968 |
| H12 | 0.50720 | 0.16494 | 0.19477 |
| H24 | 0.61522 | 0.45898 | 0.27789 |

IV. Solid State Nuclear Magnetic Resonance (SSNMR)

All solid-state C-13 NMR measurements were made with a Bruker DSX-400, 400 MHz NMR spectrometer. High resolution spectra were obtained using high-power proton decoupling and the TPPM pulse sequence and ramp amplitude cross-polarization (RAMP-CP) with magic-angle spinning (MAS) at approximately 12 kHz (A. E. Bennett et al, *J. Chem. Phys.*, 1995, 103, 6951), (G. Metz, X. Wu and S. O. Smith, *J. Magn. Reson. A.*, 1994, 110, 219-227). Approximately 70 mg of sample, packed into a canister-design zirconia rotor was used for each experiment. Chemical shifts (δ) were referenced to external adamantane with the high frequency resonance being set to 38.56 ppm (W. L Earl and D. L VanderHart, *J. Magn. Reson.*, 1982, 48, 35-54).

IV.1 Compound (I), Form N-1

Figure 2:
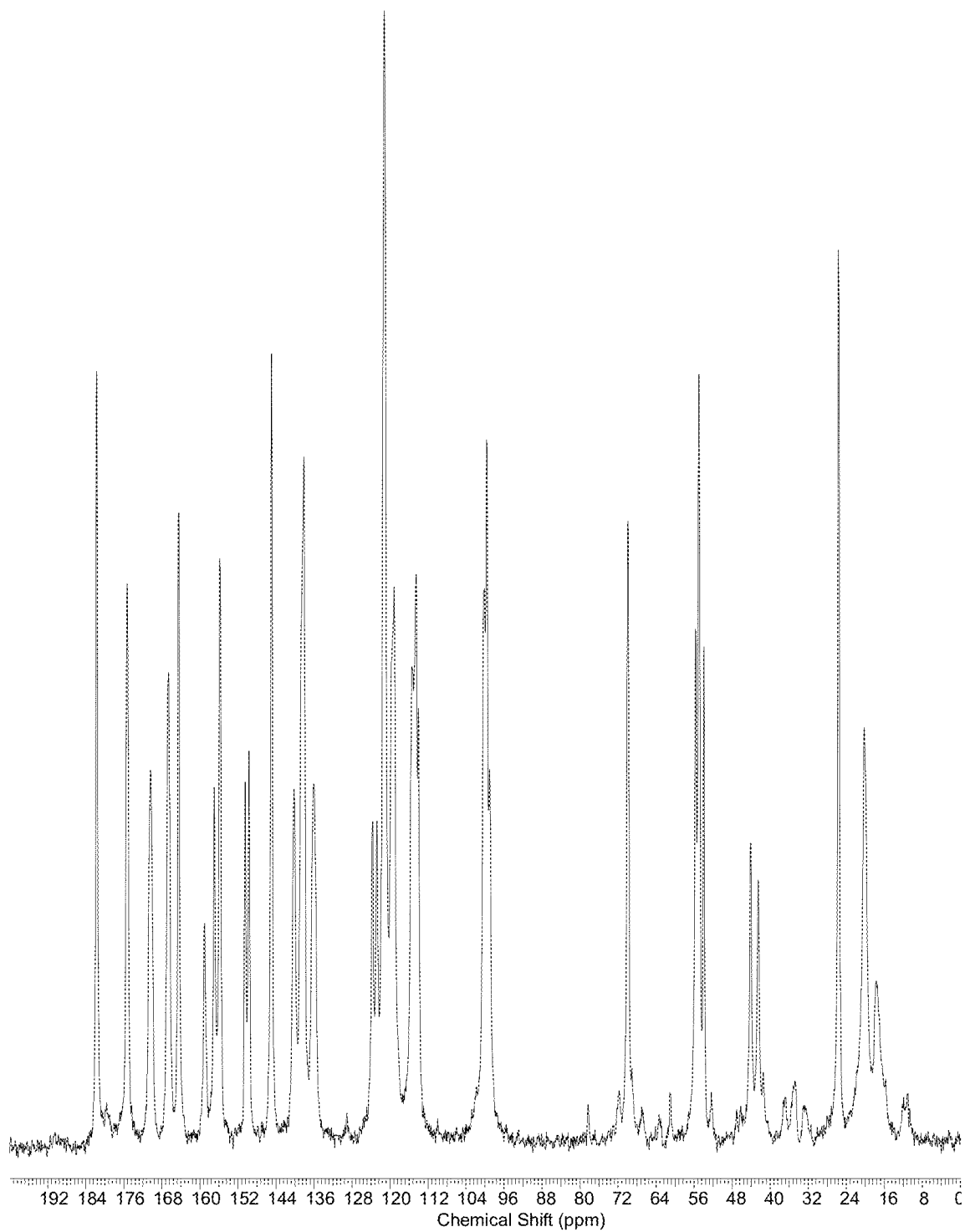
FIG. 2 shows the solid state $^{13}$C NMR spectrum of crystalline Compound (I), Form N-1.

The solid state $^{13}$C NMR spectrum of crystalline Compound (I), Form N-1 is shown in FIG. 2. The entire list of peaks, or a subset thereof, may be sufficient to characterize crystalline Compound (I), Form N-1.

SS $^{13}$C NMR Peaks: 18.1, 20.6, 26.0, 42.9, 44.5, 54.4, 55.4, 56.1, 70.4, 99.4, 100.1, 100.6, 114.4, 114.9, 115.8, 119.6, 120.1, 121.6, 123.2, 124.1, 136.4, 138.6, 140.6, 145.4, 150.1, 150.9, 156.2, 157.4, 159.4, 164.9, 167.1, 170.8, 175.7, and 182.1 ppm, ±0.2 ppm.

Figure 3:
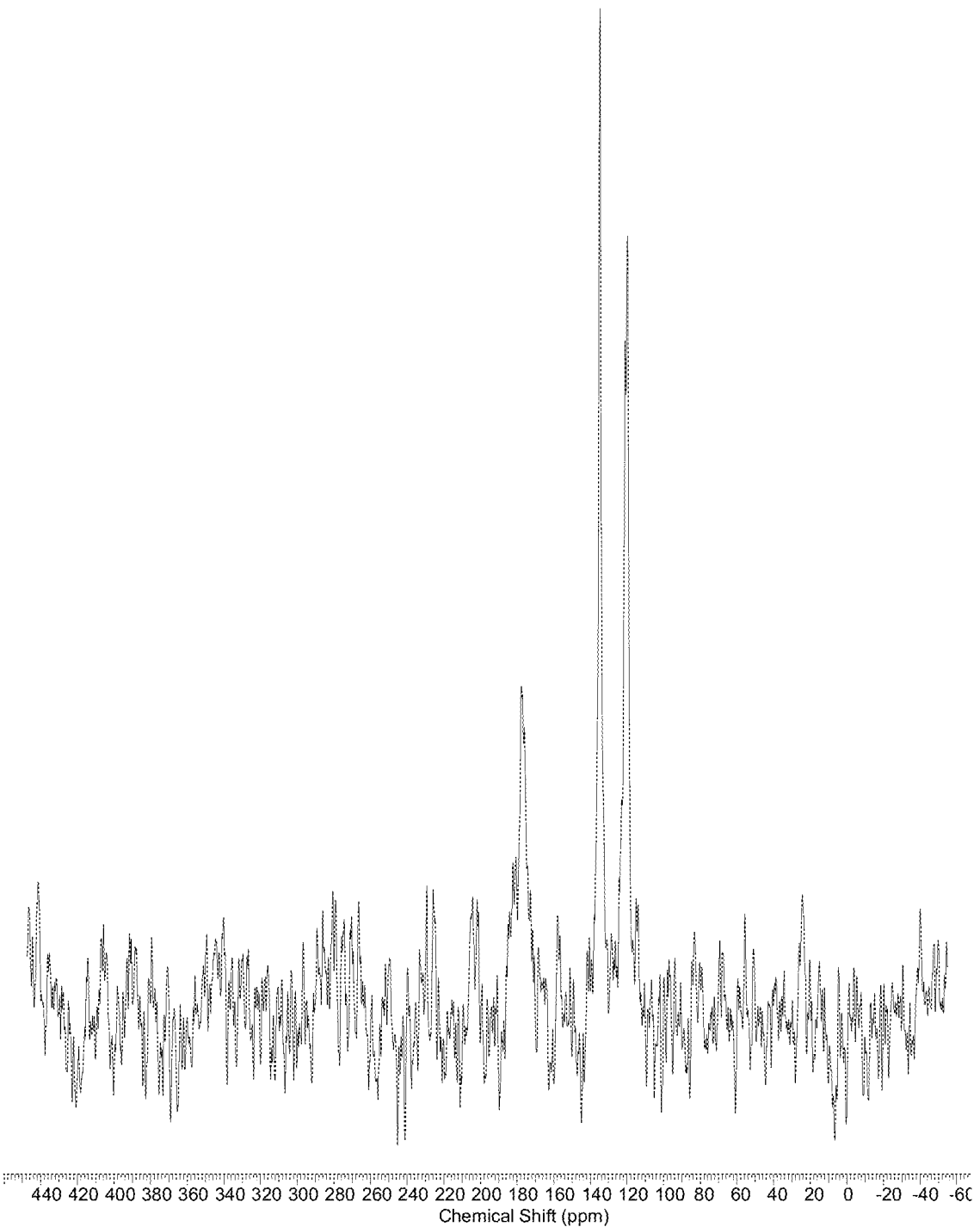
FIG. 3 shows the solid state $^{15}$N NMR spectrum of crystalline Compound (I), Form N-1.

FIG. 3 shows the solid state $^{15}$N NMR spectrum of crystalline Compound (I), Form N-1. The spectrum shows peaks at 118.6, 119.6, 120.7, 134.8, 167.1, 176.0, and 180 ppm, ±0.2 ppm. The entire list of peaks, or a subset thereof, may be sufficient to characterize crystalline Compound (I), Form N-1.

Figure 4:
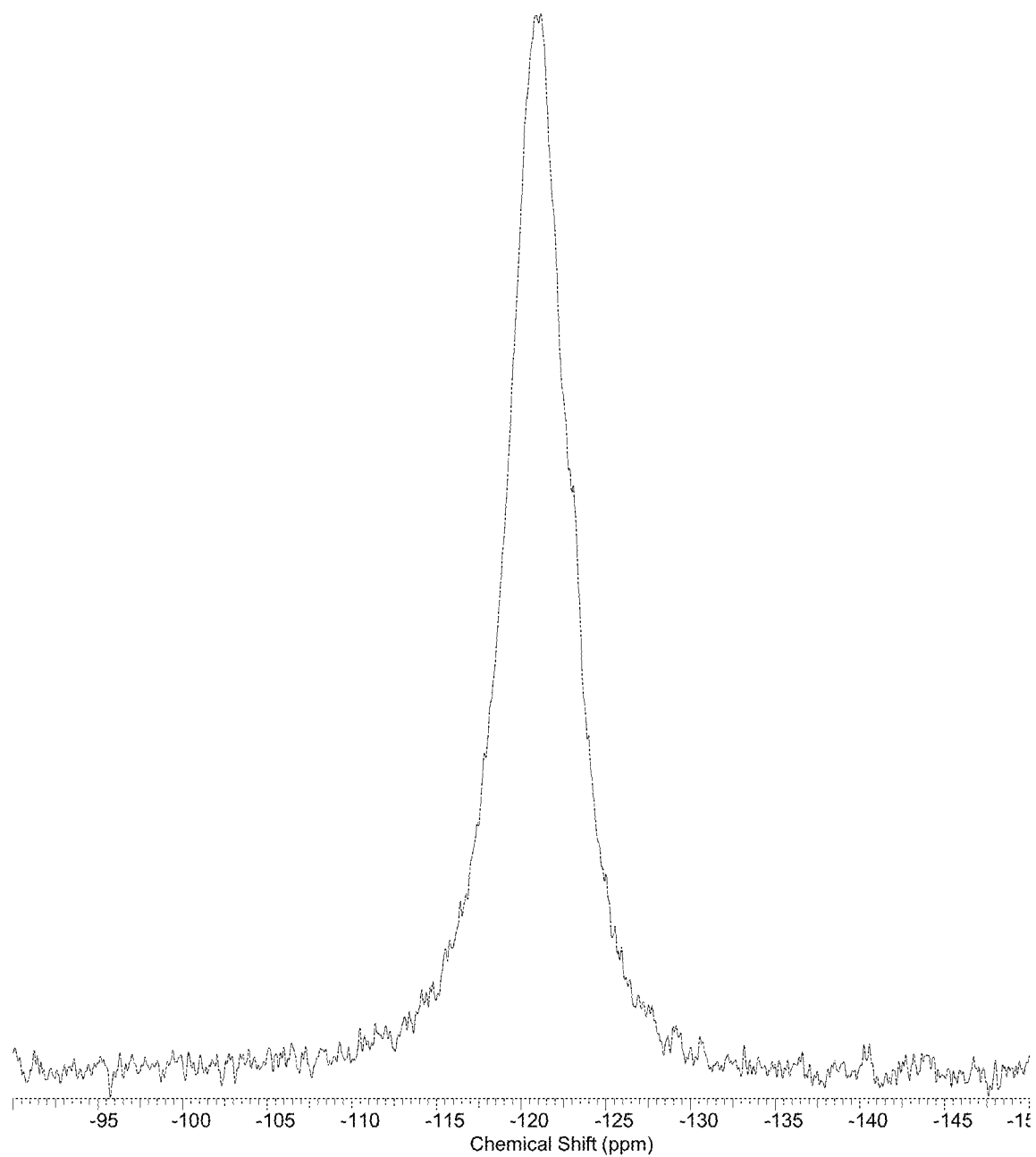
FIG. 4 shows the solid state $^{19}$F NMR spectrum of crystalline Compound (I), Form N-1.

FIG. 4 shows the solid state $^{19}$F NMR spectrum of crystalline Compound (I), Form N-1. The spectrum shows a peak at −121.6, −120.8, and −118.0 ppm, ±0.2 ppm.

IV.2 Compound (I), Form N-2

Figure 9:
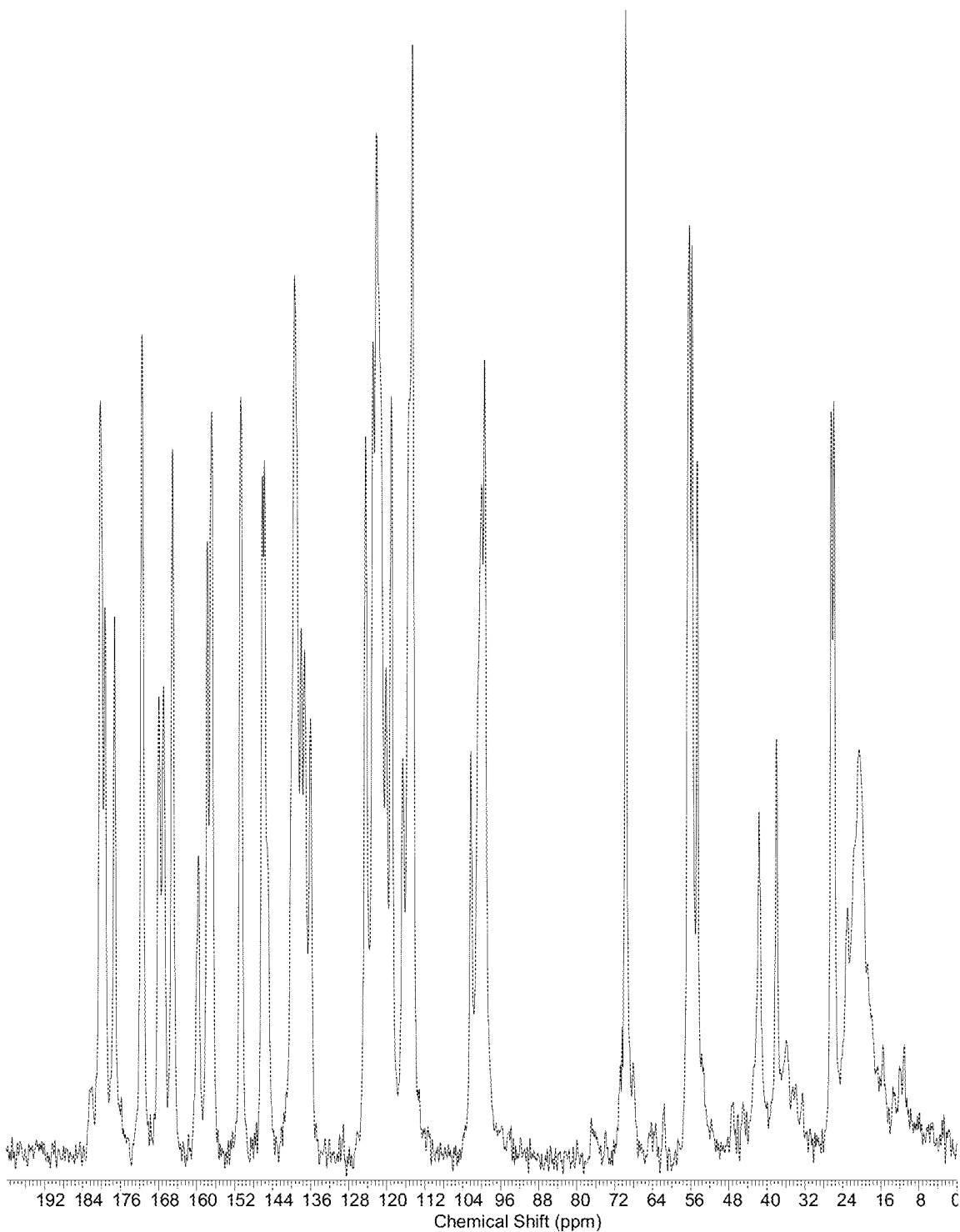
FIG. 9 shows the solid state $^{13}$C NMR spectrum of crystalline Compound (I), Form N-2.

The solid state $^{13}$C NMR spectrum of crystalline Compound (I), Form N-2 is shown in FIG. 9. The entire list of peaks, or a subset thereof, may be sufficient to characterize crystalline Compound (I), Form N-2.

SS $^{13}$C NMR Peaks: 20.5, 21.8, 23.0, 25.9, 26.4, 38.0, 41.7, 54.7, 55.8, 56.2, 56.6, 69.7, 99.4, 100.0, 100.4, 100.8, 102.3, 114.5, 115.5, 116.7, 119.0, 120.2, 121.1, 121.2, 122.1, 122.9, 124.5, 136.0, 137.3, 138.1, 138.9, 139.5, 140.2, 144.9, 145.7, 146.1, 150.7, 156.7, 157.7, 159.6, 159.7, 165.1, 167.0, 168.0, 171.5, 177.3, 179.3, 180.0, and 180.3 ppm, ±0.2 ppm.

Figure 10:
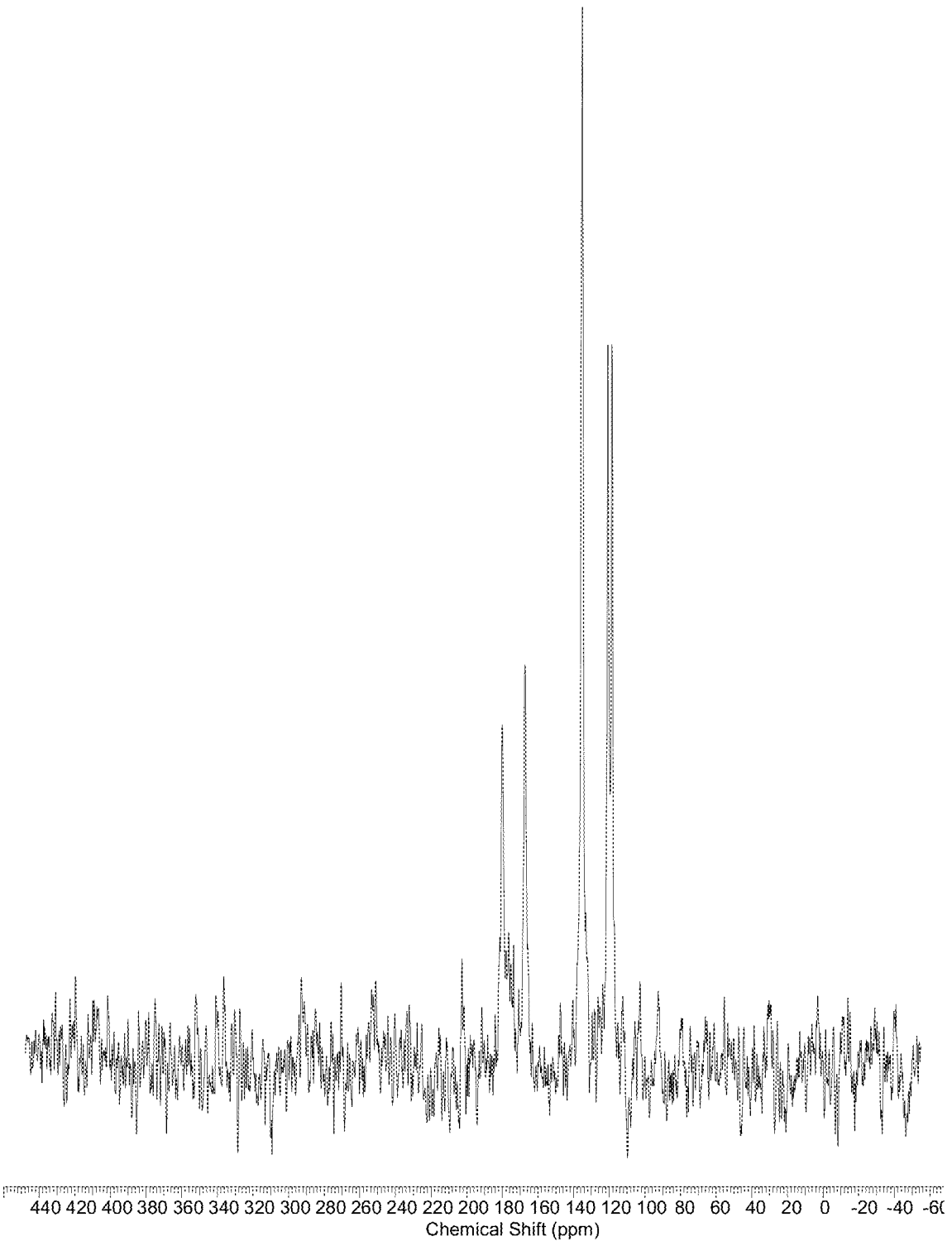
FIG. 10 shows the solid state $^{15}$N NMR spectrum of crystalline Compound (I), Form N-2.

FIG. 10 shows the solid state $^{15}$N NMR spectrum of crystalline Compound (I), Form N-2. The spectrum shows peaks at 118.5, 120.8, 135.1, 167.3, and 180.1 ppm, ±0.2 ppm. The entire list of peaks, or a subset thereof, may be sufficient to characterize crystalline Compound (I), Form N-2.

Figure 11:
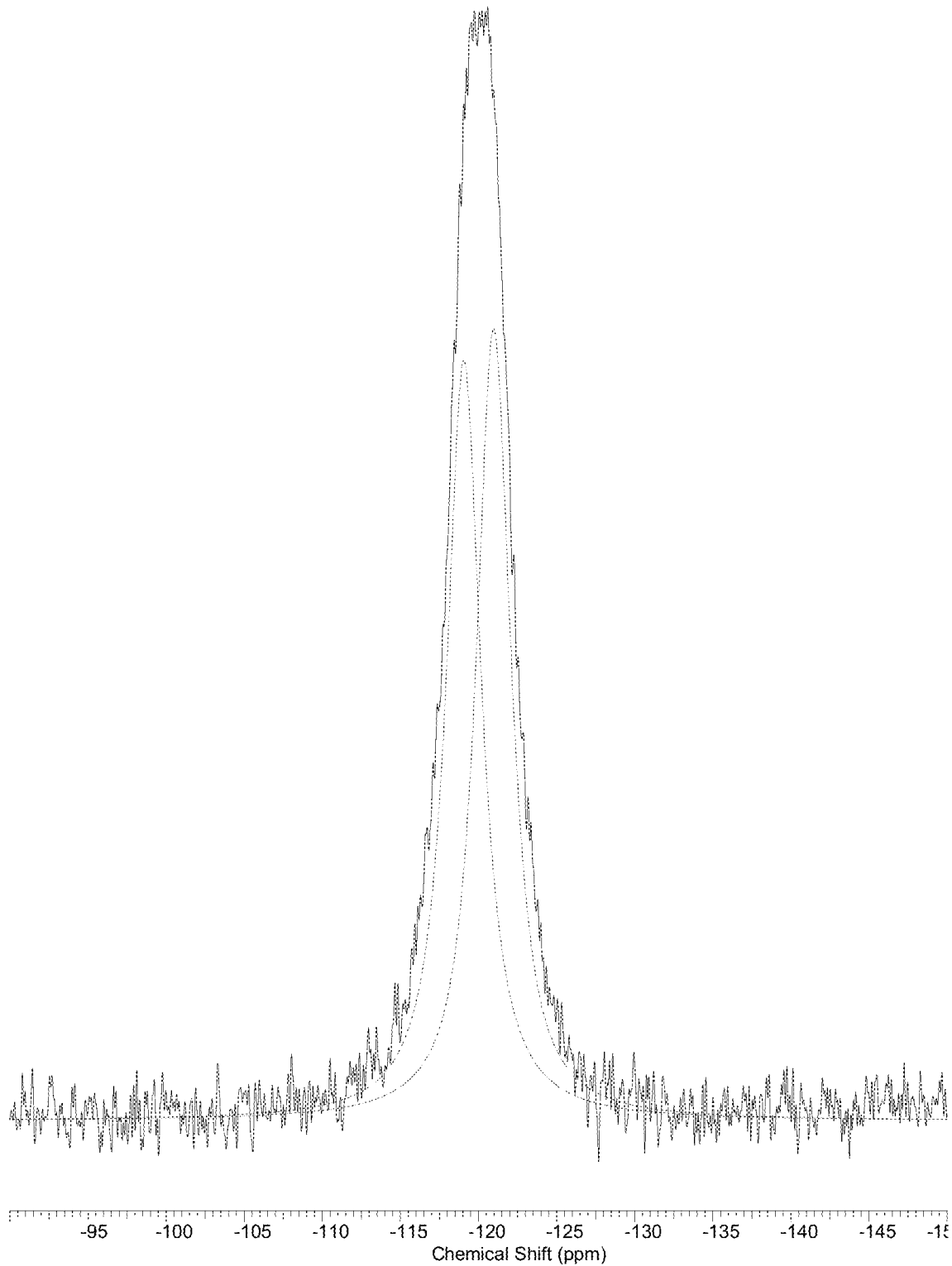
FIG. 11 shows the solid state $^{19}$F NMR spectrum of crystalline Compound (I), Form N-2.

FIG. 11 shows the solid state $^{19}$F NMR spectrum of crystalline Compound (I), Form N-2. The spectrum shows peaks at −121.0 and −119.1 ppm, ±0.2 ppm. Those peaks, individually or together, may be sufficient to characterize crystalline Compound (I), Form N-2.

IV.3 Compound (III), Form N-1

Figure 16:
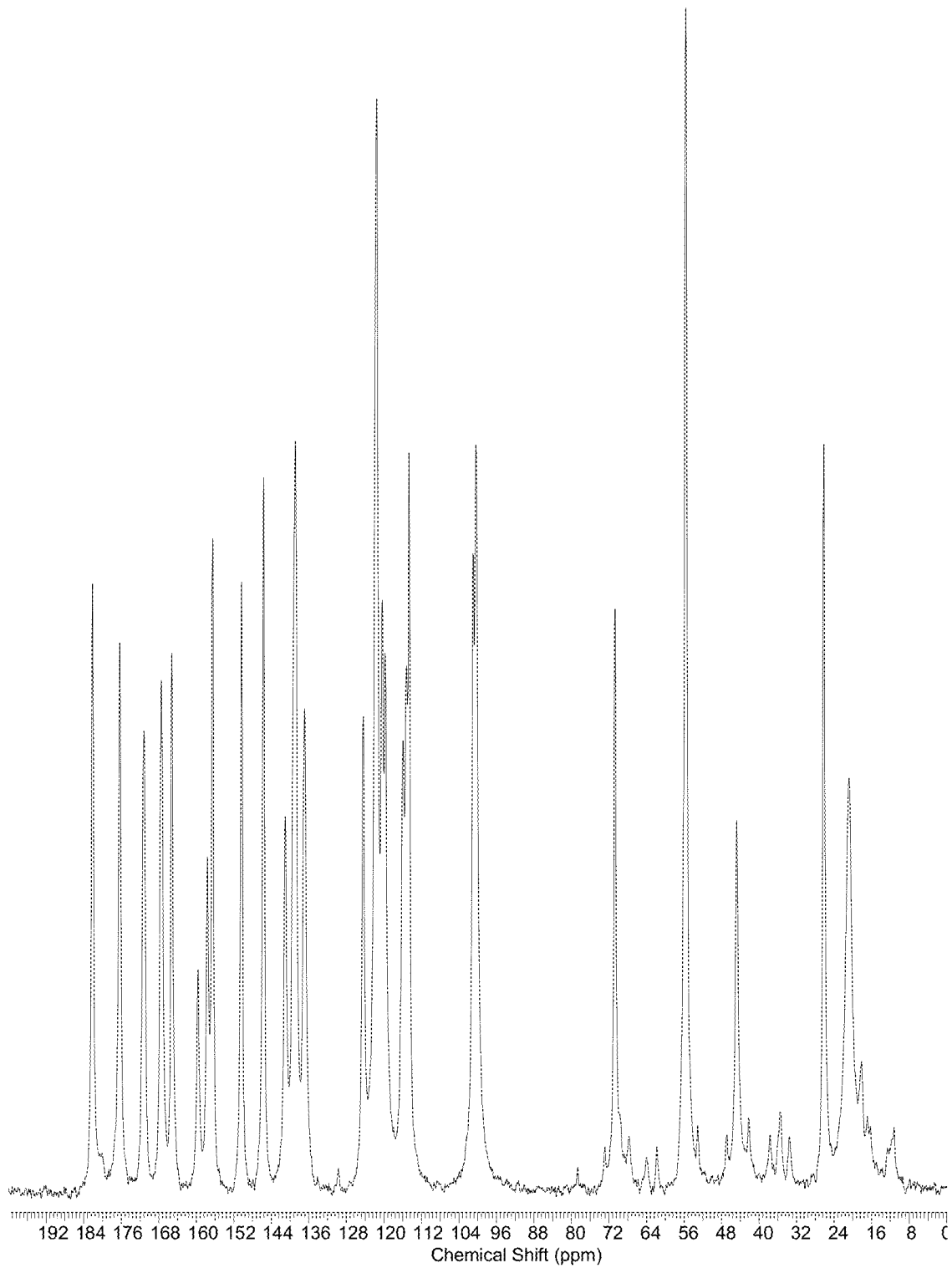
FIG. 16 shows the solid state $^{13}$C NMR spectrum of crystalline Compound (III), Form N-1.

The solid state $^{13}$C NMR spectrum of crystalline Compound (III), Form N-1 is shown in FIG. 16. The entire list of peaks, or a subset thereof, may be sufficient to characterize crystalline Compound (III), Form N-1.

SS $^{13}$C NMR Peaks: 20.8, 26.2, 44.8, 55.7, 70.7, 100.4, 101.0, 114.7, 115.2, 116.0, 119.7, 120.4, 121.6, 124.4, 136.9, 138.9, 141.1, 145.7, 150.3, 156.5, 157.6, 159.6, 165.2, 167.4, 171.2, 176.3, and 182.1 ppm, ±0.2 ppm.

Figure 17:
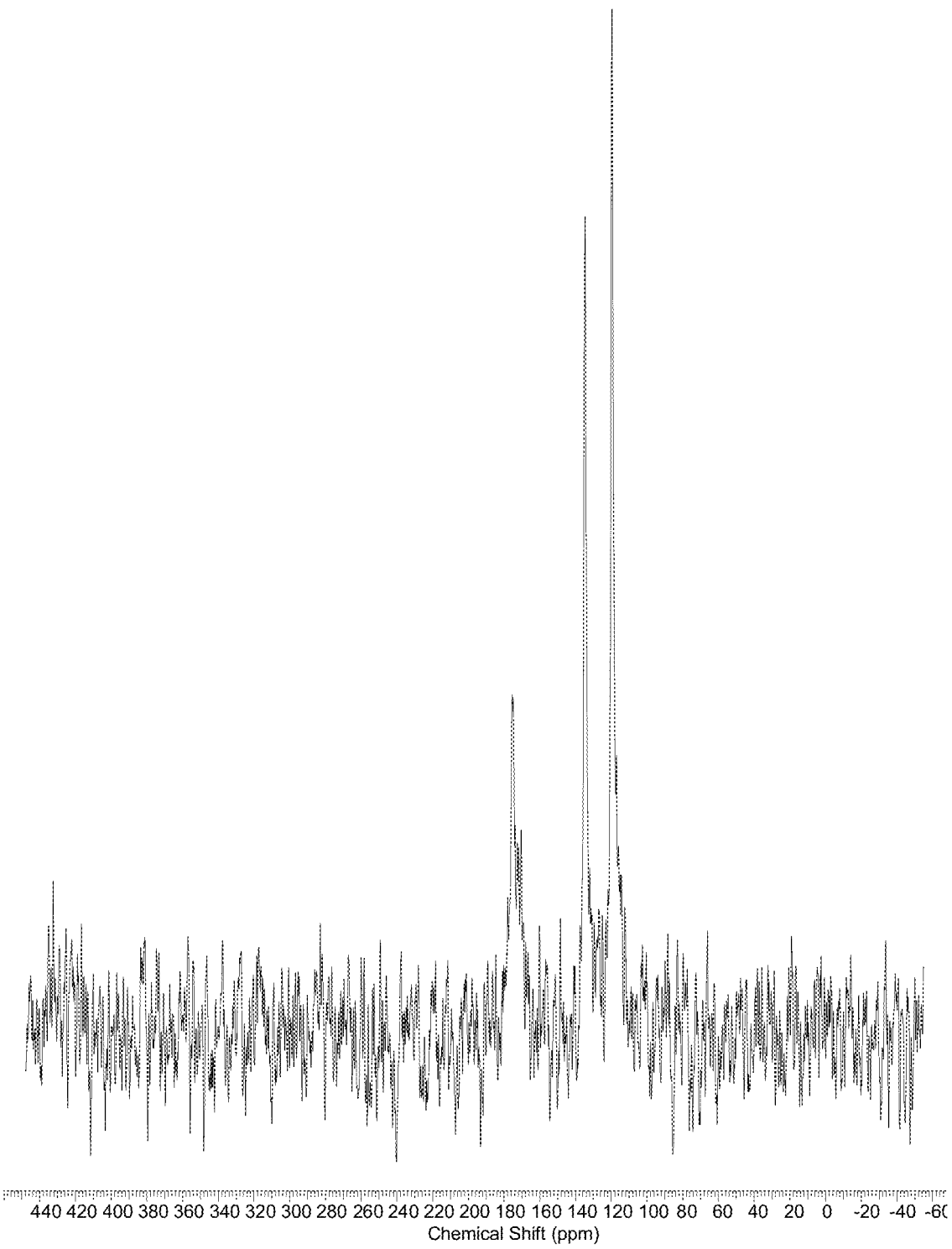
FIG. 17 shows the solid state $^{15}$N NMR spectrum of crystalline Compound (III), Form N-1.

FIG. 17 shows the solid state $^{15}$N NMR spectrum of crystalline Compound (III), Form N-1. The spectrum shows peaks at 119.6, 134.7, and 175.5 ppm, ±0.2 ppm. The entire list of peaks, or a subset thereof, may be sufficient to characterize crystalline Compound (III), Form N-1.

Figure 18:
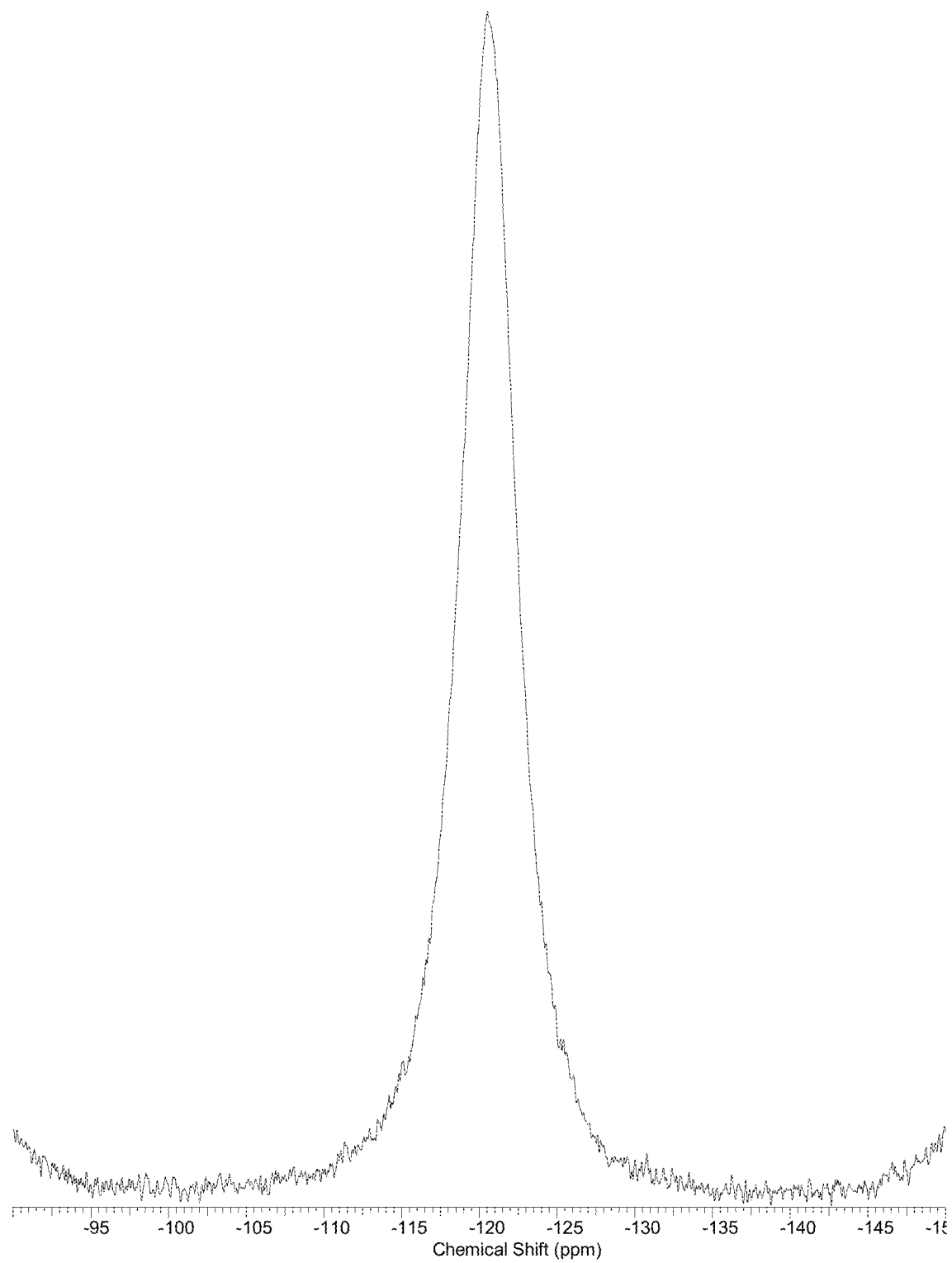
FIG. 18 shows the solid state $^{19}$F NMR spectrum of crystalline Compound (III), Form N-1.

FIG. 18 shows the solid state $^{19}$F NMR spectrum of crystalline Compound (III), Form N-1. The spectrum shows a peak at −120.5 ppm, ±0.2 ppm.

IV.4 Compound (I), Amorphous

Figure 23:
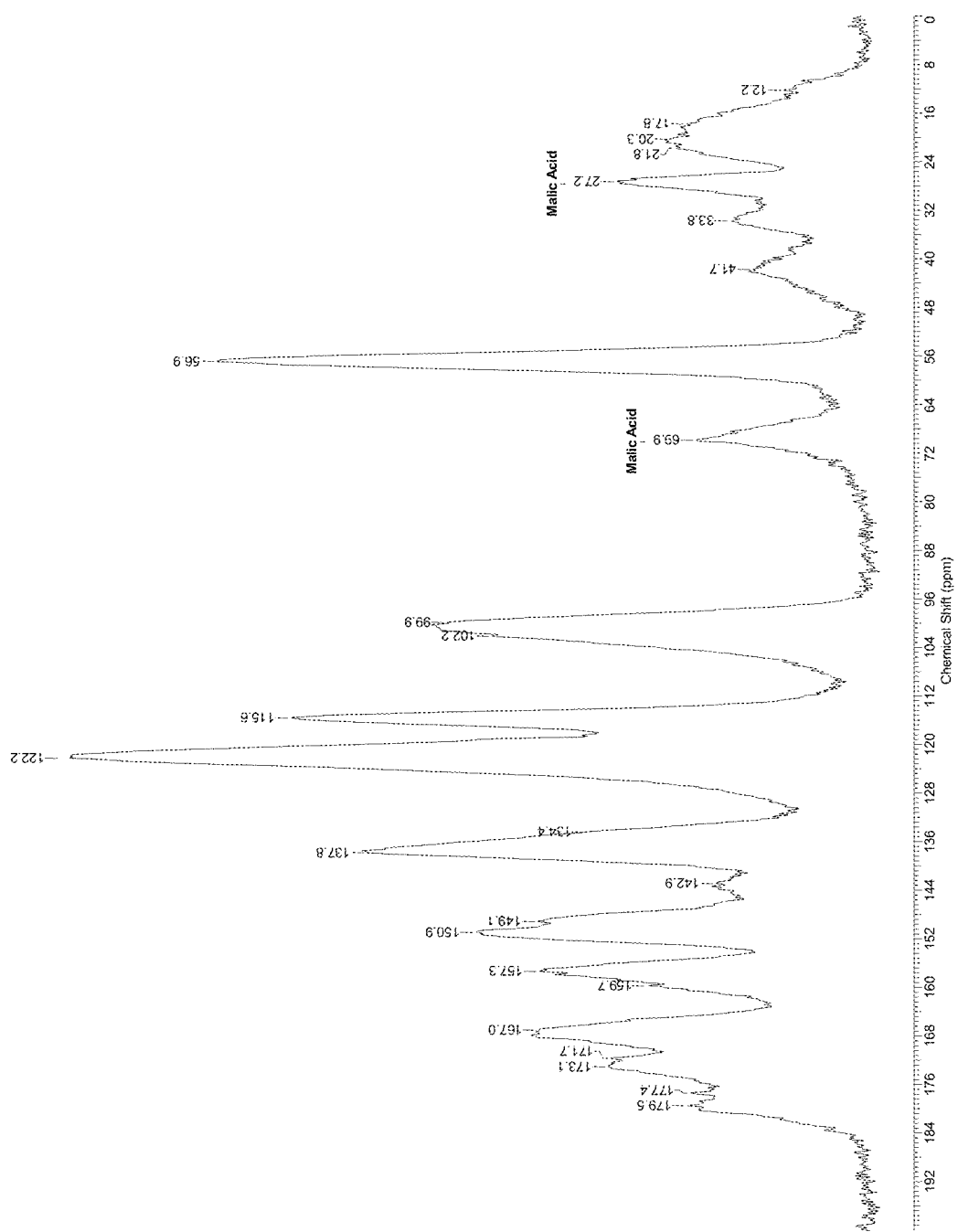
FIG. 23 shows the solid state $^{13}$C NMR spectrum of amorphous Compound (I).

FIG. 23 shows the solid state $^{13}$C NMR spectrum of amorphous Compound (I). The entire list of peaks, or a subset thereof, may be sufficient to characterize amorphous Compound (I).

SS $^{13}$C NMR Peaks (ppm): 12.2, 17.8, 20.3, 21.8, 27.2, 33.8, 41.7, 56.9, 69.9, 99.9, 102.2, 115.6, 122.2, 134.4, 137.8, 142.9, 149.1, 150.9, 157.3, 159.7, 167.0, 171.7, 173.1, 177.4, and 179.5 ppm, ±0.2 ppm.

Figure 24:
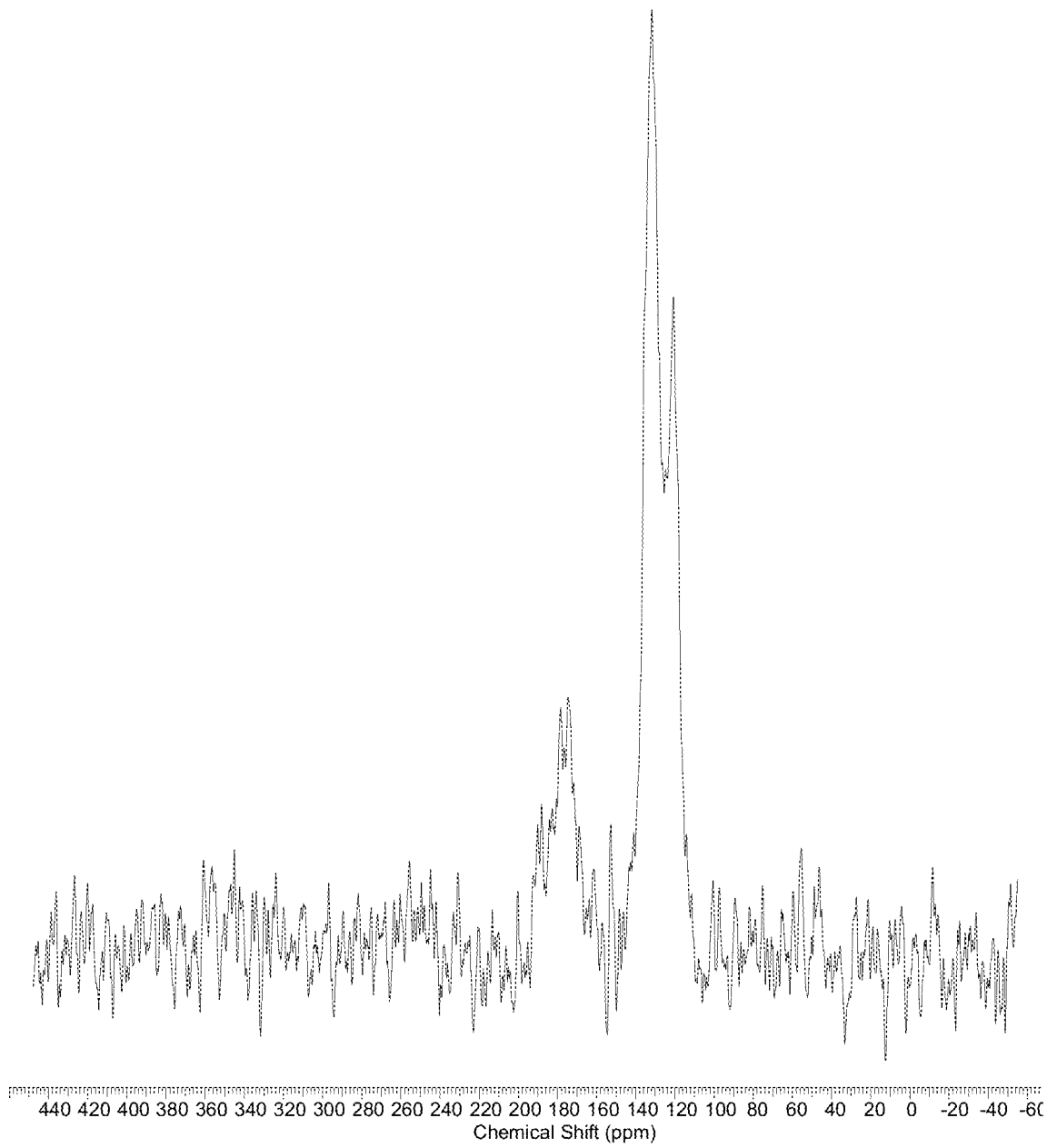
FIG. 24 shows the solid state $^{15}$N NMR spectrum of amorphous Compound (I).

FIG. 24 shows the solid state $^{15}$N NMR spectrum of amorphous Compound (I). The spectrum shows peaks at 120.8, 131.8, 174.7, and 178.3 ppm, ±0.2 ppm. The entire list of peaks, or a subset thereof, may be sufficient to characterize amorphous Compound (I).

Figure 25:
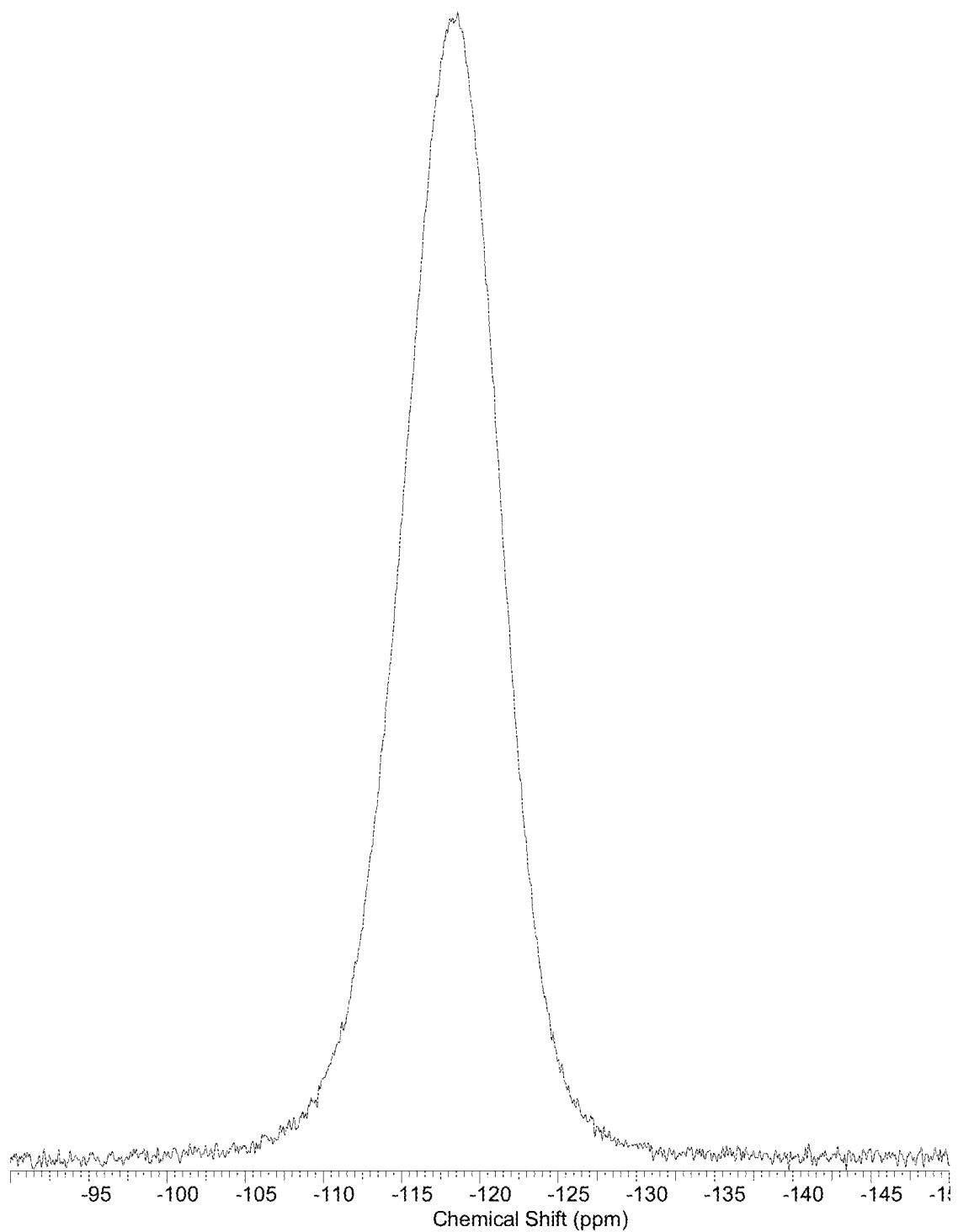
FIG. 25 shows the solid state $^{19}$F NMR spectrum of amorphous Compound (I).

FIG. 25 shows the solid state $^{19}$F NMR spectrum of amorphous Compound (I). The spectrum shows a peak at −118.9 ppm, ±0.2 ppm.

V. Thermal Characterization Measurements

Thermal Gravimetric Analysis (TGA)

The TGA measurements were performed in a TA Instruments™ model Q500 or 2950, employing an open pan setup. The sample (about 10-30 mg) was placed in a platinum pan previously tared. The weight of the sample was measured accurately and recorded to a thousand of a milligram by the instrument. The furnace was purged with nitrogen gas at 100 mL/min. Data were collected between room temperature and 300° C. at 10° C./min heating rate.

Differential Scanning Calorimetry (DSC) Analysis

DSC measurements were performed in a TA Instruments™ model Q2000, Q1000 or 2920, employing an open pan setup. The sample (about 2-6 mg) was weighed in an aluminum pan and recorded accurately recorded to a hundredth of a milligram, and transferred to the DSC. The instrument was purged with nitrogen gas at 50 mL/min. Data were collected between room temperature and 300° C. at 10° C./min heating rate. The plot was made with the endothermic peaks pointing down.

V.1 Compound (I), Form N-1

Figure 5:
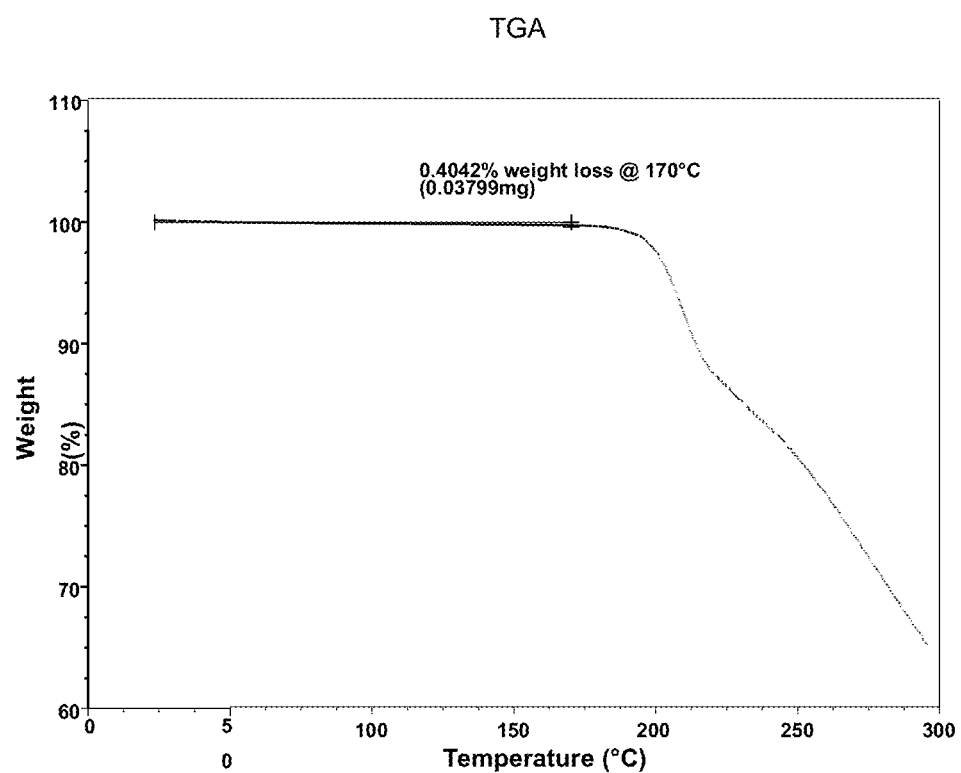
FIG. 5 shows the thermal gravimetric analysis (TGA) of crystalline Compound (I), Form N-1.

FIG. 5 shows the TGA thermogram for crystalline Compound (I), Form N-1, which shows a weight loss of approximately 0.4 weight % at a temperature of 170° C.

Figure 6:
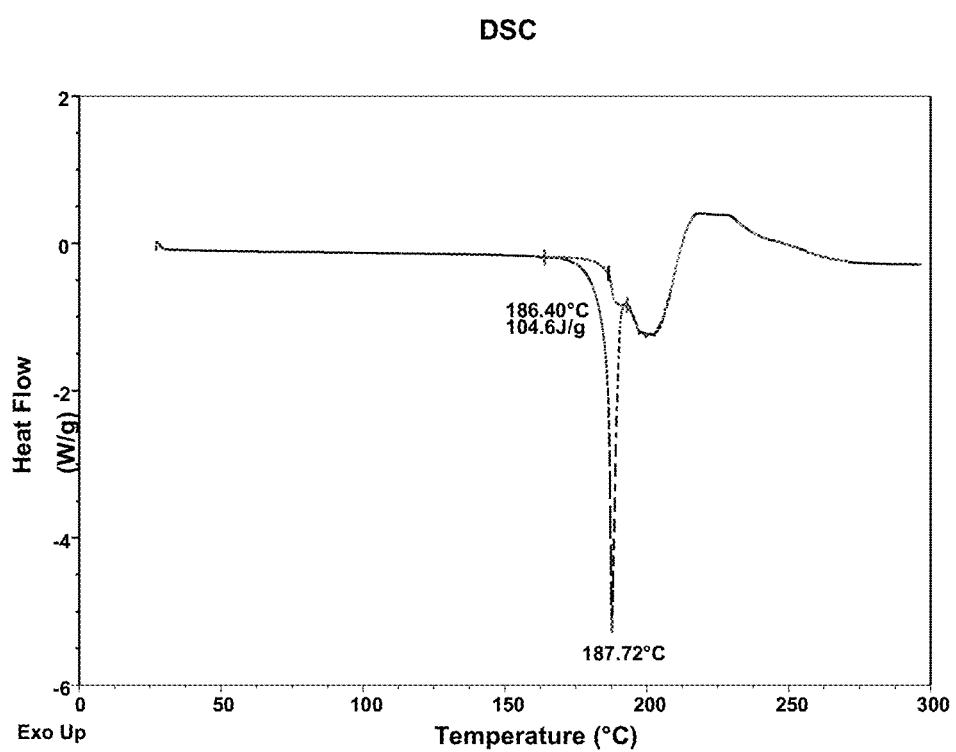
FIG. 6 shows the differential scanning calorimetry (DSC) of crystalline Compound (I), Form N-1.

FIG. 6 shows the DSC thermogram for crystalline Compound (I), Form N-1, which showed a melting point of approximately 187° C.

V.2 Compound (I), Form N-2

Figure 12:
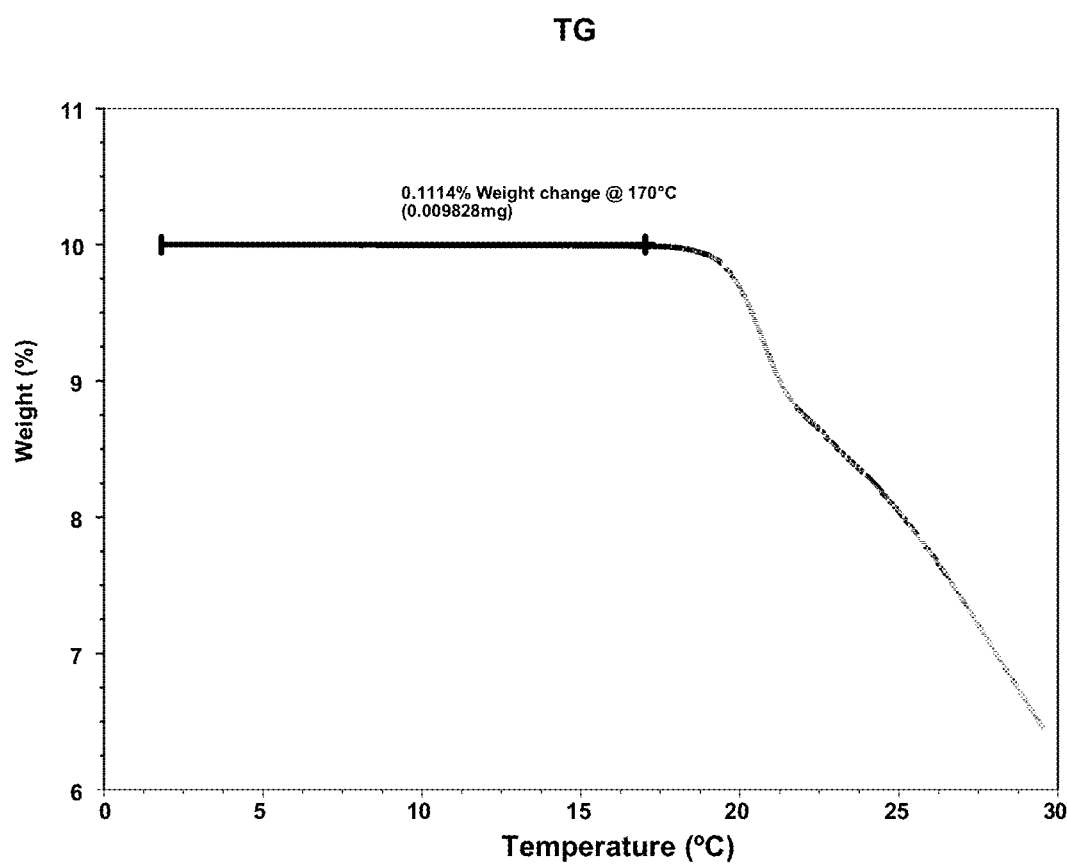
FIG. 12 shows the thermal gravimetric analysis (TGA) of crystalline Compound (I), Form N-2.

FIG. 12 shows the TGA thermogram for crystalline Compound (I), Form N-2, which shows a weight loss of approximately 0.1 weight % at a temperature of 170° C.

Figure 13:
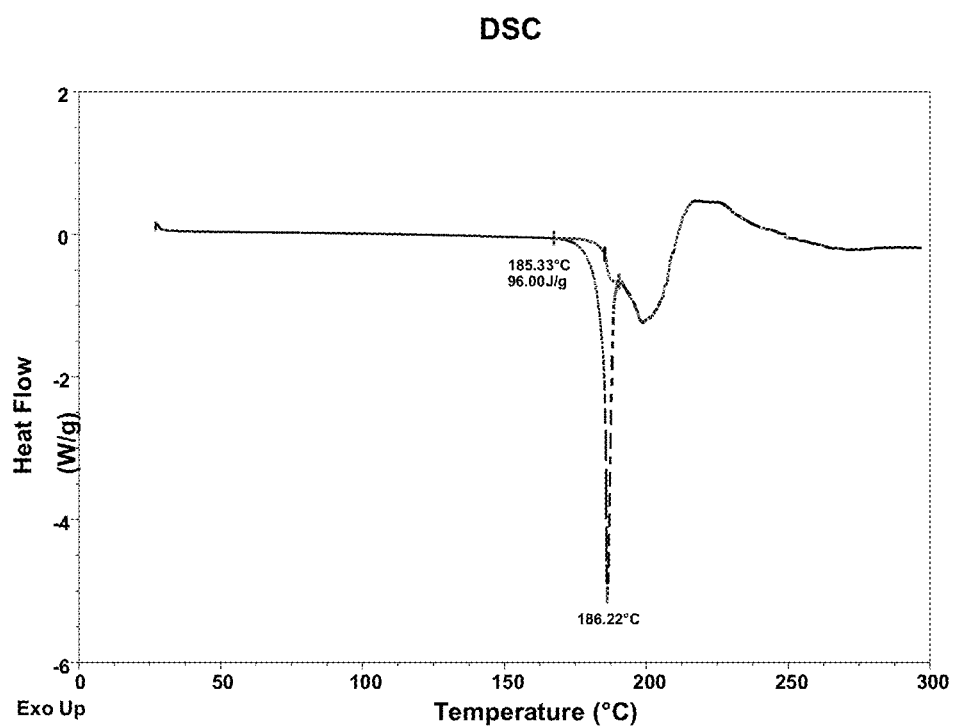
FIG. 13 shows the differential scanning calorimetry (DSC) of crystalline Compound (I), Form N-2.

FIG. 13 shows the DSC thermogram for crystalline Compound (I), Form N-2, which showed a melting point of approximately 186° C.

V.3 Compound (III), Form N-1

Figure 19:
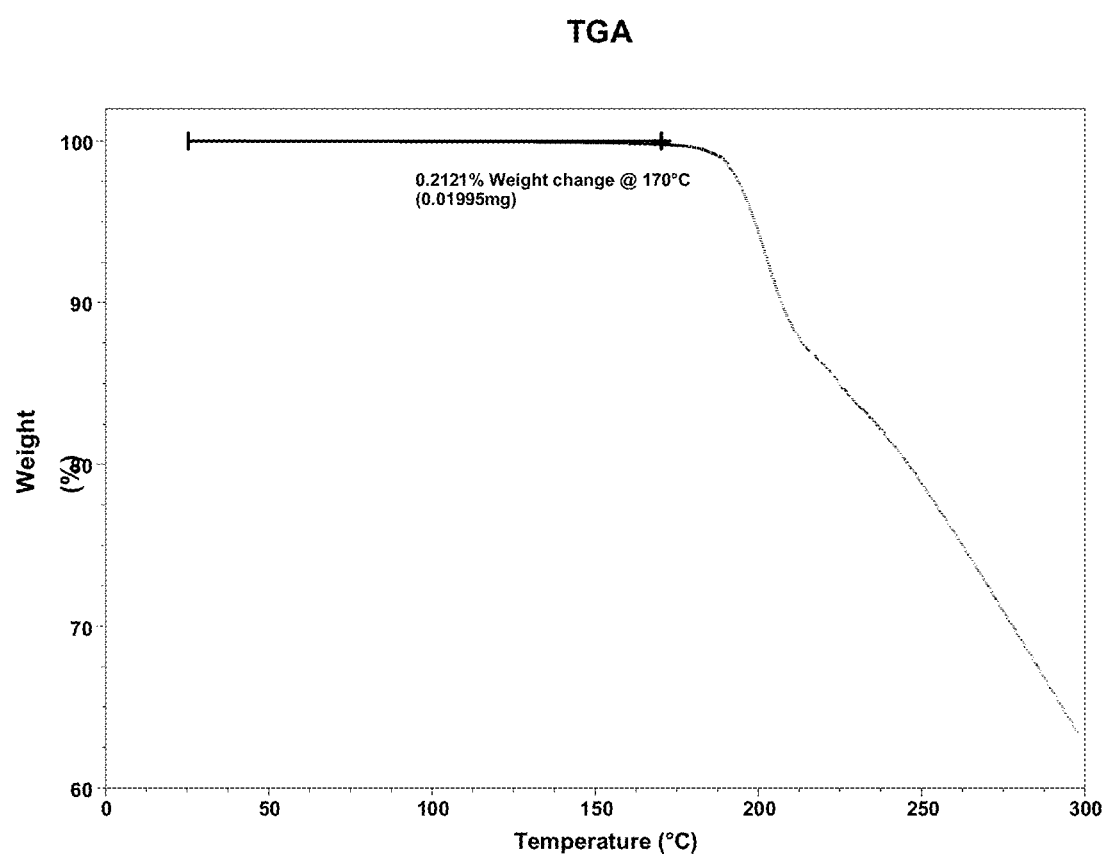
FIG. 19 shows the thermal gravimetric analysis (TGA) of crystalline Compound (III), Form N-1.

FIG. 19 shows the TGA thermogram for crystalline Compound (III), Form N-1, which shows a weight loss of approximately 0.2 weight % at a temperature of 170° C.

Figure 20:
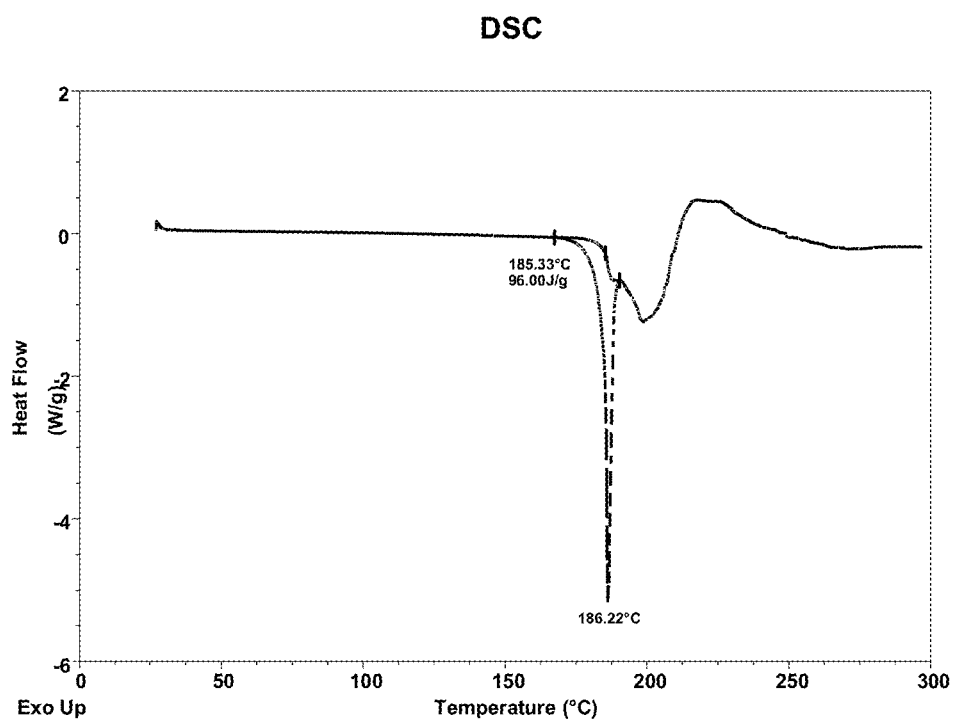
FIG. 20 shows the differential scanning calorimetry (DSC) of crystalline Compound (III), Form N-1.

FIG. 20 shows the DSC thermogram for crystalline Compound (III), Form N-1, which showed a melting point of approximately 186° C.

V.2 Compound (I), Amorphous

Figure 26:
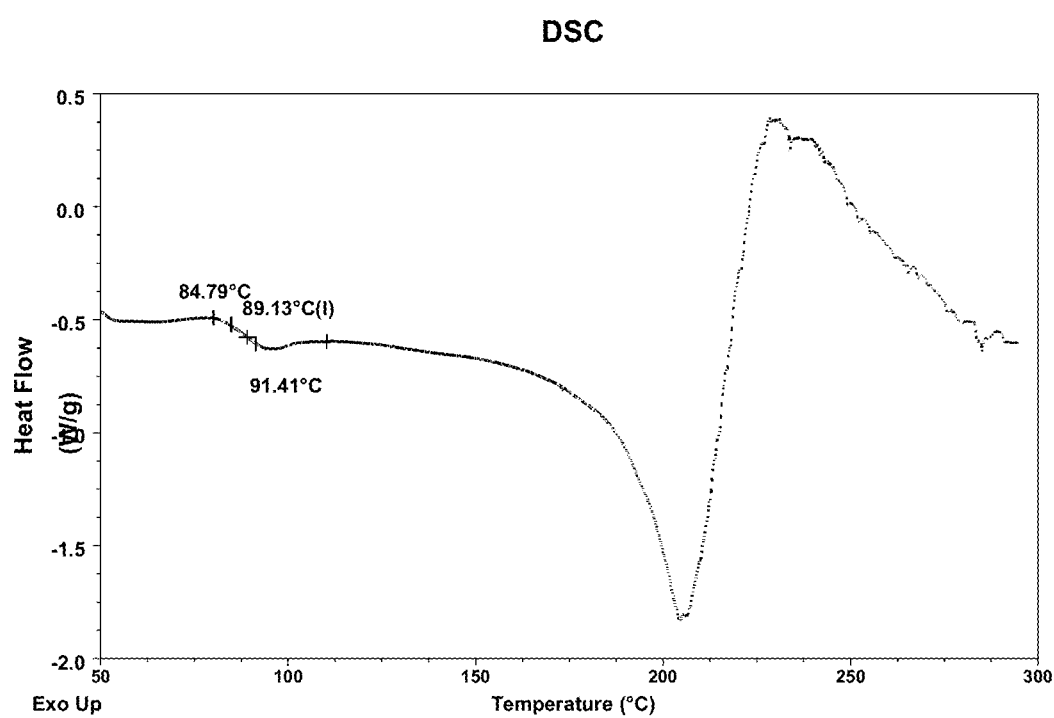
FIG. 26 shows the differential scanning calorimetry (DSC) of amorphous Compound (I).

FIG. 26 shows the DSC for crystalline Compound (I).

VI. Moisture Vapor Isotherm Measurements

Moisture sorption isotherms were collected in a VTI SGA-100 Symmetric Vapor Analyzer using approximately 10 mg of sample. The sample was dried at 60° C. until the loss rate of 0.0005 wt %/min was obtained for 10 minutes. The sample was tested at 25° C. and 3 or 4, 5, 15, 25, 35, 45, 50, 65, 75, 85, and 95% RH. Equilibration at each RH was reached when the rate of 0.0003 wt %/min for 35 minutes was achieved or a maximum of 600 minutes.

VI.1 Compound (I), Form N-1

Figure 7:
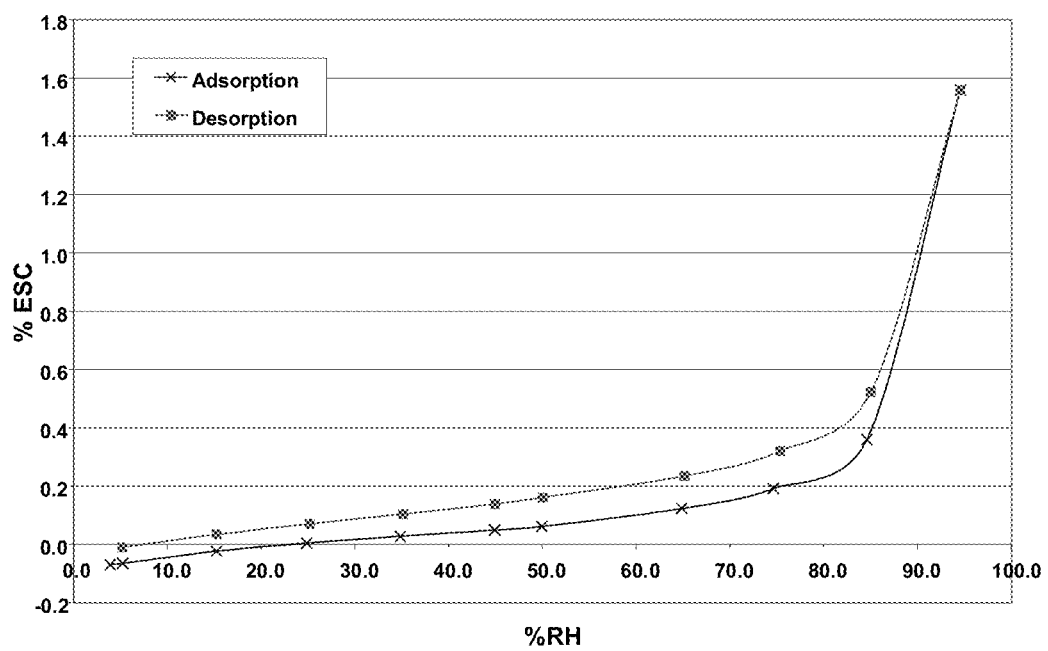
FIG. 7 shows the moisture sorption of crystalline Compound (I), Form N-1.

FIG. 7 shows the moisture vapor isotherm of crystalline Compound (I), Form N-1.

VI.2 Compound (I), Form N-1

Figure 14:
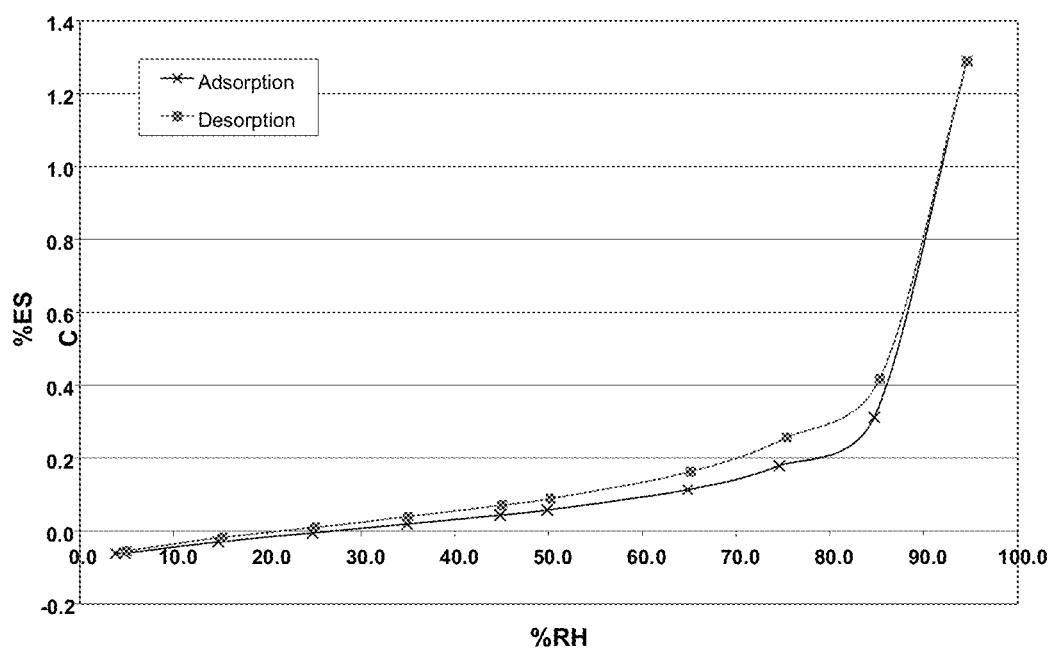
FIG. 14 shows the moisture sorption of crystalline Compound (I), Form N-2.

FIG. 14 shows the moisture vapor isotherm of crystalline Compound (I), Form N-2.

VI.3 Compound (III), Form N-1

Figure 21:
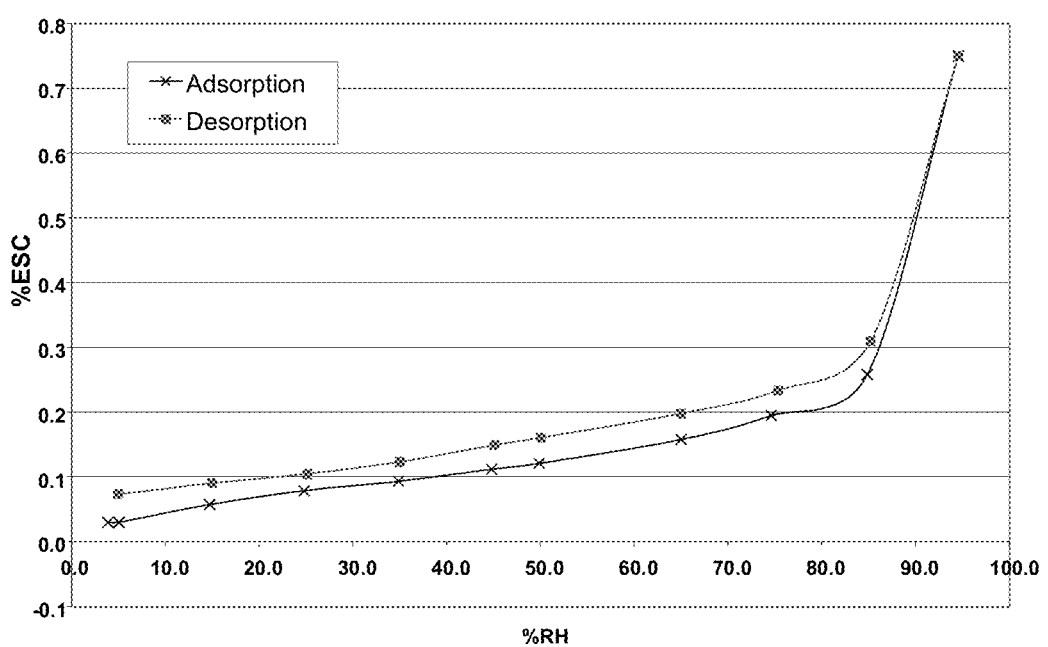
FIG. 21 shows the moisture sorption of crystalline Compound (III), Form N-1.

FIG. 21 shows the moisture vapor isotherm of crystalline Compound (III), Form N-1.

VI.4 Compound (I), Amorphous

Figure 27:
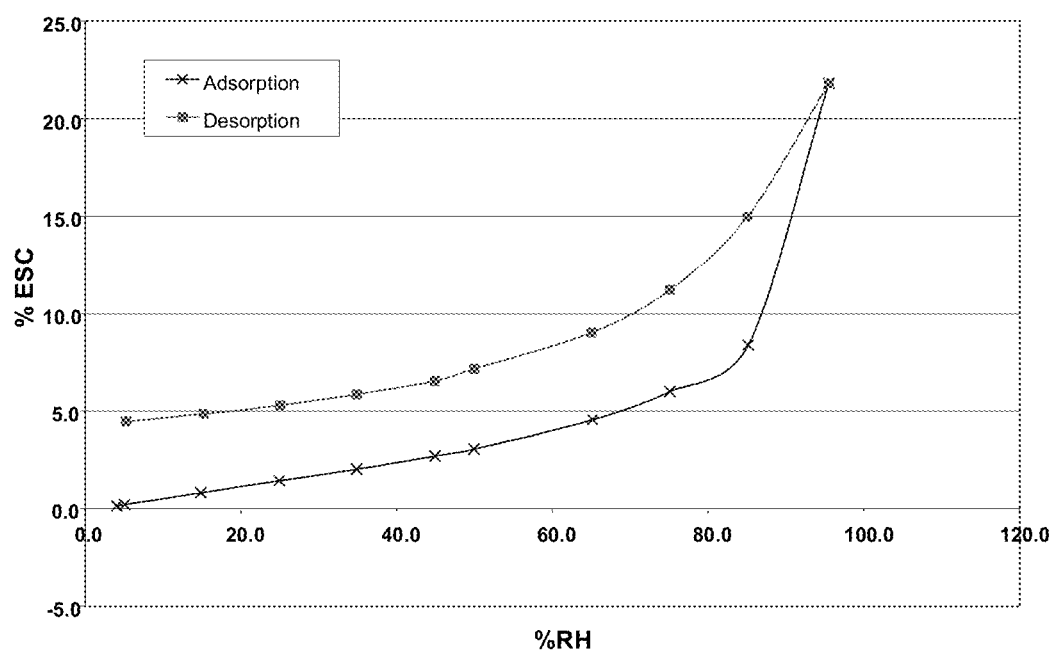
FIG. 27 shows the moisture sorption of amorphous Compound (I).

FIG. 27 shows the moisture vapor isotherm of amorphous Compound (I).

The foregoing disclosure has been described in some detail by way of illustration and example, for purposes of clarity and understanding. The invention has been described with reference to various specific and preferred embodiments and techniques. However, it should be understood that many variations and modifications can be made while remaining within the spirit and scope of the invention. It will be obvious to one of skill in the art that changes and modifications can be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

What is claimed is:

1. A method of treating cancer, comprising administering to a subject in need thereof N-(4-{[6,7-bis(methyloxy)quinolin-4-yl]oxy}phenyl)-N'-(4-fluorophenyl) cyclopropane-1,1-dicarboxamide, malate salt, wherein said salt is the (L)-malate salt or the (D)-malate salt, and wherein said salt is crystalline.

2. A method of treating cancer, comprising administering to a subject in need thereof N-(4-{[6,7-bis(methyloxy)quinolin-4-yl]oxy}phenyl)-N'-(4-fluorophenyl) cyclopropane-1,1-dicarboxamide, malate salt, wherein said salt is the (L)-malate salt or the (D)-malate salt, said salt is crystalline, and said cancer is kidney cancer.

3. A method of treating cancer, comprising administering to a subject in need thereof N-(4-{[6,7-bis(methyloxy)quinolin-4-yl]oxy}phenyl)-N'-(4-fluorophenyl) cyclopropane-1,1-dicarboxamide, malate salt, wherein said salt is the (L)-malate salt or the (D)-malate salt, said salt is crystalline, and said cancer is liver cancer.

* * * * *